(12) United States Patent
Iyer et al.

(10) Patent No.: US 10,408,783 B2
(45) Date of Patent: Sep. 10, 2019

(54) ELECTROCHEMICAL METHODS AND COMPOUNDS FOR THE DETECTION OF ENZYMES

(71) Applicant: GEORGIA STATE UNIVERSITY RESEARCH FOUNDATION, INC., Atlanta, GA (US)

(72) Inventors: Suri Saranathan Iyer, Norcross, GA (US); Abasaheb Dhawane, Atlanta, GA (US); Yun He, Atlanta, GA (US); Xiaohu Zhang, Duluth, GA (US); Hieu Dinh, Ellenwood, GA (US); Mugdha Vasireddi, Tucker, GA (US); Joyce Sweeney, Atlanta, GA (US)

(73) Assignee: GEORGIA STATE UNIVERSITY RESEARCH FOUNDATION, INC., Atlanta, GA (US)

( * ) Notice: Subject to any disclaimer, the term of this patent is extended or adjusted under 35 U.S.C. 154(b) by 209 days.

(21) Appl. No.: 15/314,817

(22) PCT Filed: Jun. 1, 2015

(86) PCT No.: PCT/US2015/033512
§ 371 (c)(1),
(2) Date: Nov. 29, 2016

(87) PCT Pub. No.: WO2015/184442
PCT Pub. Date: Dec. 3, 2015

(65) Prior Publication Data
US 2017/0102349 A1    Apr. 13, 2017

Related U.S. Application Data

(60) Provisional application No. 62/005,407, filed on May 30, 2014, provisional application No. 62/091,205, filed on Dec. 12, 2014.

(51) Int. Cl.
*G01N 27/327* (2006.01)
*C12Q 1/34* (2006.01)
(Continued)

(52) U.S. Cl.
CPC .......... *G01N 27/3275* (2013.01); *C07H 3/04* (2013.01); *C07H 15/04* (2013.01); *C07H 15/18* (2013.01);
(Continued)

(58) Field of Classification Search
CPC .......... G01N 27/3275; G01N 27/3272; G01N 27/307; G01N 2333/924; G01N 2333/11;
(Continued)

(56) References Cited

U.S. PATENT DOCUMENTS 5,658,880 A * 8/1997 Dasgupta .......... A61K 31/7012
  514/1.4
5,789,385 A * 8/1998 Anderson .......... A61K 31/7012
  514/24

(Continued)

FOREIGN PATENT DOCUMENTS

WO    9109972 A1    7/1991
WO    9216647 A1    10/1992
(Continued)

OTHER PUBLICATIONS

Entry for NeuAc alpha 2-3 Gal. National Center for Biotechnology Information. PubChem Compound Database; CID=13832708, https://pubchem.ncbi.nlm.nih.gov/compound/13832708 (accessed Sep. 14, 2018). (Year: 2007).*
(Continued)

*Primary Examiner* — J. Christopher Ball
(74) *Attorney, Agent, or Firm* — Meunier Carlin & Curfman LLC

(57) ABSTRACT

Disclosed are compositions and methods for the electrochemical detection of enzymes, such as enzymes that are
(Continued)

indicative of disease, disorders, or pathogens, such as viruses, bacteria, and fungi, or other disorders. These methods can be used in point-of-care diagnostic assays for the detection of disease, disorder, or pathogen (e.g., to identify the strain of pathogen infecting a patient in a healthcare setting). The electrochemical methods described herein can also be used to assess the susceptibility of a pathogen to an antipathogen drug. Also provided are probes suitable for use in conjunction with the methods described herein.

17 Claims, 10 Drawing Sheets

(51) Int. Cl.
    C07H 15/04      (2006.01)
    C07H 15/18      (2006.01)
    C07H 15/203     (2006.01)
    C07H 17/075     (2006.01)
    C07H 3/04       (2006.01)
    C12Q 1/40       (2006.01)
    G01N 27/30      (2006.01)
(52) U.S. Cl.
    CPC ......... *C07H 15/203* (2013.01); *C07H 17/075* (2013.01); *C12Q 1/34* (2013.01); *C12Q 1/40* (2013.01); *C12Y 302/01018* (2013.01); *G01N 27/307* (2013.01); *G01N 27/3272* (2013.01); *G01N 2333/11* (2013.01); *G01N 2333/924* (2013.01)
(58) Field of Classification Search
    CPC .. C12Y 302/01018; C07H 3/04; C07H 15/18; C07H 15/203; C07H 15/04; C07H 17/075; C12Q 1/40; C12Q 1/34
    See application file for complete search history.

(56) References Cited

U.S. PATENT DOCUMENTS

| | | | |
|---|---|---|---|
| 5,912,115 | A | 6/1999 | Maresch et al. |
| 6,682,648 | B1 | 1/2004 | MacPhee et al. |
| 8,945,943 | B2 | 2/2015 | Lu et al. |
| 2008/0286758 | A1 | 11/2008 | Li et al. |
| 2012/0122079 | A1 | 5/2012 | Koglin et al. |
| 2013/0267433 | A1 | 10/2013 | Cha et al. |

FOREIGN PATENT DOCUMENTS

| | | |
|---|---|---|
| WO | 03062822 A1 | 7/2003 |
| WO | 2006103450 A2 | 10/2006 |
| WO | 2007087468 A2 | 8/2007 |
| WO | 2008009046 A1 | 1/2008 |

OTHER PUBLICATIONS

Entry for NeuAc alpha 2-6 Gal beta. National Center for Biotechnology Information. PubChem Compound Database; CID=5289369, https://pubchem.ncbi.nlm.nih.gov/compound/5289369 (accessed Sep. 14, 2018). (Year: 2005).*
J. Deng, et al. Construction of Effective Receptor for Recognition of Avian Influenza H5N1 Protein HA1 by Assembly of Monohead Glycolipids on Polydiacetylene Vesicle Surface, Bioconjugate Chemistry, 20(3): p. 533-537, Feb. (Year: 2009).*
C.A. Togo, et al. "Novel detection of *Escherichia coli* β-D-glucuronidase activity using a microbially-modified glassy carbon electrode and its potential for faecal pollution monitoring", Biotechnology Letters, 29(4): p. 531-537, Apr. (Year: 2007).*
Communication Pursuant to Rule 164(1), issued in related European Application No. EP15799039, dated Dec. 22, 2017.
Eschenfelder, V., et al., "3 C-Untersuceungenvon Anoneren Ketosidbn Der N-Acetyl-D-Nburaninsaubb", Tetrahedron Letters No..,, Jan. 1, 1975, 3069-3072.
Ito, Yukishige, et al., "Highly stereoselective glycisylation of N-acetylneuraminic acid aided by a phenylthio substituent as a stereocontrolling auxiliary", Tetrahedron Letters, vol. 29, No. 32, Jan. 1, 1988, pp. 3987-3990.
Ito, Yukishige, et al., "An efficient approach to streoselective glycosylation of N-acetylneuraminic acid: Used of phenylselenyl group as a stereocontrolling auxiliary", Tetrahedron Letters, Jan. 1, 1987, 6221-6224.
Khorlin, A Ya. et al., "Vhe synthesis of N-acetylneurarninyl-(2+3)- and-(a-+6)-hexoses", Academy of Sciences Carbohyd. Res, 272-275, Jan. 1, 1970.
Sabesan, S., et al., "Conformational analysis of sialyloligosaccharides", Carbohydrate Research, Pergamon, GB vol. 218, Sep. 30, 1991, 27-54.
Sabesan, Subramanian, et al., "The confromational properties of the gangliosides based on 'H and I3C nuclear magnetic resonance studie", Can. J. Chem, vol. 62, Jan. 1, 1984, 1034-1045.
Van Der Vleugel, Dominicus J. et al., "A facile preparation of alkyl [alpha]-glycosides of the methyl ester of N-acetyl-d-neuraminic acid", Carbohydrate Research, Jan. 1, 1982, 121-130.
C. J. Ballesta, M. M. C. Valencia, L. F. Capitan-Vallvey, Disposable electrochemiluminescent biosensor for lactate determination in saliva. *Analyst* (Cambridge, U. K.) 134, 1423 (2009).
J. Ballesta-Claver et al., Electrochemiluminescent disposable cholesterol biosensor based on avidin-biotin assembling with the electroformed luminescent conducting polymer poly(luminol-biotinylated pyrrole). *Anal. Chim. Acta* 754, 91 (2012).
L. Cheng, S. Deng, J. Lei, H. Ju, Disposable electrochemiluminescent biosensor using bidentate-chelated CdTe quantum dots as emitters for sensitive detection of glucose. *Analyst* (*Cambridge, U. K.*) 137, 140 (2012).
M. S. Chiriaco et al., On-chip screening for prostate cancer: an EIS microfluidic platform for contemporarydetection of free and total PSA. *Analyst* (*Cambridge, U. K.*) 138, 5404 (2013).
B. Elsholz et al., Electrical microarrays for highly sensitive detection of multiplexPCR products from biological agents. *Biosens. Bioelectron.* 24, 1737 (2009).
International Search Reportand Written Opinion issued in related International Application No. PCT/US2015/033512 dated Aug. 14, 2015.
C. Liao, M. Zhang, L. Niu, Z. Zheng, F. Yan, Highly selective and sensitive glucose sensors based on organic electrochemical transistors with graphene-modified gate electrodes. *J. Mater. Chem. B* 1, 3820 (2013).
A. Martinez-Olmos, J. Ballesta-Claver, A. J. Palma, M. d. C. Valencia-Miron, L. F. Capitan-Vallvey, A portable luminometer with a disposable electrochemiluminescent biosensor for lactate determination. *Sensors* 9, 7694 (2009).
H. Mohapatra et al., Reagents and assaystrategies for quantifying active enzyme analytes using a personal glucose meter., Chem. Commun., 49, 6134 (2013).
R. Monosik, M. Stred'ansky, E. Sturdik, Application of electrochemical biosensors in clinical diagnosis. *J. Clin. Lab. Anal.* 26, 22 (2012).
K. Peters, F. M. Richards, Chemical cross-linking: reagents and problems in studies of membrane structure. *Annu. Rev. Biochem.* 46, 523 (1977).
M. Potier, L. Mameli, M. Belisle, L. Dallaire, S. B. Melancon, Fluorometric assay of neuraminidase with a sodium (4-methylumbelliferyl-α-D-N-acetylneuraminate) substrate. *Anal. Biochem.* 94, 287 (1979).
PUBCHEM CID 446069,"2-O-Methyl-5-N-Acetyl-Alpha-D-Neraminic Acid", Jun. 24, 2005.
PUBCHEM CID 14826617,"2-O-Propyl-5-N-acetyl-alpha-D-neuraminic acid". Feb. 9, 2007.
R. L. Rubin, D. Wall, K. N. Konstantinov, Electrochemical biosensor for quantitation of anti-DNA autoantibodies in human serum. *Biosens. Bioelectron.* 51, 177 (2014).

(56) References Cited

OTHER PUBLICATIONS

A. Safavi, F. Farjami, Electrodeposition of gold-platinum alloy nanoparticles on ionic liquid-chitosan composite film and its application in fabricating an amperometric cholesterol biosensor. *Biosens. Bioelectron.* 26, 2547 (2011).

H. Shafiee et al., Acute On-Chip HIV Detection Through Label-Free Electrical Sensing of Viral Nano-Lysate. *Small* 9, 2553 (2013).

H. Shu, W. Wen, H. Xiong, X. Zhang, S. Wang, Novel electrochemical aptamer biosensor based on gold nanoparticles signal amplification for the detection of carcinoembryonic antigen. *Electrochem. Commun.* 37, 15 (2013).

R. Singhal, A. Gambhir, M. K. Pandey, S. Annapoorni, B. D. Malhotra, Immobilization of urease on poly(N-vinyl carbazole)/stearic acid Langmuir-Blodgett films for application to urea biosensor. *Biosens. Bioelectron.* 17, 697 (2002).

K. Sirkar, M. V. Pishko, Amperometric Biosensors Based on Oxidoreductases Immobilized in Photopolymerized Poly(ethylene glycol) Redox Polymer Hydrogels. *Anal. Chem.* 70, 2888 (1998).

X.-C. Tan, Y.-X. Tian, P.-X. Cai, X.-Y. Zou, Glucose biosensor based on glucose oxidase immobilized in sol-gel chitosan/silica hybrid composite film on Prussian blue modified glass carbon electrode. *Anal. Bioanal. Chem.* 381, 500 (2005).

J.-Z. Tao et al., Poly(m-phenylenediamine)-Prussian blue hybrid film formed by one-step electrochemical deposition for glucose biosensor. *J. Electroanal. Chem.* 689, 96 (2013).

S. Wu, G. Liu, P. Li, H. Liu, H. Xu, A high-sensitive and fast-fabricated glucose biosensor based on Prussian blue/topological insulator $Bi_2Se_3$ hybrid film. *Biosens. Bioelectron.* 38, 289 (2012).

Q. Wu, L. Wang, H.-J. Yu, J.-J. Wang, Z.-F. Chen, Organization of Glucose-Responsive Systems and Their Properties. *Chem. Rev.* (Washington, DC, U. S.) 111, 7855 (2011).

Y. Xiang et al., Using personal glucose meters and functional DNAsensors to quantify a variety of analytical targets., Nat Chem; 3(9): 697-703 (2012).

O. Yilmaz et al., Chitosan-ferrocene film as a platform for flow injection analysis applications of glucose oxidase and Gluconobacter oxydans biosensors. *Colloids Surf., B* 100, 62 (2012).

X. Zhang et al., Electrochemical Assayto Detect Influenza Viruses and Measure Drug Susceptibility. Agnew. Che. Int. Ed 2015, 54, 1-5 (2015).

\* cited by examiner

FIG. 3A

Legend:
- 50uM GLUCOSE
- 100uM GLUCOSE
- 100uM SG with H3N2 virus
- 100uM SG with H3N2 NA
- 100uM SG with H5N1 NA
- 100uM SG with H1N1 virus

FIG. 3B

Legend:
- 100uM GLUCOSE
- 100uM SG with H1N1 for 1h
- 100uM SG with H1N1 overnight
- 100uM SG with H1N1 for 5h

ELECTROCHEMICAL METHODS AND COMPOUNDS FOR THE DETECTION OF ENZYMES

CROSS-REFERENCE TO RELATED APPLICATIONS

This application is a national stage application filed under 35 U.S.C. § 371 of PCT/US2015/033512 filed Jun. 1, 2015, which claims the benefit of U.S. Provisional Application No. 62/005,407, filed May 30, 2014, and Application Ser. No. 62/091,205, filed Dec. 12, 2014, which are hereby incorporated herein by reference in their entirety.

STATEMENT REGARDING FEDERALLY SPONSORED RESEARCH OR DEVELOPMENT

This invention was made with Government Support under Grant No. AI089450 awarded by the National Institutes of Health. The Government has certain rights in the invention.

BACKGROUND

Epidemic viral infections are responsible for significant worldwide loss of life and income in human illnesses ranging from the common cold to life-threatening influenza, West Nile, and HIV infections. Timely detection, diagnosis and treatment are key in limiting spread of disease in epidemic, pandemic and epizootic settings. Rapid screening and diagnostic methods are particularly useful in reducing patient suffering and population risk. Similarly, therapeutic agents that rapidly inhibit viral assembly and propagation are particularly useful in treatment regimens.

Influenza has emerged as a potentially significant risk to human populations. Influenza can infect as much as 5-15% of the world population annually, resulting in 3-5 million cases of severe illness and up to 500,000 deaths each year. In the U.S. alone, flu epidemics lead to approximately 300,000 influenza-related hospital admissions and 36,000 influenza-related deaths annually in addition to an estimated cost of $12 billion per year. Avian strains have also crossed into humans, and there is growing evidence that the human-to-human transmission of avian strains has occurred in the past. The pandemic strains can kill far more people, for example, the 1918 strain has been reported to kill ~50 million people worldwide, more than people killed during the first world war.

Virology test methods for detection and confirmation of influenza infection in a virus-secure reference laboratory (e.g., satisfying requirements for Containment Group 2/3/4 pathogens) are time consuming, high-risk and laborious (i.e., involving 4-7 days isolation of the virus in embryonated eggs; harvesting allantoic fluids from dead or dying embryos; testing the fluid in hemagglutination and hemagglutination inhibition tests, immunodiffusion; and, eventual subtyping of the virus in the fluid by hemagglutinin and neuraminidase in overnight immunodiffusion assays using specially prepared monospecific antisera). Present subtyping of influenza involves identifying each of 16 different possible viral hemagglutinin proteins in combination with 9 different possible viral neuraminidase proteins.

Rapid immunodiagnostic tests for influenza antigens have been developed, and include BINAXNOW FluA and FluB (Binax, Inc., Portland, Me.), DIRECTIGEN Flu A+B (Becton Dickinson, Franklin Lakes, N.J.), FLU OIA (Biostar Inc., Boulder, Colo.), QUICKVUE (Quidel, Sand Diego, Calif.), INFLU AB QUICK (Denka Sieken Co., Ltd., Japan) and XPECT FLU A & B (Remel Inc., Lenexa, Kans.). These assays can reportedly either detect influenza A or distinguish between Influenza A and B, but importantly, not between different influenza A subtypes or between pathogenic and non-pathogenic strains of influenza A. Moreover, these tests cannot determine resistance to FDA approved antivirals and exhibit high false negative results with emerging strains.

Recent introduction of reverse-transcriptase PCR-based diagnostics (RT-PCR) for confirming influenza A virus have resulted in important advances in diagnostics, but because of the relative inefficiency of the reverse transcriptase enzyme and significant amounts of virus required (e.g., $10^4$ virion particles), high throughput screening of subjects with RT-PCR in an epidemic setting is not practical. These tests are typically performed in clinical laboratory by trained personnel.

Additionally, the complexity, diversity and rapid emergence of new influenza strains has made the diagnosis of high risk strains difficult using conventional approaches. For epidemiologists, diversity resulting from high mutation rates and genetic reassortment make it challenging to anticipate where new strains may originate. Thus, there remains a significant need in the medical arts for improved, inexpensive, rapid, accurate and discriminatory methods capable of detecting influenza and identifying influenza strains, particularly in point-of-care settings, as well as determining the antiviral resistance of influenza strains.

SUMMARY

Disclosed are compositions and methods for the electrochemical detection of enzymes, such as enzymes that are indicative of disease, disorders, or pathogens, such as viruses, bacteria, and fungi, or other disorders. The methods involve providing a probe comprising a substrate that releases an electrochemically active moiety when cleaved by an enzyme. When the appropriate probe that includes a substrate for an enzyme of interest is exposed to the enzyme of interest, the enzyme reacts with the probe to liberate the electrochemically active moiety. The free electrochemically active moiety can then be detected by suitable conventional means. In this way the presence of the enzyme (and by extension, for example, a pathogen in the case of an enzyme associated with a particular pathogen) can be detected and/or quantified. Also provided are probes for use in conjunction with the methods described herein. In some embodiments, the probes can release multiple electrochemical molecules upon cleavage by a single enzyme to improve sensitivity.

For example, influenza virus can be detected using a substrate for viral neuraminidase. HIV can be detected using a substrate for reverse transcriptase. *Mycobacterium tuberculosis* can be detected using a substrate for β-lactamase or sulfatase. Other bacteria, such as antibiotic resistance *Staphylococcus aureus* be detected using a substrate for β-lactamase. *Escherichia coli* be detected using a substrate for β-glucuronidase. Carbapenem-resistant Enterobacteriaceae (CRE) can be detected using a substrate for carbapenamases. Bacteria of the *Vibrio* and *Aeronomas* species can be detected using a substrate for lysyl aminopeptidase. *Chlamydia trachomatis* can be detected using a substrate for α mannoside. β-Galactosidase, γ-Glutamyl aminopeptidase, hydroxyproline aminopeptidase, Arginine aminopeptidase, Serine aminopeptidase, glycyl-glycine aminopeptidase, phosphatase, valerate esterase, 4-Methoxyleucine aminopeptidase and glycine aminopeptidase can be used to differentiate between a number of sexually transmitted diseases (STDs), such as N. *Gonorrhoeae*. Beta lactamases are enzymes released by pathogens. They destroy beta lactam antibiotics e.g. penicillin derivatives (penams), cephalosporins (cephems), monobactams, and carbapenems. Glycosidases are produced by a number of pathogens. Fungal biomass in soil can be detected using a substrate for β-N-acetylglucosaminidase or endo 1,4-β-glucanase. Pathogens can be detected using a substrate for peptidase, sulfatase, phosphatase, esterase, or combination thereof.

In some embodiments, the enzyme is indicative of a disease or disorder. For example, white blood cells (WBC) have an enzyme called Leukocyte esterase, which can be detected using N-tosyl-L-alanine as the substrate.

For example, methods for electrochemically detecting an influenza virus in a sample can comprise providing a probe comprising a substrate for a viral neuraminidase covalently linked to an electrochemically active moiety via a glycosidic bond, contacting the sample with the probe under conditions effective for enzymatic cleavage of the glycosidic bond by the viral neuraminidase, and electrochemically detecting the electrochemically active moiety enzymatically cleaved by the viral neuraminidase (e.g., determining the concentration of electrochemically active moiety enzymatically cleaved by the viral neuraminidase via electrochemical means).

By comparison to standard curves, one can determine the concentration of pathogen in the sample and/or the strain of pathogen in the sample. These methods can be used in point-of-care diagnostic assays for the detection of pathogen (e.g., to identify the strain of pathogen infecting a patient in a healthcare setting). The electrochemical methods described herein can also be used to assess the susceptibility of a pathogen to a drug, such as the susceptibility of a virus to an antiviral drug (e.g., a neuraminidase inhibitor such as laninamivir, oseltamivir, zanamivir, or peramivir).

Also provided are probes suitable for use in conjunction with the methods described herein. The probes can include a substrate for a pathogen-specific enzyme, such as viral neuraminidase (e.g., a sialic acid residue), reverse transcriptase, β-lactamase C, β-lactamase, β-glucuronidase, carbapenamases, lysyl aminopeptidase, α mannoside, β-N-acetylglucosaminidase, endo 1,4-β-glucanase, β-Galactosidase, γ-Glutamyl aminopeptidase, hydroxyproline aminopeptidase, Arginine aminopeptidase, Serine aminopeptidase, glycyl-glycine aminopeptidase, phosphatase, valerate esterase, 4-Methoxyleucine aminopeptidase, glycine aminopeptidase, glycosidases, β-N-acetylglucosaminidase, endo 1,4-β-glucanase, or Leukocyte esterase. The substrate can be covalently linked (optionally via a linking moiety) to an electrochemically active moiety (e.g., a glucose residue, an alcohol, etc.) via a glycosidic bond. In some embodiments, the probe can be a multimeric probe that includes a plurality of electrochemically active moieties covalently linked to the substrate by a polyvalent linking moiety.

DESCRIPTION OF DRAWINGS

FIG. 3 illustrates the amperometric response to NA or influenza viruses. (A) Amperometric response of overnight hydrolysis samples by NA or influenza viruses. Applied potential: 0.00V. (B) Amperometric response of hydrolysis samples by H1N1 virus for different time courses.

DETAILED DESCRIPTION

Figure 1:
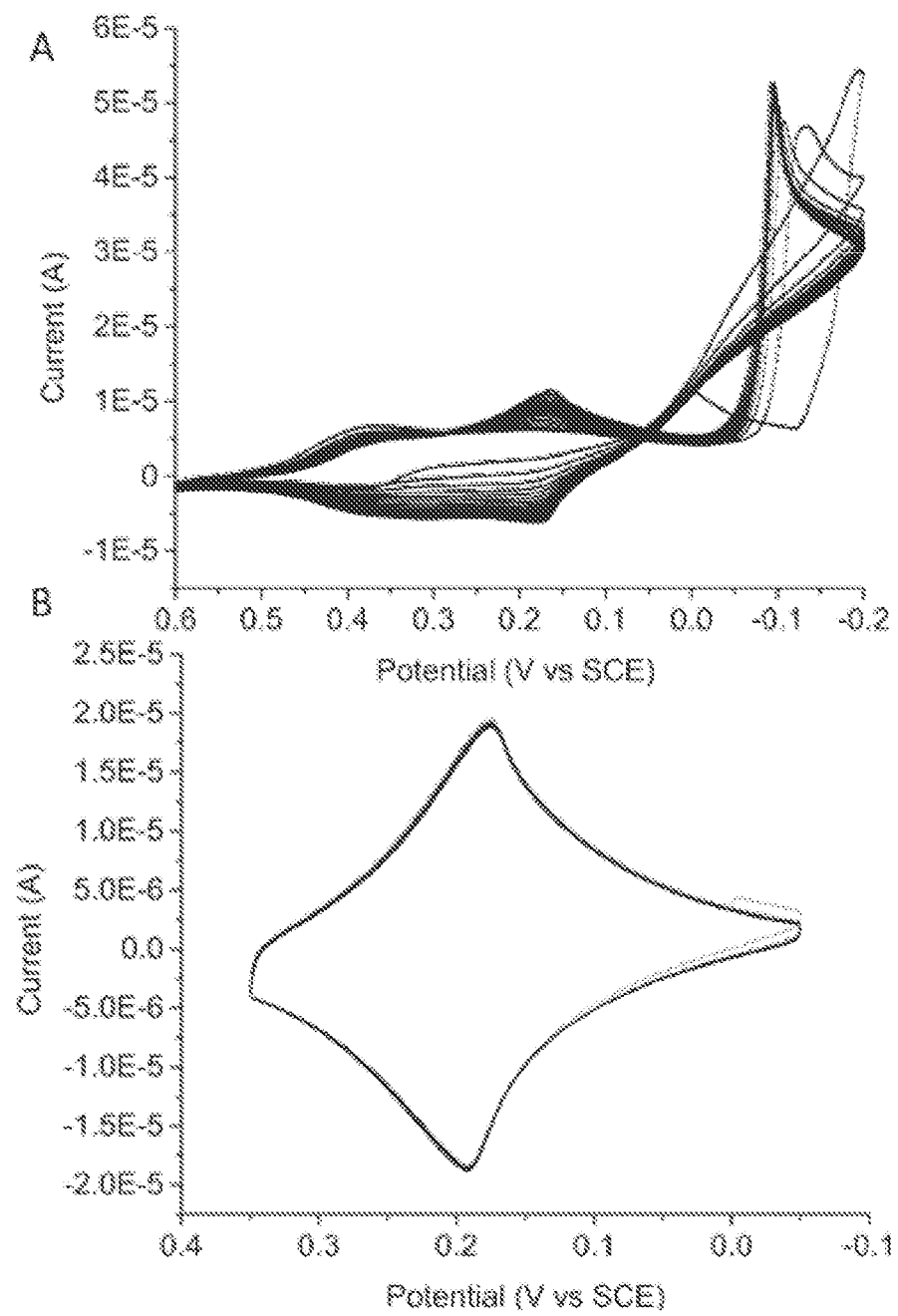
FIG. 1 includes cyclic voltammograms measured during the co-electrodeposition of PB/$Bi_2Se_3$ hybrid films. (A) Cyclic voltammograms of PB/$Bi_2Se_3$ coating on GCE: 30 cycles in a range of −0.2V to +0.6V at a scan rate of 20 mV/s. (B) Cyclic voltammograms of PB/$Bi_2Se_3$ coated GCE in activation buffer: 30 cycles in a range of −0.05V to +0.35V at a scan rate of 50 mV/s.

Provided herein are compositions and methods for the electrochemical detection of enzymes, such as enzymes that are indicative of disease, disorders, or pathogens, such as viruses, bacteria, and fungi, or other disorders. The methods can employ a probe that releases an electrochemically active moiety when exposed to an enzyme present in a sample. The electrochemically active moiety released in the sample can then be monitored using electrochemical techniques. By comparison to standard curves, one can determine the concentration of enzyme in the sample. These methods can be used in rapid diagnostic assays (e.g., in point-of-care and/or laboratory settings) for the detection of disease, disorders, or pathogens.

Methods for electrochemically detecting an enzyme in a sample can comprise providing a probe comprising a substrate for the enzyme covalently linked to an electrochemically active moiety via a bond, such as a glycosidic bond, contacting the sample with the probe under conditions effective for enzymatic cleavage of the bond by the viral the enzyme, and electrochemically detecting the electrochemically active moiety enzymatically cleaved by the enzyme.

Examples of pathogens that can be detected by the disclosed methods, including their enzymes and their fluorescence/chemiluminescence substrates, are given in Table 1A.

detecting *Mycobacterium tuberculosis* (antibiotic resistant and non-resistant strains) rapidly, accurately, and in a cost effective manner. Substrates for 3-lactamase C can be used to detect TB.

*E. coli* is one of the leading causes of food poisoning, especially Shiga toxin producing *E. coli*. *E. coli* contamination in food also has significant economic repercussions. Testing produce, meat, and other sources of food for the presence of *E. coli* rapidly can prevent dissemination and rapid spread of *E. coli* within a population. There are efficient detection methods such as PCR and substrates with fluorogenic probes, however, these techniques are expensive and cannot be used everywhere as they require expensive equipment and trained personnel. Therefore, an efficient, user-friendly, and low-cost method, which can be used by everyone, will help in detecting *E. coli* in food that can be prevented from being spread. Substrates for β-glucuronidase can be used to detect *E. coli*.

Bacteria of *Vibrio* and *Aeronomas* species are mainly associated with sewage. Identification of *Aeronomas* in drinking water is an indication of fecal contamination of drinking water. Existing diagnostic tools, although very efficient and rapid, are not flexible for use in resource poor areas. Therefore, there is a great need for developing rapid diagnostic tests that are robust, cost-effective and can be used in resource poor areas. All family members of Vibrionaceae have a lysyl aminopeptidase which cleaves the L-lysyl-7-amino-4-trifluoromethylcoumarin substrate to produce fluorescence, which is used to detect the pathogen.

TABLE 1A

Pathogens of interest, enzymes and their fluorescent/chemi luminescence substrates.

| Pathogen | Enzyme | Example Substrate |
| --- | --- | --- |
| Influenza | Viral neuraminidase | N-acetylneuraminic acid |
| HIV | Reverse transcriptase | Nucleoside triphosphate |
| *Mycobacterium tuberculosis* | β-lactamase C | Cephalosporin analogue specific to β-lactamase C conjugated to a fluorophore |
| Beta-lactamase containing bacteria (FIG. 6) | β-lactamase | Cephalosporin conjugated to a fluorophore |
| CRE Resistant Enterobacteria | Carbapenemases | Carbapenam-4-methylumbelliferyl |
| *E. coli* | β-glucuronidase | 4-methylumbelliferyl-beta-D-glucuronide |
| *Vibrio cholera, aeromonas* | lysyl aminopeptidase | L-lysyl-7-amino-4-trifluoromethylcoumarin |
| Soil Fungi and bacteria | β-N-acetylglucosaminidase endo 1,4-β-glucanase | 4-methylumbelliferyl N-acetyl-β-D-glucosaminide 4-methylumbelliferyl β-glucan |

According to Centers for Disease Control and Prevention (CDC), approximately one third of the world population is infected with *Mycobacterium tuberculosis* (TB) and it is one of the leading causes of death (approximately 2 million) worldwide. TB is spread through air from person to person and about 9 million people are infected with *Mycobacterium tuberculosis*. The best way to prevent the spread is timely detection of the bacteria and treatment with the appropriate antibiotic. Over usage of the antibiotics has resulted in the evolution of antibiotic resistant tuberculosis, therefore, it is very important that a rapid detection method be used to detect the bacteria and treat it before it can spread to others. There are many detection methods for detecting tuberculosis, such as chest X-ray, tissue culture, tuberculin skin testing, acid-fast staining, PCR, and immunologic testing. These diagnostic methods have their limitations with respect to time, accuracy, sensitivity, and cost. Therefore, there is an immediate need for point-of-care diagnostic method for Methicillin Resistant *Staphylococcus Aureus* (MRSA) is commonly seen in the respiratory tract and on the skin, which is relatively harmless; however in immunocompromised individuals, it poses a high risk for sepsis. MRSA is also a leading cause for necrotizing fasciitis (flesh eating bacteria). Efficient diagnostic tools such as PCR and fluorometric analysis help in detecting antibiotic resistant bacteria, however it is critical to determine the bacterial infection early to administer the correct antibiotics and isolate the patient in hospitals. β-lactamase and coagulase (which is known to cleave a fluorescent substrate, N-t-BOC-val-pro-arg-7-amido-4-methylcoumarin) are present in most strains of MRSA.

Figure 6:
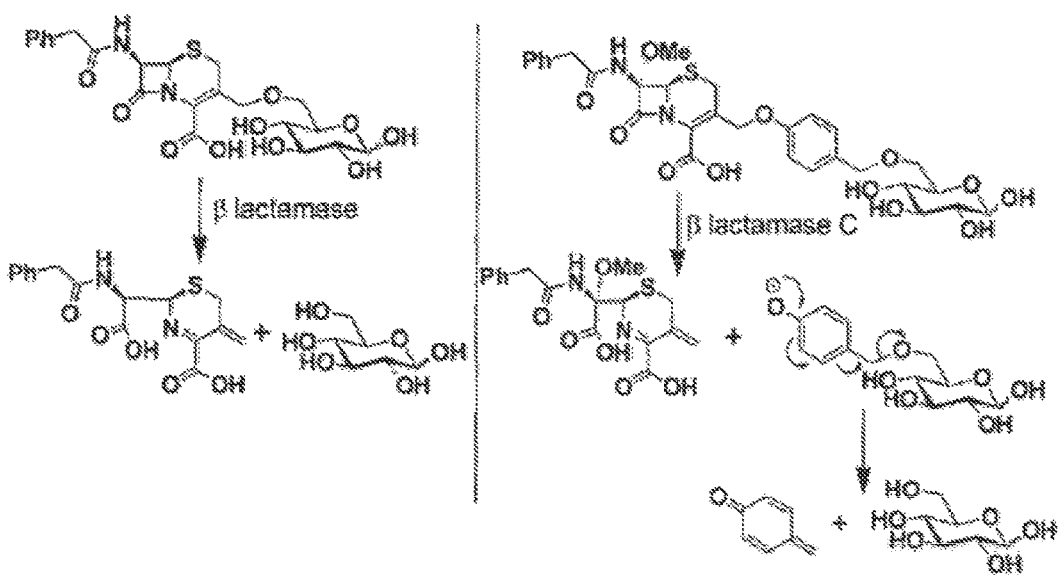
FIG. 6 shows an example of a substrate and cleavage that releases glucose upon exposure to β-lactamase.

Detecting fungal biomass in soil is indicative of enzymatic activity in soil, which is important to study ecological diversity. There are only a few studies focused on studying fungal biomass although fungi contribute significantly to microbial ecology. Fluorometric and quantitative PCR are effective tools in quantifying fungal biomass in the soil to determine the microbial diversity. These diagnostic tests although effective they cannot be used in the field, therefore, there is a need to develop rapid detecting tools that are easy to use and will take as little expertise as possible that can be used in the field in remote areas. Substrates for β-N-acetylglucosaminidase and 1,4-β-glucanase can be used to detect fungi (FIG. 6).

Human immunodeficiency virus (HIV) used to be one of the dreaded diseases in the Western world. With the discovery of antiretroviral drugs, education and good public health policies, the disease is no longer a death sentence. Detection of virus is not a big problem, as antibody based tests are highly sensitive and selective, but they are not sensitive for measuring low copies of the virus. PCR is very efficient at measuring low amounts of the virus, but expensive and not realistic for daily testing. In general, HIV infected patients respond well to antiretroviral therapy, however, constant monitoring of the viral load is very important for physicians to modify the dosing regimen to reduce side effects and limit antiviral resistance. Therefore, there is a pressing need for point of care diagnostics that can quantify viral load and measure drug susceptibility for patient management and improved clinical decisions for this deadly pathogen. Analogues of the substrate for reverse transcriptase (which is nucleoside triphosphate) can be used for detection of HIV. Since antiretrovirals inhibit reverse transcriptase, drug susceptibility can also be measured rapidly and other pathogens such as Herpes simplex virus can also be detected using this substrate.

In some embodiments the pathogen is an influenza virus, which can be detected, for example, using a substrate for neuraminidase. The influenza virus can be any strain of the virus that exhibits a neuraminidase (NA) enzyme on its surface. For example, the influenza virus can be influenza A, influenza B, or influenza C. The influenza virus can be strain (also referred to herein as a subtype or serotype), including but not limited to, H1N1, H2N2, H3N2, H5N1, H7N7, H1N2, H9N2, H7N2, H7N3, H10N7, or H7N9. In some embodiments, the influenza virus can be an influenza strain that expresses an N1, N2, N3, or N7 subtype of influenza NA. In certain embodiments, the influenza virus can be an influenza strain that expresses an N1 or N2 subtype of influenza NA. For detection of influenza, the sample can comprise, for example, a nasal swab or a throat swab collected from a subject (e.g., a human or animal) infected with an influenza virus. The probe for detecting influenza virus can therefore include a substrate for a viral neuraminidase covalently linked to an electrochemically active moiety via a glycosidic bond. The substrate for a viral neuraminidase comprises a sialic acid residue (e.g., N-acetylneuraminic acid).

In some embodiments, the enzyme is indicative of a disease or disorder. For example, white blood cells (WBC) have an enzyme called Leukocyte esterase. When there is a bacterial urinary tract infection or bladder or kidney infection, there is an increase in WBC and the enzyme released in the urine. The enzyme can be detected using substrates that release glucose or galactose or any electrochemically active molecule.

Probes

Provided herein are probes for the electrochemical detection of enzymes, such as enzymes that are indicative of disease, disorders, or pathogens, such as viruses, bacteria, and fungi, or other disorders. As discussed above, the probes can include a substrate for an enzyme of interest covalently bound to an electrochemically active moiety, such that electrochemically active moiety is released upon reaction of the substrate with the enzyme of interest. Optionally, the substrate for the enzyme of interest can be covalently bound to the electrochemically active moiety via a linking moiety. In some embodiments, the probe can be a multimeric probe that includes a plurality of electrochemically active moieties covalently linked to the substrate by a polyvalent linking moiety.

The substrate can include any suitable enzyme substrate. For example, the substrate can comprise a substrate for a pathogen-specific enzyme, such as viral neuraminidase (e.g., a sialic acid residue), reverse transcriptase, 1-lactamase C, β-lactamase, β-glucuronidase, carbapenamases, lysyl aminopeptidase, α mannoside, β-N-acetylglucosaminidase, endo 1,4-β-glucanase, β-Galactosidase, γ-Glutamyl aminopeptidase, hydroxyproline aminopeptidase, Arginine aminopeptidase, Serine aminopeptidase, glycyl-glycine aminopeptidase, phosphatase, valerate esterase, 4-Methoxyleucine aminopeptidase, glycine aminopeptidase, glycosidases, β-N-acetylglucosaminidase, endo 1,4-O-glucanase, or Leukocyte esterase. In certain embodiments, the substrate can be chosen from N-acetylneuraminic acid or a derivative or analog thereof, nucleoside triphosphate or a derivative or analog thereof, cephalosporins or derivatives or analogs thereof, carbapenems or derivatives or analogs thereof, glucuronic acid or a derivative or analog thereof, N-tosyl-L-alanine or a derivative or analog thereof, mannose or a derivative or analog thereof, galactose or a derivative or analog thereof, glucose or a derivative or analog thereof, glucosamine or a derivative or analog thereof, or galactosamine or a derivative or analog thereof.

In some embodiments, the probe is a glucose sensor configured to detect glucose in the range of about 0.001 μM-100 mM, including about 0.011 μM-1,000 μM.

The electrochemically active moiety of the disclosed probes for pathogen detection can be any chemical moiety that is capable of generating an electrochemical signal, directly or by virtue of a mediator, in an electrochemical method such as an amperometric or voltammetric method. In some cases, the electrochemically active moiety can be a moiety capable of existing in at least two distinct redox states. Suitable electrochemically active moieties are known in the art, and include, for example hydroquinone moieties, fluorene moieties, alcohols (e.g., ethanol), and saccharides (e.g., monosaccharides, disaccharides, trisaccharides). In some embodiments, the electrochemically active moiety is chosen from a saccharide such as glucose, galactose, mannose, lactose, or fructose. In some embodiments, the electrochemically active moiety can comprise a $C_1$-$C_6$ alcohol, such as ethanol.

In certain embodiments, the electrochemically active moiety comprises a moiety that is electrochemically silent when not enzymatically cleaved by the enzyme of interest (e.g., a viral neuraminidase). For example, the electrochemically active moiety can comprise a moiety that become electrochemically detectable following enzymatic cleavage by virtue of reaction with an activating molecule. For example, the activating molecule can be an enzyme that reacts with the cleaved electrochemically active moiety to generate a species that is electrochemically detected, either directly or via a redox mediator (e.g., ferrocene, Prussian blue (PB), or potassium hexacyanoferrate). For example, the electrochemically active moiety can comprise glucose or a derivative thereof. Once cleaved, the glucose or glucose derivative can react with glucose oxidase, forming hydrogen peroxide. The hydrogen peroxide can be electrochemically detected directly or by way of a redox mediator such as PB. Such electrochemically active moieties can be referred to as enzymatically-activated electrochemically active moieties.

In some cases, the electrochemically active moiety can optionally be directly bound to the substrate (e.g., via a glycosidic bond). In other embodiments, the electrochemically active moiety can optionally be covalently bound to the substrate via a linking moiety. In some cases, the linking moiety can be a bivalent linking moiety. In these cases, the probe can include a single substrate bound to a single electrochemically active moiety via a linking moiety. In other cases, the linking moiety can be a polyvalent linking moiety. In these cases, the probe can include a single substrate bound to a plurality of electrochemically active moieties via a linking moiety. For example, in some embodiments, the probe can include a single substrate bound to from 2 to 16 electrochemically active moieties (e.g., bound to from 2 to 8 electrochemically active moieties, or bound to from 2 to 4 electrochemically active moieties) via a polyvalent linking moiety. Suitable linking moieties are known in the art.

In certain embodiments, the substrate can comprise N-acetylneuraminic acid or a derivative or analog thereof. For example, in some cases, the probe can be a compound defined by Formula I Formula I

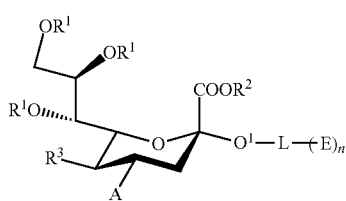

wherein
A is —OH, —OMe, —OC(=O)CH$_3$, —NH$_2$, —NHC(=O)CH$_3$, —NHCH$_2$OH, or —NHC(=NH)NH$_2$;
R$^1$ is, individually for each occurrence, —H, -Me, or —C(=O)CH$_3$;
R$^2$ is —H or -Me;
R$^3$ is —OH, —OMe, —OC(=O)CH$_3$, —NH$_2$, —NHC(=O)CH$_3$, or —NHCH$_2$OH;
n is an integer from 1 to 16;
L is absent or is a linking moiety, wherein when L is absent, O$^1$ is also absent and n is 1; and
E is, individually for each occurrence, an electrochemically active moiety defined by one of the general formulae shown below

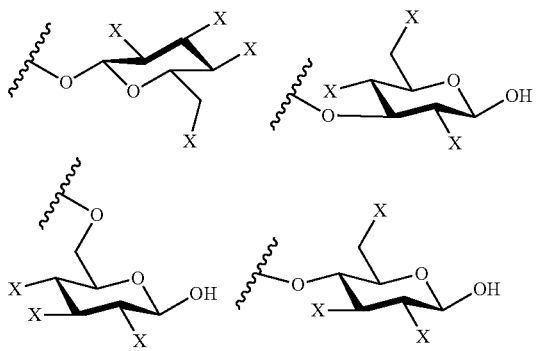

-continued

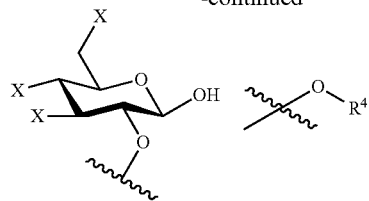

wherein
R$^4$ is a C$_1$-C$_6$ alkyl group, and
X is, individually for each occurrence, —OH, —OMe, —OC(=O)CH$_3$, —F, —CF$_3$, —CH$_2$F, —CHF$_2$, —Cl, —Br, —I, H or sulfonate.

In some embodiments of Formula I, L can be absent. In these embodiments, the probe can be a compound defined by Formula IA Formula IA

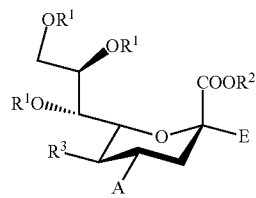

wherein A, R$^1$, R$^2$, R$^3$, and E are as defined above with respect to Formula I.

In some embodiments of Formula I, L is present, and n is at least 1 (e.g., at least 2, at least 3, at least 4, at least 5, at least 6, at least 7, at least 8, at least 9, at least 10, at least 11, at least 12, at least 13, at least 14, or at least 15). In some embodiments of Formula I, L is present, and n is 16 or less (e.g., 15 or less, 14 or less, 13 or less, 12 or less, 11 or less, 10 or less, 9 or less, 8 or less, 7 or less, 6 or less, 5 or less, 4 or less, 3 or less, or 2 or less).

In some embodiments of Formula I, L is present, and n can be an integer ranging from any of the minimum values described above to any of the maximum values described above. For example, n some embodiments of Formula I, L is present, and n can be an integer from 1 to 16 (e.g., an integer from 1 to 8, an integer from 1 to 4, an integer from 2 to 16, an integer from 2 to 8, or an integer from 2 to 4).

In some cases, the L can be a bivalent linking moiety. In these cases, the probe can include a single substrate bound to a single electrochemically active moiety via a linking moiety. Suitable bivalent linking moieties are known in the art. In some embodiments of Formula I, L can be a bivalent linking group chosen from —(CH$_2$)$_q$—, C(=O), C(=S), or S(O)$_q$, where q is 1, or 2. In certain embodiments of Formula I, L can be a bivalent linking group chosen from one of the following

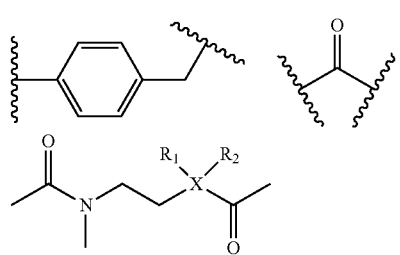

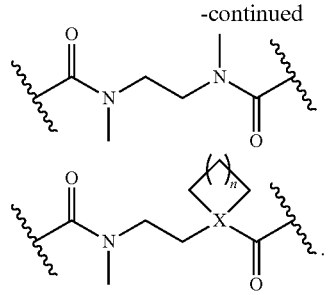

R1, R2 = CH3, C2H5, C(CH3)3, CH(CH3)2
X = C or S
n = 0, 1, 2 or 3

In some cases, the L can be a polyvalent linking moiety. In these cases, the probe can include a single substrate bound to a plurality of electrochemically active moieties via the polyvalent linking moiety. In certain embodiments of Formula I, L can be a polyvalent linking group chosen from one of the following

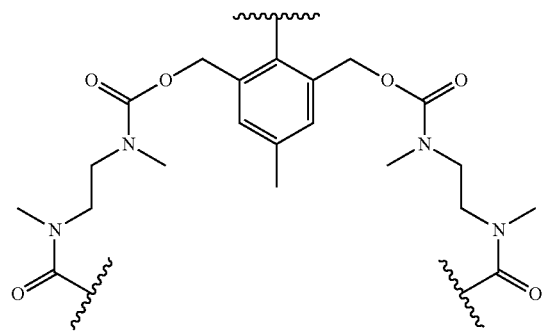

In some embodiments of Formula I and Formula IA, E can comprise a moiety defined by the general formula shown below

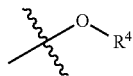

where $R^4$ is a $C_1$-$C_6$ alkyl group. In some of these embodiments, $R^4$ can be a methyl group. In some of these embodiments, $R^4$ can be an ethyl group. In some of these embodiments, $R^4$ can be a propyl group. In some of these embodiments, $R^4$ can be a butyl group. In some of these embodiments, $R^4$ can be a pentyl group. In some of these embodiments, $R^4$ can be a hexyl group. In some of these embodiments, $R^4$ can be a $C_2$-$C_6$ alkyl group. In some of these embodiments, $R^4$ can be a $C_2$-$C_4$ alkyl group.

In some embodiments of Formula I and Formula IA, E can comprise a moiety defined by one of the general formulae below

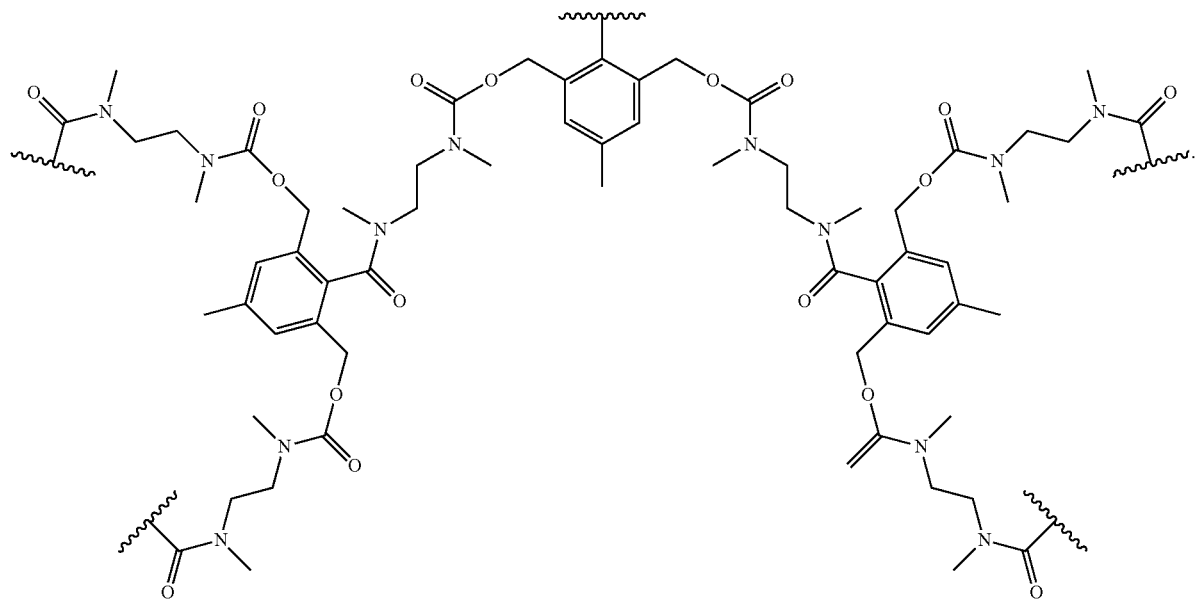

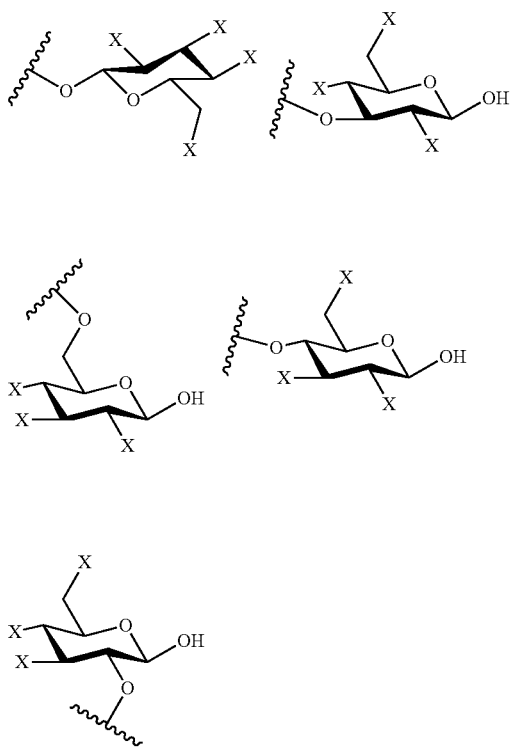

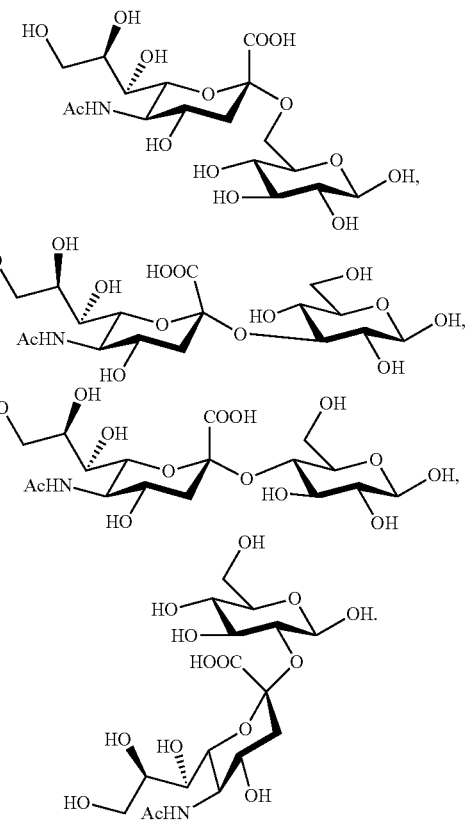

wherein X is, individually for each occurrence, —OH, —OMe, —OC(=O)CH$_3$, —F, —CF$_3$, —CH$_2$F, —CHF$_2$, —Cl, —Br, —I, H or sulfonate. In some of these embodiments, X is, individually for each occurrence, —OH, —OMe, or —OC(=O)CH$_3$. In some of these embodiments, X is, in each occurrence —OH.

In some embodiments of Formula I and Formula IA, X can be, in each occurrence —OH. In certain embodiments, E can comprise a moiety defined the general formula below

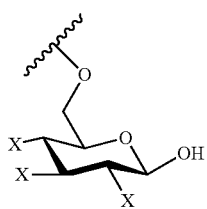

wherein X is, individually for each occurrence, —OH, —OMe, —OC(=O)CH$_3$, —F, —CF$_3$, —CH$_2$F, or —CHF$_2$. In some of these embodiments, X is, individually for each occurrence, —OH, —OMe, or —OC(=O)CH$_3$. In some of these embodiments, X is, in each occurrence —OH.

In some embodiments of Formula I and Formula IA, R$^1$ and R$^2$ are, in each occurrence, —H.

In some embodiments of Formula I and Formula IA, A is —OH.

In some embodiments of Formula I and Formula IA, R$^3$ is —NH$_2$, —NHC(=O)CH$_3$, or —NHCH$_2$OH. In certain embodiments of Formula I and Formula IA, R$^3$ is —NHC(=O)CH$_3$.

In certain embodiments, the probe comprises a compound shown below.

Methods and Kits

Also provided are methods of using the probes described herein. Methods can involve contacting a sample comprising an enzyme with a probe that includes a substrate for the enzyme under conditions effective for enzymatic cleavage of the covalent linkage between the substrate and an electrochemically active moiety. For example in the case of the probes defined by Formula I and Formula IA above, methods can involve contacting a sample comprising a viral neuraminidase (e.g., a sample comprising influenza virus) with a probe defined by Formula I or Formula IA under conditions effective for enzymatic cleavage of the glycosidic bond through which the electrochemically active moiety is bound to the substrate.

For example, the sample can be contacted with (e.g., incubated with) the probe in an aqueous buffer (e.g., a buffer having a pH of from 5.0 to 11, or a buffer having a pH of from 5.5 to 7.5) for a period of time effective to provide for a suitable level of enzymatic cleavage to occur. The incubation time can be varied based on a number of factors, including the chemical structure of the probe (e.g., the reactivity of the glycosidic bond towards enzymatic cleavage), the concentration or potential concentration of enzyme (or virus) in the sample, the identity of the enzyme (e.g., the identity of the influenza virus) present in the sample (e.g., the nature and activity/catalytic turnover of the NA present on the viral surface), etc. For example, the sample and the probe can be incubated for from 1 minute to 24 hours (e.g., from 1 minute to 5 hours, from 1 minute to 1 hour, or from 1 hour to 5 hours).

Once incubated, the cleaved electrochemically active moiety can be electrochemically detected using any suitable method. Suitable methods for electrochemically detecting such moieties are known in the art. For example, in the case of glucose, the amount of glucose in the sample resulting from enzymatic cleavage of the probe can be electrochemically determined using methods known in the art for glucose detection, as described below. By comparison to standard curves, one can determine the concentration of an enzyme (and by extension, the concentration of a pathogen such as influenza) in the sample. In the case of influenza, one can also use these methods to determine the strain of influenza virus in the sample. These methods can be used in point-of-care diagnostic assays for the detection of enzymes (and by extension, pathogens such as influenza).

The electrochemical methods described herein can also be used to assess the susceptibility of a pathogen to an antipathogen drug. This process can involve (i) preparing a first solution comprising the sample and an antipathogen drug; (ii) preparing a second solution comprising the sample; (iii) contacting the first solution and the second solution with the probe under conditions effective for enzymatic cleavage of the bond by the pathogen-specific enzyme; (iv) electrochemically determining the concentration of the electrochemically active moiety enzymatically cleaved by the pathogen-specific enzyme in the first solution and the second solution; and (v) assessing the susceptibility of the pathogen in the sample to the antipathogen drug, wherein a decrease in the concentration of the electrochemically active moiety enzymatically cleaved by the pathogen-specific enzyme in the first solution relative to the second solution indicates the susceptibility of the pathogen in the sample to the antipathogen drug.

By way of example, the methods described herein can be used to assess the susceptibility of an influenza virus to an antiviral drug (e.g., a neuraminidase inhibitor such as laninamivir, oseltamivir, zanamivir, or peramivir). This process can involve collecting a sample, such as a nasal or throat swab from the subject. The sample can then be used to prepare a reference solution (a first solution comprising the sample) and one or more test solutions (each of which comprises the sample and an antiviral drug to be tested). The reference solution and the one or more test solutions are then each contact with a probe under conditions effective for enzymatic cleavage of the glycosidic bond by the viral neuraminidase. Subsequently, the concentration of the electrochemically active moiety enzymatically cleaved by the viral neuraminidase in the reference solution and the one or more test solutions can then be electrochemically determined. By comparing the concentration of the electrochemically active moiety enzymatically cleaved by the viral neuraminidase in the reference solution the concentration of the electrochemically active moiety enzymatically cleaved by the viral neuraminidase in each test solution, one can assess the susceptibility of the influenza virus in the sample to the antiviral drug added to the test solution.

For example, a decrease in the concentration of the electrochemically active moiety enzymatically cleaved by the viral neuraminidase in the test solution relative to the reference solution indicates the susceptibility of the influenza virus in the sample to the antiviral drug added to the test solution. Such methods can be used in clinical settings, in the privacy of a patient's home, or in the field, for example, to select the best antiviral drug for administration to a patient infected with influenza. Such methods can also be used in drug discovery efforts, for example, to screen potential antiviral drugs for activity against an influenza virus.

Also provided are kits for the detection of an enzyme of interest. The kits can include a device for collecting a sample comprising an enzyme of interest (e.g., a needle, swab, or pipette) and a probe comprising a substrate for the enzyme of interest covalently linked to an electrochemically active moiety via a bond that is cleavable by the enzyme of interest. In some cases, the probe can be provided in a buffer solution. In some cases, the kit can further comprise a volume of buffer in which the sample and probe can be combined and reacted. Optionally, the kit can further include a device for detecting the electrochemically active moiety.

For example, in the case of kits for the detection or quantification of influenza, kits can include a device for collecting a sample comprising an enzyme of interest (e.g., a throat swab or a nasal swab or nasopharyngeal wash) from a subject and a probe defined by Formula I or Formula IA above. In some cases, the probe defined by Formula I and Formula IA can be provided in a buffer solution or provided as a solid and buffer can be added to it before running the test In some cases, the kit can further comprise a volume of buffer in which the sample from the subject and the probe defined above can be combined and reacted. Optionally, the kit can further include a device for detecting the electrochemically active moiety.

The examples below are intended to further illustrate certain aspects of the systems and methods described herein, and are not intended to limit the scope of the claims.

EXAMPLES

Example 1: Electrochemical Biosensor for the Detection of Influenza Viruses

Neuraminidase (NA) is one of the two abundant glycoproteins on the surface of influenza viruses. NA functions as an enzyme that hydrolyzes terminal sialic acid from glycans, glycoproteins or glycolipids. The enzymatic activity of NA was exploited to develop an electrochemical biosensor for the detection and quantification of influenza viruses. Specifically, α-2,6-sialylglucose, a substrate that can be recognized and hydrolyzed by viral NA was synthesized. The hydrolysis product of α-2,6-sialylglucose (i.e., D-glucose) can be detected electrochemically.

Introduction

Fluorometric enzyme assays can be used to detect influenza viruses. For example, fluorometric assays for the detection of influenza viruses can employ a fluorogenic reagent, such as 2'-(4-methylumberlliferyl)-α-D-N-acetylneuraminic acid (4-MUNANA), as a NA substrate. In these assays, the NA enzyme cleaves the sialic acid from this substrate and releases the enzymatic hydrolysis product 4-methylumberlliferone, which can be readily measured using by measuring the fluorescence intensity as a function of time and concentration. See Scheme 1 below. The excitation and emission of 4-methylumberlliferone are 365 nm and 450 nm respectively, which are significantly different compared to the excitation and emission of MUNANA (315 nm and 374 nm, respectively). Therefore, the interference of MUNANA can be ignored, and the fluorescence intensity at 450 nm can be used to determine the concentration of 4-methylumberlliferone resulted from the hydrolysis of MUNANA.

Scheme 1.
Cleavage of 4-MUNANA by NA to form 4-methylumberlliferone.

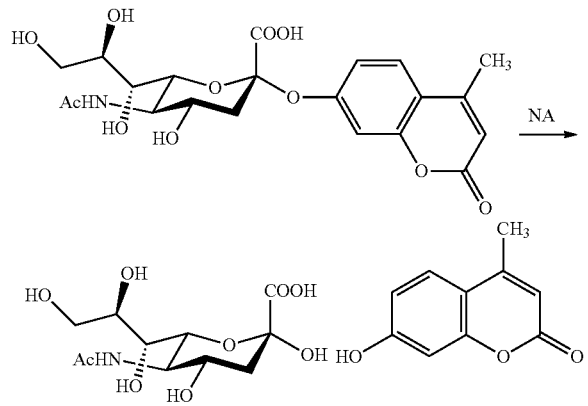

While fluorescence can readily be measured in a laboratory setting, it is very difficult, if not impossible, to use this compound in a primary care setting, where access to a flourometer might not be feasible. Furthermore, optical detection can be subject to misinterpretation if not performed by trained personnel and appropriate laboratory skills using instruments. Also, optical detection methods can have interferences, as mucus from nasal and throat swabs can resonate at the same frequency, thereby interfering with the optical signal. Therefore, non-optical methods, such as electrochemical methods, that can be used to detect influenza viruses offer significant potential advantages, particularly for rapid diagnostic assays (e.g., in point-of-care settings) and/or in conjunction with samples such as nasal swabs.

Electrochemical Biosensors

Electrochemical biosensors offer several advantages over other assay platforms, making them attractive candidates for real world applications, especially in low resource settings. Electrochemical assays can be designed to be label free, which greatly simplifies assay development, avoids possible change in target binding profile caused by labeling and eliminates variations in labeling efficiency. Sensitivity can be very high with small amount of analytes Electrochemical settings are easy to miniaturize and can be engineered into a portable device. Unlike many optically-based assays, turbid media can be used, thus eliminating the need for sample preparation steps. Therefore, clinical samples including urine, saliva, nasal and throat swabs, and blood can be tested directly. Indeed, measuring blood glucose was primarily done using optical methods before electrochemical assays that led to the first glucose meters became available. Today, optical methods for glucose determination have largely been replaced by electrochemical glucose meters.

By using enzymes that react with a released electrochemically active moiety to activate the electrochemically active moiety so as to generate an electrochemically detectable signal (e.g., an enzymatically-activated electrochemically active moiety), the selectivity and sensitivity of the assay can be greatly increased, especially when the sample is complex and/or includes multiple analytes. The response time of electrochemical biosensors is usually very short. For example, seconds of wait time is sufficient using commercial glucose monitors. Low cost and long-term stability also make electrochemical biosensor are further advantages of an electrochemical biosensor.

Generally, electrochemical biosensors utilize the chemical reaction between immobilized biomolecules, usually enzymes, or consumption of electrons to produce measurable electrical property change, such as current, conductance, potential and ionic strength. A basic electrochemical setting consists of three electrodes: working electrode, reference electrode and counter electrode. Suitable electrodes can be made from platinum, gold and carbon, since they are inert, biocompatible, highly conductive and readily modified.

Electrochemical biosensors have broad applications in clinical diagnosis, covering a variety of metabolites such as glucose, lactate, cholesterol and urea, etc. Other targets include antigens, antibodies and cancer markers. In recent years, electrochemical sensing has been extended to more complex targets: pathogens, e.g., E. coli and HIV virus, by targeting at DNA or RNA. Among these applications, electrochemical sensing of glucose biosensor is the most successful example as it is currently being used by pre-diabetic and diabetic patients to monitor blood glucose concentration.

Electrochemical Detection of Glucose

Diabetes is one of the most common threats of human health. According to American Diabetes Association, there are 25.8 million people who have diabetes in the United States, along with 79 million people with pre-diabetes. Blood glucose level is the indicator of diabetes and needs to be monitored closely. If blood glucose is between 70-120 mg/dl, patients are not diabetic. If the glucose level is above 126 mg/dl from the fasting plasma glucose test, or 200 mg/dl from the oral glucose tolerance test, patients are considered diabetic. Therefore a lot of progress has been made towards the development of a user friendly, portable glucose biosensor and these sensors are commercially available.

The principle of most glucose biosensors is that glucose oxidase (GOD) converts D-glucose into D-gluconic acid with the presence of oxygen and also produces hydrogen peroxide, as shown in the following reaction:

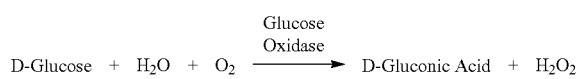

The enzyme provides the specificity needed for eliminating false positives or negatives.

While hydrogen peroxide can be readily detected using an electrochemical setup, the oxidation of hydrogen peroxide is usually over +600 mV with standard electrodes, which is high enough to oxidize many other electroactive compounds present in biological samples. Moreover, the response of the biosensor is highly susceptible to oxygen concentration in the media thus affect the reproducibility of the assays a great deal. Therefore, redox mediators such as ferrocene, Prussian blue (PB), potassium hexacyanoferrate are widely used due to the ability of significantly decreasing the large overvoltage required for the oxidation or reduction of hydrogen peroxide. An alternative reaction is shown below:

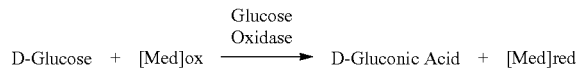

where [Med] represents a mediator. Among several available mediators, ferrocene and its derivatives are the most widely used class of mediators in the development of chemically modified electrodes due to the following features: relatively low molecular mass, rapid responses to many electroactive substances, being pH-independent, stability in both oxidized and reduced forms at low potential and having fast electron transfer. However, ferrocene usually has to be covalently linked to chitosan in order to prevent leakage, a common problem seen in low molecular weight materials.

Ferrocene functions as artificial electron acceptor/donor or mediator by taking place of oxygen in the enzymatic reaction. In the case of glucose oxidase, two electrons are first transferred from glucose to FAD to form $FADH_2$, and then to ferrocene and convert it to the reduced form, which can be oxidized at the electrode surface and produce a current. The current is directly proportional to the glucose concentration in solution. The reaction is shown below.

$$\text{Glucose+GOD(FAD)}\rightarrow\text{gluconolactone+GOD}(\text{FADH}_2)$$

$$\text{GOD(FADH}_2\text{)+2Fc}^+\rightarrow\text{GOD(FAD)+2Fc+2H}^+$$

$$\text{2Fc}\rightarrow 2e^-\text{+2Fc}^+$$

GOD: Glucose oxidase; FAD: Flavin adenine dinucleotide; $FADH_2$: reduced form of FAD; Fc: Ferrocene. $Fc^+$: oxidized form of ferrocene.

Prussian blue (PB) is also called “artificial peroxidase”, which can catalyze hydrogen peroxide electrochemical reaction at lower potential, thus chosen as another candidate of mediators. The catalytic mechanism of PB is shown as following:

$$\underset{\text{Prussian blue}}{\text{KFe}^{(III)}[\text{Fe}^{(II)}\text{CN}_6]} + e^- + \text{K}^+ \longleftrightarrow \underset{\text{Prussian white}}{\text{K}_2\text{Fe}^{(II)}[\text{Fe}^{(II)}\text{CN}_6]} \quad (1)$$

$$\underset{\text{Prussian white}}{2\text{K}_2\text{Fe}^{(II)}[\text{Fe}^{(II)}\text{CN}_6]} + \text{H}_2\text{O}_2 + 2\text{H}^+ \longleftrightarrow \underset{\text{Prussian blue}}{2\text{KFe}^{(III)}[\text{Fe}^{(II)}\text{CN}_6]} + 2\text{H}_2\text{O} + 2\text{K}^+ \quad (2)$$

Since the first enzyme-based commercial glucose biosensor came to the market, enormous effort has been devoted to develop enzyme immobilization techniques suitable to immobilize GOD. There're three major techniques including adsorption, covalently cross-linking and entrapment. Adsorption is the simplest method but least stable due to the fast desorption of the enzyme. Cross-linking enzyme to a membrane or coating layer greatly increases stability but on the cost of possible enzymatic activity loss due to the change of enzyme conformation. Moreover, when utilizing Shiff's base formation, leaching of enzyme can still occur due to reversibility of the reaction. Entrapment using carbon paste or polymers increases the lifetime of enzyme-modified electrode, however, utilization of the entrapped enzyme is very limited.

An attractive enzyme immobilization method can afford the enzyme in a form that can be easily handled and also help maintain enzyme activity in long term. Sol-gel coating techniques can readily produce the desired immobilization and coating of the electrodes. These coating techniques utilize sol-gel-derived materials to embed enzyme onto electrodes, which possesses the following features: physically rigid, chemically inert and thermally stable in both aqueous and organic solution.

Chitosan (CS), a complex polysaccharide comprising of repeating units of randomly distributed 3- (1,4)-linked D-glucoseamine and N-acetyl-D-glucoseamine units can be used as a polymer for purposes of enzyme immobilization. Chitosan can be used in enzyme immobilization due to its excellent film-forming ability, biocompatibility, well mechanical strength, cheapness and susceptibility to chemical modification. Chitosan becomes insoluble when the pH is above 6.3, which greatly increases the stability of immobilized enzyme layer, thus the assay for detecting glucose should be done under neutral or weak basic condition.

Probes

To effect the electrochemical detection of influenza viruses, probes were developed that can generate a measurable electrical signal upon exposure to an influenza virus. The probes include a sialic acid residue bound to an electrochemically active moiety via a glycosidic bond. The electrochemically active moiety can be selected so as to be electrochemically silent when bound to the sialic acid; however, once cleaved from the sialic acid by an NA present on the surface of an influenza virus, the electrochemically active moiety can generate an electrochemical signal that can easily be measured.

α-2, 6-sialylglucose was targeted for initial investigation. The α-2,6-sialylglucose contains terminal sialic acid, which can be recognized and hydrolyzed by viral neuraminidase or intact influenza viruses. The intact probe itself will not result in electrochemical signal, however, the hydrolysis product β-D-glucose can be detected electrochemically as described above. The presence of electrochemical signal indicates whether an unknown sample contains influenza viruses. Moreover, when the glucose concentration in the hydrolysis sample falls in the linear range of detection, the amount of glucose can be quantified. Thus, the NA unit, defined as the ability of hydrolyzing α-2, 6-sialylglucose in given time can be measured.

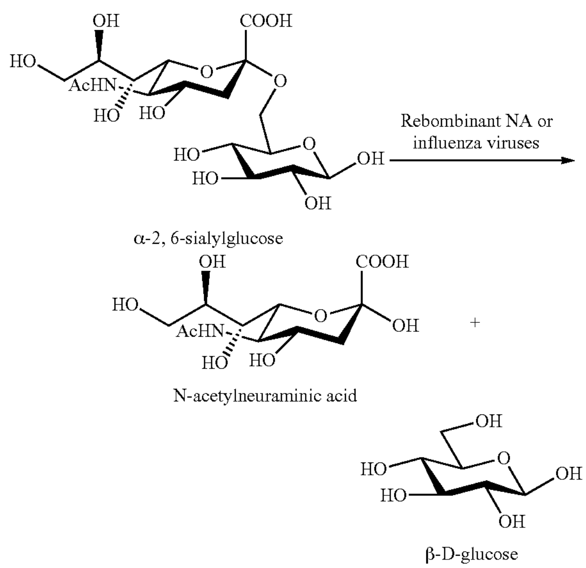

α-2, 6-sialylglucose

N-acetylneuraminic acid

β-D-glucose

Commercial glucose sensors are designed to monitor human blood sugar range, which lies between 70-180 mg/dL or 3.9-10 mM (non-diabetics: 70-130 mg/dL; diabetics: less than 180 mg/dL). In addition, glucose is already present in the blood for detection. In the proposed system for the detection of influenza, the aim is to detect influenza virus in a sample, such as a nasal or throat swab, which doesn't have any glucose or in which glucose is present in extremely low or negligible amounts. Rather, the probe will be introduced to the sample containing the virus, leading to the production of glucose. The concentration of glucose will be dependent on the amount of probe added, the concentration of the virus, the nature and activity/catalytic turnover of the NA (e.g., N1 vs. N2 vs. N7) present on the viral surface, etc. Therefore, though sensors operating on the same principles as commercial glucose sensors can be used in conjunction with the methods and probes described herein, the glucose sensors are configured to exhibit a sensory response to a wider range of glucose concentrations. They may also have a lower limit of detection than commercial systems.

For purposes of the methods described herein, a glucose sensor configured to detect glucose in the range of 0.011-1,000 µM was prepared. A suitable sensor could be prepared using a procedure that coelectrodeposits a PB/$Bi_2Se_3$ hybrid film onto an electrode surface and incorporates GOD by CS immobilization. The reported detection limit of glucose using this sensor was 3.8 µM. Also, the modified surface was stable at mild acidic condition, consistent with the maximum activity of viral NA.

Experimental

Synthesis of "Masked" Electrochemical Substrates
Abbreviations

Di-isopropyl ethylamine, DIPEA; N, N Dimethyl formamide, DMF; Ethyl acetate, EtOAc; Acetonitrile, $CH_3CN$; Dichloromethane, DCM; triethylamine, TEA; Triflic acid, TfOH; Methanesulfonic acid, MsOH; Dimethylaminopyridine, DMAP; Thin layer chromatography, TLC; tert-butyldimethylsilyl chloride, TBS-Cl; Benzyl alcohol, BnOH; Sodium hydride, NaH; tert-Butyldimethylsilyl chloride, TBSCl; benzyl bromide, BnBr; Sulfuric acid, $H_2SO_4$; Methanol, MeOH; Room temperature, rt; benzyl alcohol, BnOH; Sodium bisulfate, $Na_2S_2O_3$; Dichloromethane, DCM; Sodium sulfate, $NaSO_4$; N-Iodosuccinimide, NIS; Sodium methoxide, NaOMe; palladium hydroxide, Pd(OH)$_2$; Hydrogen gas, $H_2$; Sodium hydroxide, NaOH; water, $H_2O$; Nuclear Magnetic Resonance Spectroscopy, NMR; High resolution mass spectroscopy, HRMS; Electrospray ionization, ESI.

at rt and the reaction mixture was heated at 85° C. for 7 hours. After completion of reaction as determined by TLC, the solvent was removed under reduced pressure and the crude compound was purified by flash column chromatography eluting DCM:MeOH (9:1) to afford the compound 2 (1.91 g, 85% yield). To a solution of compound 2 (1 g, 3.70 mmol) in 10 mL pyridine, TBSCl (0.85 g, 5.55 mmol) was added, followed by addition of DMAP (0.04 g, 0.37 mmol). The reaction mixture was stirred for 12 hours at rt. Pyridine was removed under reduced pressure, and compound 3 was used directly for the next reaction without further purification. To the stirred suspension of NaH (0.89 g, 18.5 mmol, 50% suspension prewashed with dry hexane 2×10 mL) in anhydrous DMF (10 ml), a solution of crude compound 3 in DMF (10 ml) at 0° C. and reaction mixture was stirred under argon atmosphere for 30 min. BnBr (2.25 ml, 18.5 mmol) was added in a dropwise manner and reaction mixture was stirred for 3 hours. After completion of reaction, as determined by TLC, the reaction mixture was diluted with EtOAc and then washed with water and brine. The organic layer was dried over $NaSO_4$ and concentrated under reduced pressure to obtain compound 4, which was used in the next step without further purification. To a stirred solution of 4 in MeOH (20 ml) $H_2SO_4$ (1 M solution in MeOH, 1 ml) was added. The reaction mixture was stirred at room temperature and the reaction progress was monitored by TLC using two solvent systems: EtOAc-hexane (1:9) and EtOAc-hexane (1:1). After completion of reaction as judged by TLC, the reaction mixture was diluted with EtOAc and washed with saturated $NaHCO_3$ and brine. The organic layer was dried over $NaSO_4$ and concentrated under reduced pressure. The compound was purified by flash chromatography to give 5a (0.60 g, 30%) and 5p (0.40 g, 20% over 3 steps).

Compound 5α: $^1$H NMR (400 MHz, CDCl$_3$): δ 7.49-7.30 (m, 20H), 5.03 (d, J=10.9 Hz, 1H), 4.89 (dd, J=18.0, 10.9 Hz, 2H), 4.83 (d, J=3.6 Hz, 1H), 4.76-4.69 (m, 3H), 4.59 (d, J=4.7 Hz, 1H), 4.56 (d, J=4.7 Hz, 1H), 4.09 (t, J=9.3 Hz,

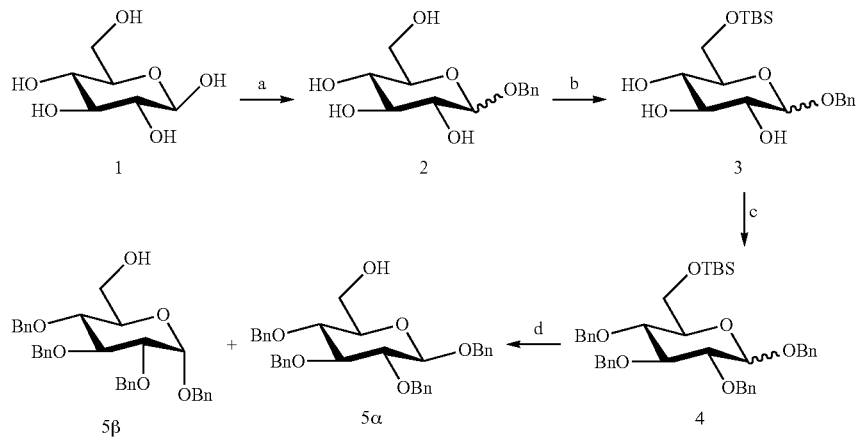

Scheme 2. Synthesis of Compound 5α/5β.

Reagents and conditions: a) BnOH, Sulfamic acid, 85° C., 7 h; b) Pyridine, TBSCl, DMAP, rt, overnight; c) NaH, BnBr, DMF, 0° C.-rt, 3 h; d) 1M H$_2$SO$_4$, MeOH, rt, 1 h.

Synthesis of Compound 5α/5β: 1,2,3,4 Tetrabenzyl α, β D-Glucopyranoside

To the stirred suspension of D-glucose (1, 1.50 g, 8.33 mmol) and excess of BnOH, sulfamic acid (1 ml) was added 1H), 3.80-3.72 (m, 3H), 3.57 (d, J=9.1 Hz, 1H), 3.52 (dd, J=9.5, 3.6 Hz, 1H). $^{13}$C NMR (100 MHz, CDCl$_3$): δ 138.88, 138.20, 137.15, 128.55, 128.48, 128.45, 128.13, 127.98, 127.94, 127.86, 127.65, 95.65, 82.00, 80.11, 77.50, 75.76, 75.14, 73.12, 71.09, 69.31, 61.83. HRMS (ES$^+$): Calcd for C$_{34}$H$_{36}$O$_6$Na [M+Na]$^+$ 563.2410, found 563.2409.

Compound 5β: $^1$H NMR (400 MHz, CDCl$_3$): δ 7.39 (d, J=27.0 Hz, 20H), 5.05-4.96 (m, 3H), 4.90 (dd, J=21.4, 10.9 Hz, 2H), 4.83-4.76 (m, 2H), 4.76-4.68 (m, 2H), 4.64 (d, J=7.7 Hz, 1H), 3.94 (d, J=12 Hz, 1H), 3.82-3.70 (m, 2H), 3.65 (t, J=9.3 Hz, 1H), 3.56 (t, J=8.5 Hz, 1H), 3.43 (d, J=9.7 Hz, 1H). $^{13}$C NMR (100 MHz, CDCl$_3$): δ 138.59, 138.38, 138.05, 137.35, 128.55, 128.49, 128.46, 128.45, 128.43, 128.19, 128.12, 128.01, 127.94, 127.76, 127.71, 102.90, 84.61, 82.41, 77.63, 75.76, 75.16, 75.12, 75.04, 71.70, 62.10. HRMS (ES$^+$): Calcd for C$_{34}$H$_{36}$O$_6$Na [M+Na]$^+$ 563.2410, found 563.2409.

4.97 (d, J=10.8 Hz, 1H), 4.86-4.78 (m, 3H), 4.76 (d, J=6.1 Hz, 1H), 4.73-4.65 (m, 2H), 4.56 (dd, J=15.0, 12.2 Hz, 2H), 4.26 (dd, J=12.4, 2.7 Hz, 1H), 4.20 (dd, J=10.8, 4.5 Hz, 1H), 4.14 (d, J=7.2 Hz, 1H), 4.08-3.98 (m, 2H), 3.98-3.84 (m, 2H), 3.73 (s, 3H), 3.66 (dd, J=11.2, 9.4 Hz, 1H), 3.60 (d, J=9.4 Hz, 1H), 3.58-3.52 (m, 1H), 3.49 (dd, J=10.6, 2.0 Hz, 1H), 2.94 (dd, J=12.1, 3.4 Hz, 1H), 2.49 (s, 3H), 2.15 (s, 3H), 2.12-2.06 (m, 1H), 2.04 (s, 3H), 1.81 (s, 3H). $^{13}$C NMR (100 MHz, CDCl$_3$): δ 171.88, 170.64, 169.95, 169.92, 168.46, 153.65, 138.85, 138.45, 138.21, 137.12, 128.40, 128.35, 128.04, 127.93, 127.88, 127.78, 127.57, 99.29, 95.51, 81.90, 79.62, 77.52, 75.77, 75.28, 75.05, 74.91, 73.03, 71.43, 69.93, 69.09, 68.44, 64.71, 62.83, 59.15,

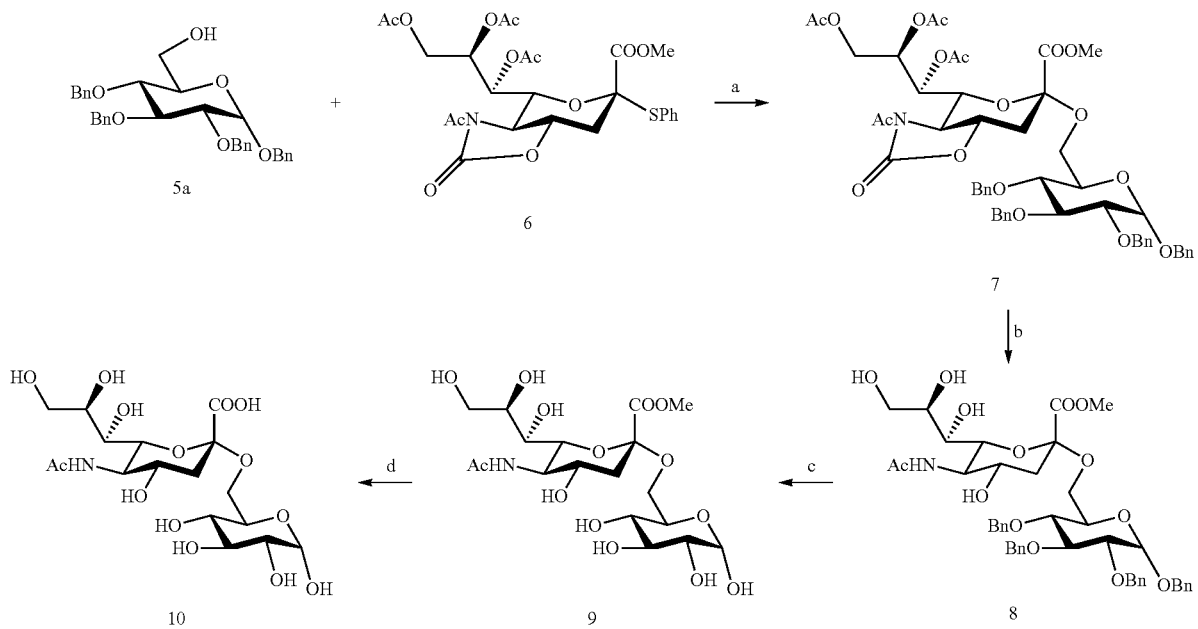

Scheme 3. Synthesis of Compound 10.

Reagents and conditions: a) TfOH, NIS, DCM, -40° C., 1 h, 40%; b) NaOMe, MeOH, rt, 30 min.; c) Pd(OH)$_2$/C/H$_2$, ethanol, rt, 12 h; d) NaOH, rt, 3 h, 95% (over three steps)

Synthesis of Compound 7: Benzyl [methyl (5-acet-amido-7,8,9-tri-O-acetyl-5-N,4-O-carbonyl-3,5-dide-oxy-D-glycero-D-galacto-non-2-ulopyranosyl)onate]-(2→6)-2,3,4-tri-O-benzyl-α-D-glucopyranoside To the stirred solution of 6 (synthesized separately as described in reference, Crich, D.; Li, W. *J. Org. Chem.* 2007, 72 (7), 2387-2391), (0.20 g, 0.35 mmol) and 5a (0.23 g, 0.42 mmol) in anhydrous DCM (4 ml) under an argon atmosphere at -40° C., NIS (0.19 g, 0.84 mmol) was added followed by TfOH (0.52 ml, 0.35 mmol, 10% in anhydrous DCM). The reaction mixture was stirred at -40° C. for -1 hour. After completion as determined by TLC, the reaction was quenched using TEA and warmed to rt over the course of 1 hour. The mixture was diluted with DCM (10 ml), washed with aqueous Na$_2$S$_2$O$_3$ solution, dried over Na$_2$SO$_4$ and concentrated under reduced pressure. The residue was purified by flash silica gel column chromatography eluting with hexane:EA (7:3) to afford the compound 7 (0.14 g, 40%) as a white solid.

$^1$H NMR (400 MHz, CDCl$_3$): δ 7.45-7.26 (m, 20H), 5.58 (dd, J=8.9, 1.7 Hz, 1H), 5.45 (ddd, J=8.5, 6.1, 2.5 Hz, 1H), 52.97, 36.65, 24.70, 21.17, 20.78, 20.57. HRMS (ESI$^+$): Calcd for C$_{53}$H$_{59}$NO$_{18}$Na [M+Na]$^+$ 1020.3630, found 1020.3629.

Compound 10. 5-acetamido-3,5-dideoxy-D-glycero-α-D-galacto-non-2-ulopyranosylonate-(2→6) α-D-glucopyranoside Compound 7 (0.06 g, 0.06 mmol) was dissolved in MeOH (8 mL) and treated with a 30% solution of NaOMe (0.2 ml, in MeOH) and stirred at rt for 1 hour. The solution was neutralized with Amberlite IR-120 H$^+$ resin, filtered and concentrated under reduced pressure to yield a white powder. Next, this compound and Pd(OH)$_2$ (10 mg) in EtOH (2 ml) was stirred for 12 hour at rt under H$_2$ gas at 1 atmosphere pressure. After completion of reaction as determined by TLC, the reaction mixture was filtered using a pad of celite. The celite pad was washed with 10 ml of EtOH and the combined solutions was concentrated under reduced pressure to yield a white solid. This compound was treated with NaOH (0.05 N, 3 ml) and reaction was stirred for 4 hours. After completion of reaction as judged by TLC using the solvent system, DCM: MeOH:NH$_4$OH (8:2:1), the reaction mixture was neutralized using H$^+$ resin, filtered and concentrated in vacuo. The final compound, 10, was purified using P-2 gel column to furnish compound 1 (0.026 g, 93% over three steps).

$^1$H NMR (400 MHz, D$_2$O): δ 5.12 (d, J=4.0, 1H), 4.54 (dd, J=7.8, 1.4 Hz, 1H), 4.07-3.86 (m, 2H), 3.84-3.68 (m, 6H), 3.66-3.53 (m, 4H), 3.52-3.31 (m, 3H), 3.17 (t, J=8.0 Hz, 1H), 2.58 (dd, J=8.0, 4.0 Hz, 1H), 1.95 (s, 3H), 1.71 (td, J=12.0, 4.0 Hz, 1H). $^{13}$C NMR (100 MHz, D$_2$O): δ 177.00, 175.02, 95.96, 92.07, 75.59, 74.38, 73.99, 72.62, 71.44, 69.98, 69.44, 68.23, 67.97, 62.71, 51.82, 39.80, 22.03. HRMS (ES$^+$): Calcd for C$_{17}$H$_{29}$NO$_{14}$Na [M+Na]$^+$ 494.1486, found 494.1497.

Fabrication of a PB/Bi$_2$Se$_3$ Mediated Glucose Biosensor

A glassy carbon electrode (GCE) was polished and cleaned thoroughly prior to the modification following standard procedures. Briefly, the GCE was polished on a nylon-polishing pad using alumina micropolish powder of different particle size, following the sequence of 1.0 m, 0.3 μm and 0.05 Lm with rinses in between. The polished GCE then was washed ultrasonically in HNO$_3$ (50% in H$_2$O), ethanol (50% in H$_2$O) and DI H$_2$O. The clean surface of GCE was dried under continuous airflow.

A PB solution was prepared by dissolving K$_3$Fe(CN)$_6$ and FeCl$_3$ in 10 mM HCl containing 0.1M KCl, reaching a final concentration of 2 mM. Electrodepositing Bi$_2$Se$_3$ solution was a mixture of 2 mM Bi(NO)$_3$ and 3 mM SeO$_2$ in diluted nitric acid (14% in H$_2$O). Co-electrodepositing solution was obtained by mixing PB solution and Bi$_2$Se$_3$ solution in the ratio of 2:1. Activation solution was 0.1M KCl in 10 mM HCl. 0.5% CS solution was prepared by dissolving 50 mg CS in 10 ml of 2% acetic acid with sonication. 2 mg of glucose oxidase was mixed with 50 ul of CS solution and pipetted gently to obtain a homogenous mixture. All solutions were prepared fresh daily.

The hybrid film of PB/Bi$_2$Se$_3$ was electrodeposited on the GCE surface by cyclic voltammetry (CV) with a scan range of −0.2V to +0.6V and scan rate of 20 mV/s for 30 cycles. The modified electrode was rinsed with DI H$_2$O and activated in activation solution by CV with a scan range of −0.05V to +0.35V and scan rate of 50 mV/s for 30 cycles, followed by rinse and air-dry procedure. The electrode was further modified with glucose oxidase by dropping 10 μl of GOD-CS mixture onto the electrode surface and then dried with airflow. Modified electrode was soaked in PBS buffer (pH=6.86) and stored at 4° C. when not in use.

Amperometric Measurement of Glucose Standard Solution

A serial 2-fold dilution of D-(+)-glucose solution in 25 mM PBS containing 0.1M KCl (pH=6.8), from 800 μM to 6.25 μM, was prepared to determine the linear measurement range of GOD modified PB/Bi$_2$Se$_3$/GCE. Current was measured continuously in 200 seconds with applied potential of 0.0V. The end point current was recorded to establish the standard curve.

Hydrolysis of Sialylglucose by Recombinant NA or Intact Influenza Virus

A 10 mM sialylglucose stock solution was diluted in 10 mM of NH$_4$OAc buffer (pH=5.68) and recombinant NA or live influenza virus suspension was added. The final concentration of sialylglucose was adjusted to 1 mM. The substrate/NA or virus mixture was incubated at 37° C. NA or influenza virus was removed by filtration using Amicon-ultra centrifugal filter with a 300K cut-off membrane. The glucose concentration then was measured amperometrically following the same procedure as the glucose standard solution.

Results and Discussion

Co-Electrodeposition of PB/Bi$_2$Se$_3$ Hybrid Films by Cyclic Voltammetry (CV)

Cyclic voltammograms were employed to obtain stable PB/Bi$_2$Se$_3$ hybrid films. In comparison to pure PB film, the nanostructure of PB particles that are co-deposited on the electrode surface was more compact and smaller in size. Under scanning electron microscope (SEM), the pure PB film showed serious aggregation, which enlarged the effective particle size furthermore; on the contrary, a much smoother surface without obvious defect was observed when PB was co-electrodeposited. In addition, the alkaline-resistant Bi$_2$Se$_3$ particles can prevent PB from leaching under mild basic condition, thus expand the pH range of running assays. The CV technique allows dissolution and electrodeposition film occur alternatively during the oxidation and reduction process, as a result, the deposited film is compact and can firmly adherent to the electrode surface.

The cyclic voltammograms of PB/Bi$_2$Se$_3$ hybrid film co-deposition are shown in FIG. 1, panel A. Two pairs of redox peaks and one irreversible peak are observed as expected. The redox pair at around +0.21V corresponds to PB, while the pair at 0.40V can be attributed to nitric acid in the coating solution. The peak at −0.11V is attributed to the formation of Bi$_2$Se$_3$, resulting from reduction of H$_2$SeO$_3$. The reaction equation is shown below.

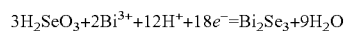

$$3H_2SeO_3 + 2Bi^{3+} + 12H^+ + 18e^- = Bi_2Se_3 + 9H_2O$$

The PB redox peak pair increases gradually as the cycle of scan increases, indicating the continuous growth of PB layer. 30 cycles of scan has been found to be suitable, resulting in a PB layer with suitable thickness that provides sufficient stability as well as sensitivity. 50 cycles or more of scan resulted in a much thicker PB layer, but reduced the sensitivity in detecting hydrogen peroxide. The scan rate is also a factor in the co-electrodeposition process. Although a higher scan rate accelerates the coating process, the resulting deposited PB layer is less compact and unstable. The PB layer formed at a scan rate of 100 mV/s decomposes with only a few assays in KCl solution. On the contrary, a scan rate of 20 mV/s results in a much more stable PB layer, which lasts for more than 30 assays. The activation step helps stabilize the current in cyclic voltammetric run in KCl solution. The cyclic voltammogram is shown in FIG. 1, panel B.

Amperometric Detection of Glucose

Figure 2A:
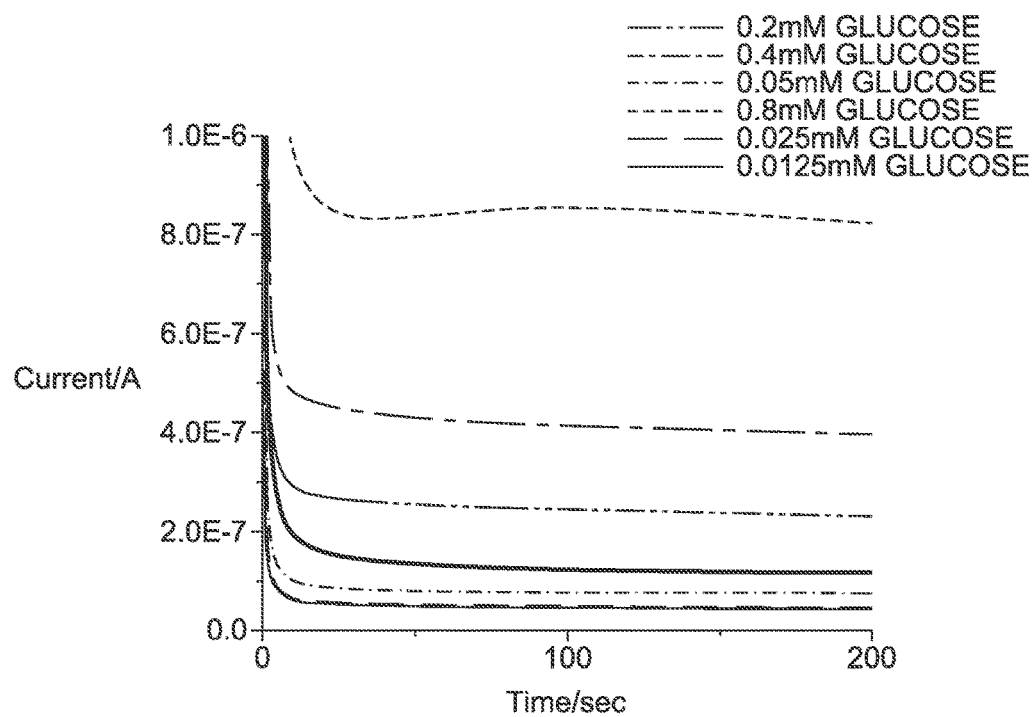
FIG. 2 illustrates the amperometric response of a PB/$Bi_2Se_3$ coated GCE at different concentration of glucose. (A) Amperometric response of PB/$Bi_2Se_3$ coated GCE at different concentration of D-(+)-glucose. Applied potential: 0.00V. (B) Standard curve generated by linear regression. The insert is a zoomed region from 0-100 uM.
Figure 2B:
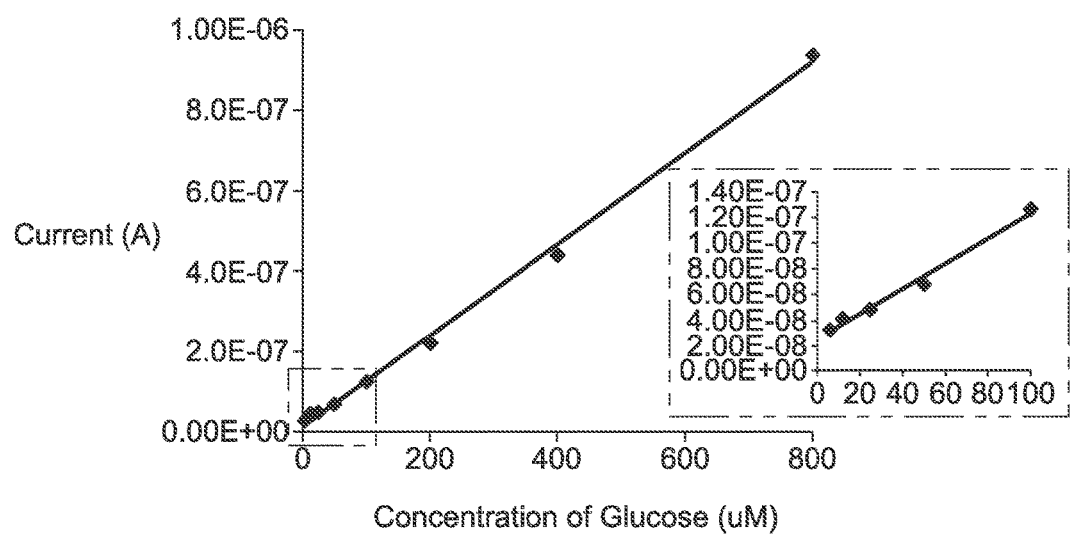
Figure 4A:
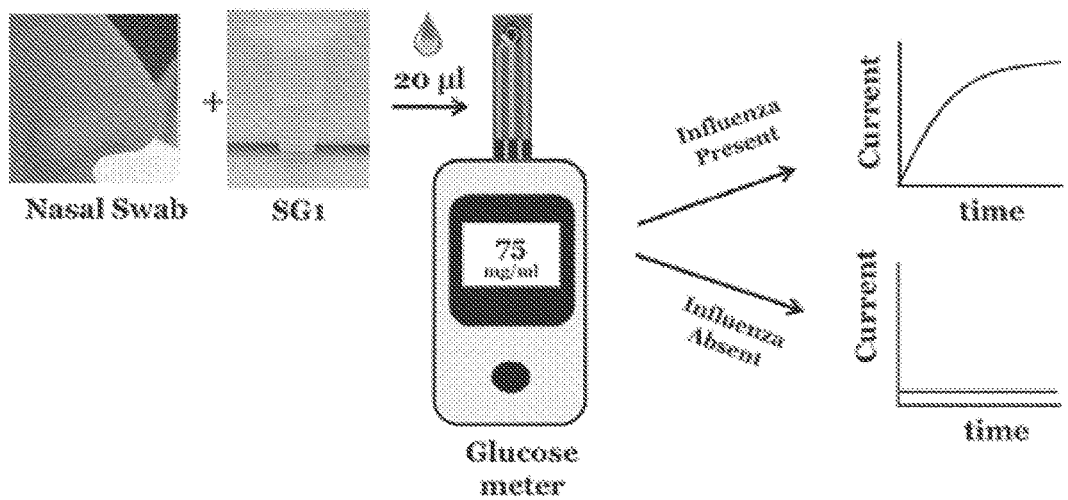
FIG. 4A shows workflow and scheme for electrochemical detection of influenza virus.
Figure 4B:
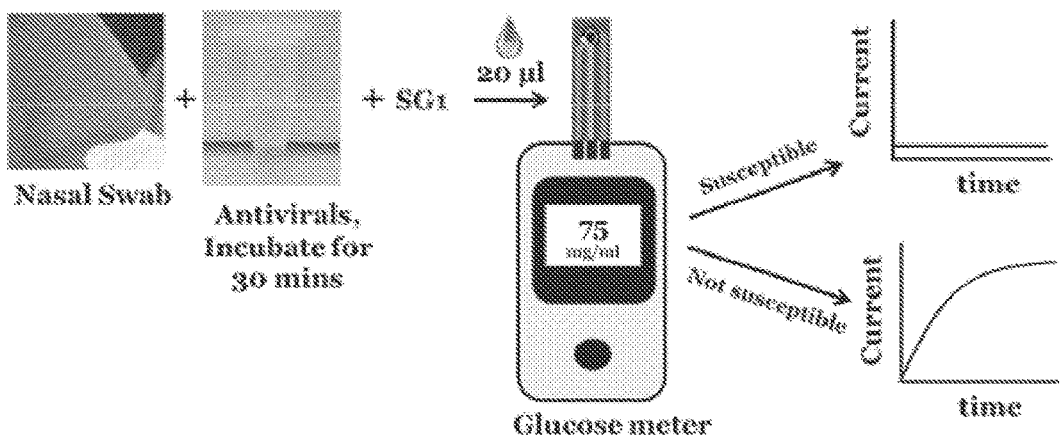
FIG. 4B shows measurement of drug susceptibility.
Figure 4C:
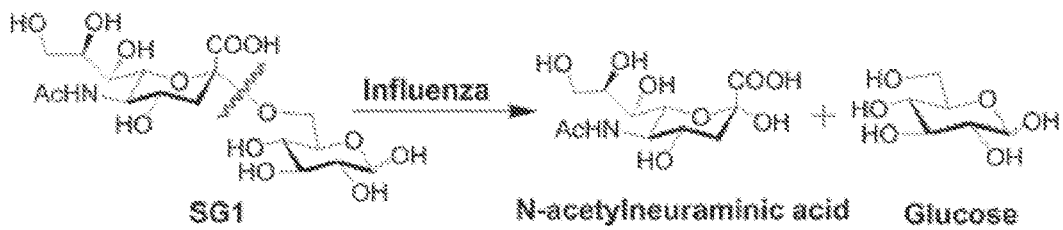
FIG. 4C shows influenza cleaves N-acetyl neuraminic acid from the α 2,6 linked N-acetyl neuraminic acid-glucose derivative, SG1, to release glucose.
Figure 5A:
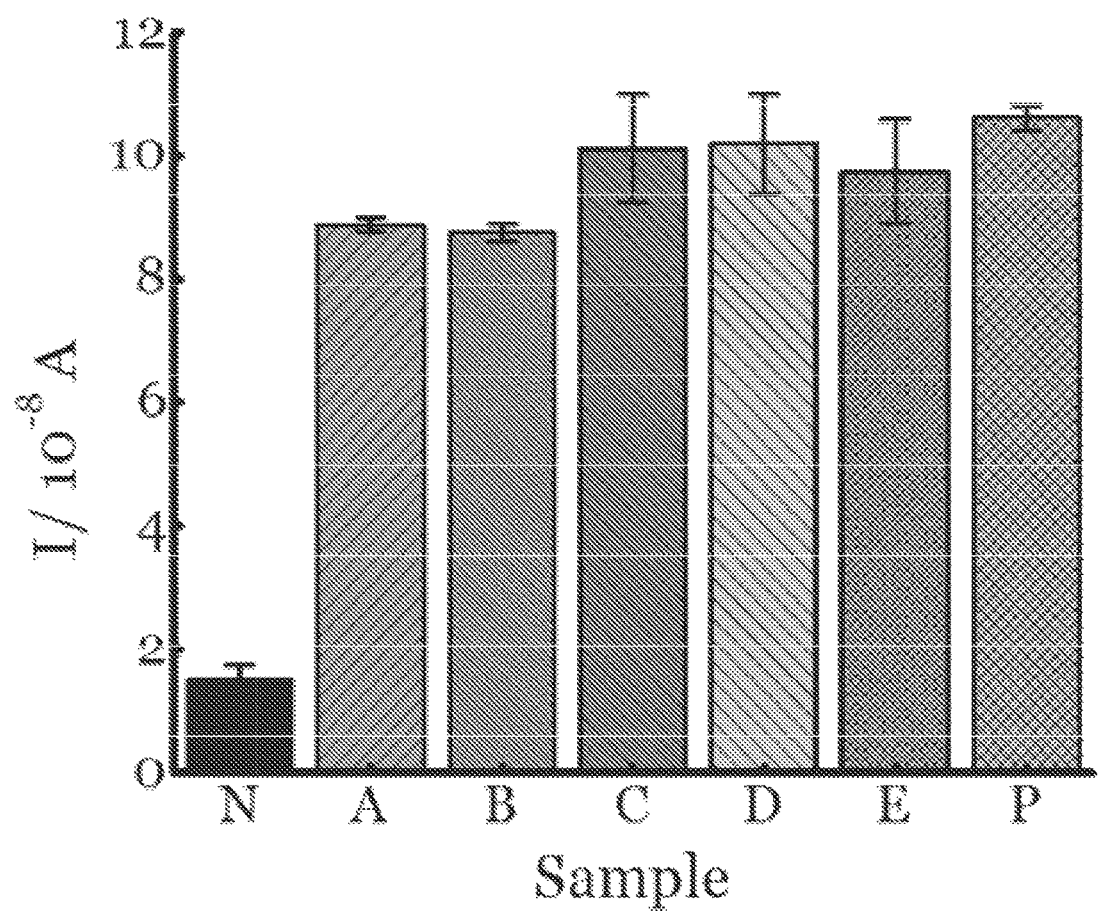
FIG. 5A shows detection of Influenza virus or viral NA. SG1 (0.5 mM) was incubated with membrane free soluble N1 NA (Sample A, strain H5N1 A/Anhui/1/2005) or N2 NA (Sample B, strain A/Babol/36/2005) or three different UV inactivated influenza strains, H3N2 A/Aichi/2/1968 (Sample C) or H1N1 A/Brisbane/59/2007 (Sample D), H3N2 A/HongKong/8/68 (Sample E) for two hours. The NAs were obtained from Sino Biological USA, North Wales, Pa. and the strains were obtained from BEIresources, Manassas, Va. The solution was tested for the presence of glucose using an electrochemical setup. Glucose was released by all five samples. The negative control where no virus or NA was added (Sample N) did not show any noticeable current and the positive control was D-glucose (Sample P) at 0.5 mM.
Figure 5B:
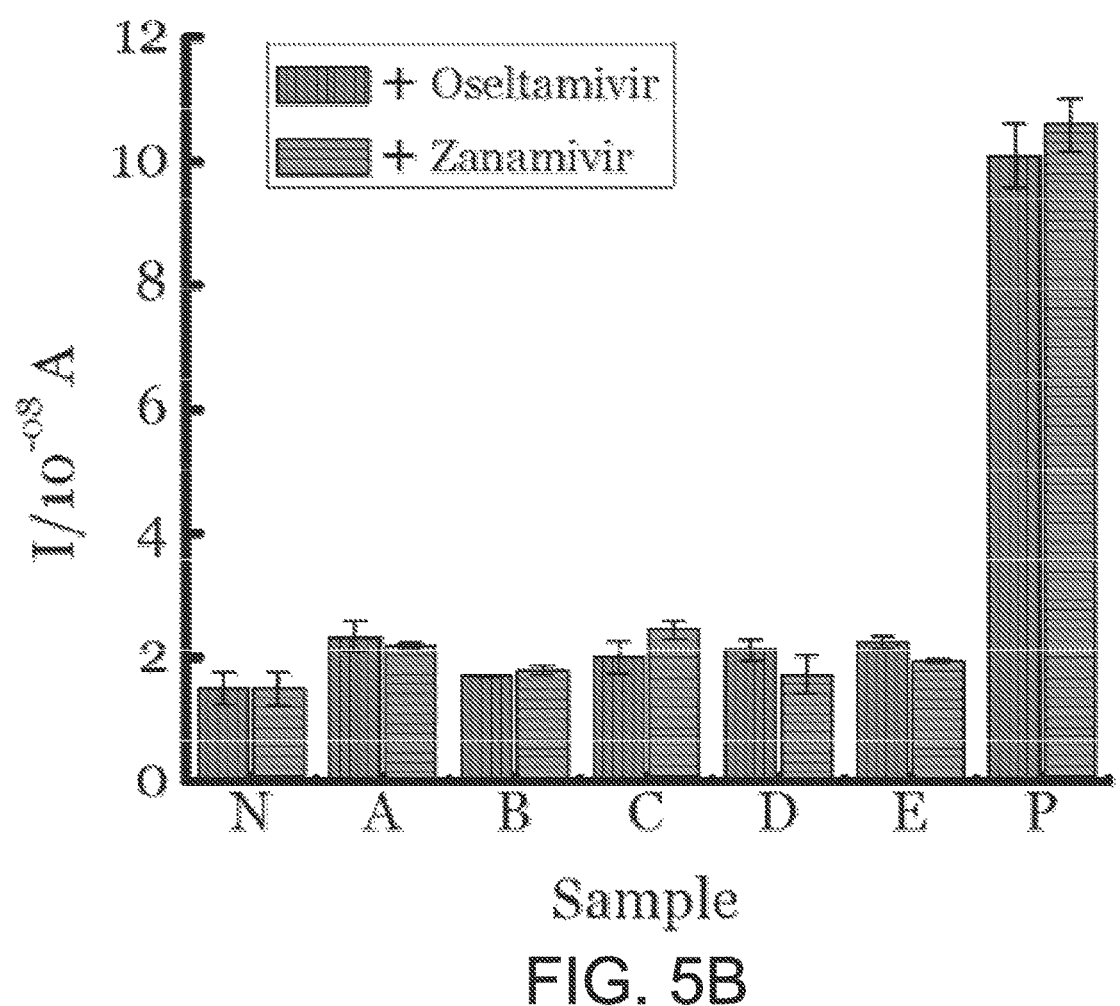
FIG. 5B shows Drug Susceptibility Studies. 10 ng of FDA approved antiviral Zanamivir or Oseltamivir (Carbosynth, USA, San Diego, Calif.) Zanamivir® or Oseltamivir® were premixed with the strains for 30 min at rt before addition of SG1. Glucose was not released because these strains are susceptible to the drugs.
Figure 5C:
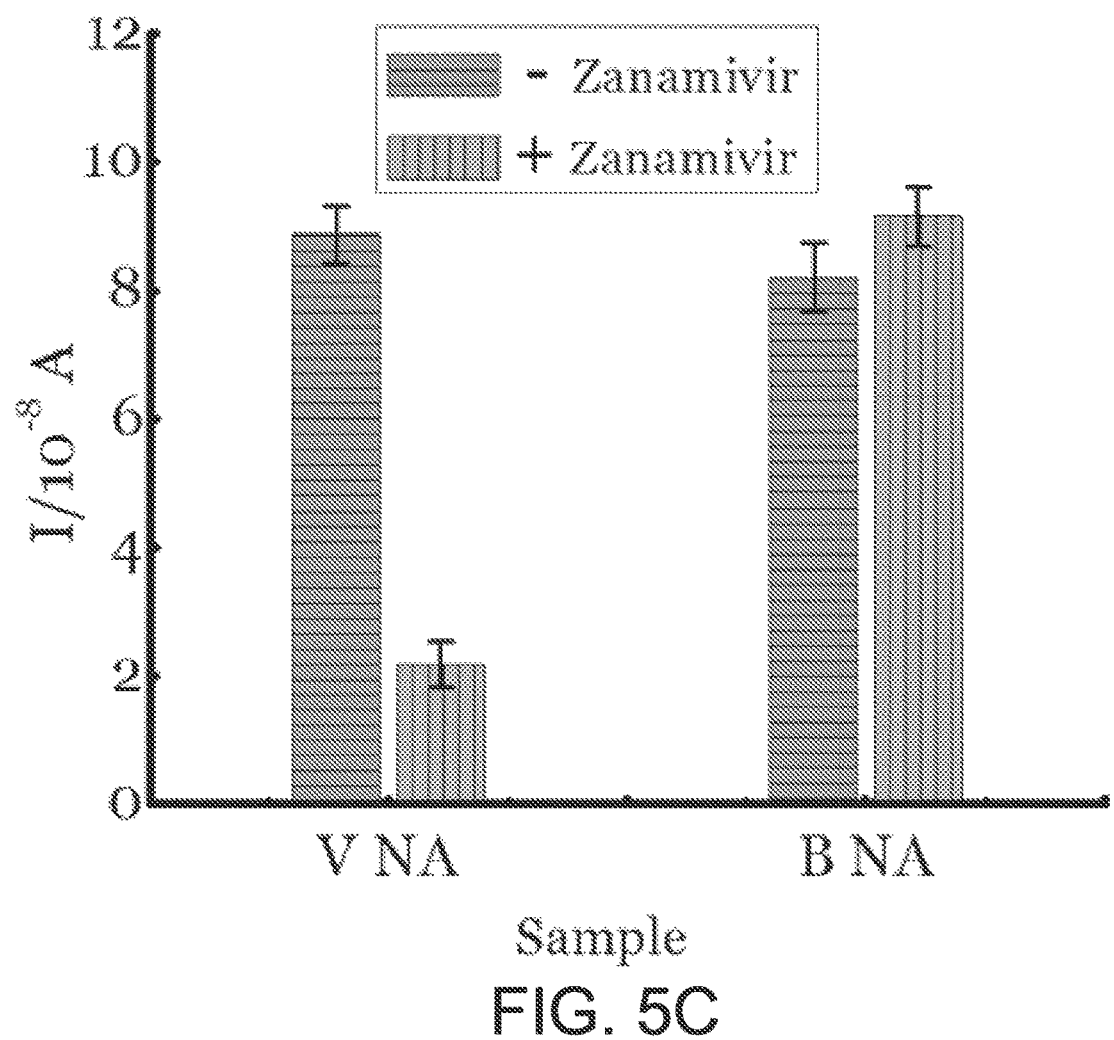
FIG. 5C shows studies with bacterial NA. Bacterial NA also cleaves SG1 to release glucose, however, the antiviral drugs do not inhibit bacterial NA. Therefore, glucose was released when the bacterial NA was premixed with Zanamivir and incubated with SG1. All experiments were performed independently on three different days to demonstrate robustness of the assay.

GODs from different sources have various optimal pH ranges. Generally, GOD from fungi and yeast, such as *Aspergillus niger* GOD which was used in fabricating our glucose biosensor, is most active in an acidic to neutral pH range. On the other hand, CS stays insoluble when pH is above 6.3. Considering both factors, a buffer with the pH of 6.9 was chosen. The amperometric response of PB/Bi$_2$Se$_3$ coated GCE at different concentration of glucose is shown in FIG. 2. Excellent linear response with a correlation coefficient of 0.998 is observed in the range of 12.5 μM to 800 μM. The detection limit was found to be sufficient for detecting glucose from influenza virus hydrolysis samples.

Hydrolysis of Sialylglucose by Recombinant NA or Influenza Viruses

Influenza neuraminidases are enzymes that can hydrolyze terminal sialic acid from glycoproteins or glycolipids. The ability of influenza NA to hydrolyze the probe (α-2,6-sialylglucose) was investigated by mass spectroscopy. To ensure a complete hydrolysis, the probe was incubated with NA overnight. At a physiological pH 7.40 and room temperature at overnight incubation, both the probe peak and hydrolysis product sialic acid peak could be seen, indicating an incomplete hydrolysis. However, when the pH was adjusted to 5.68 and temperature was increased to 37° C. which was optimal for NA, the substrate peak could no longer be observed. The same condition was applied for intact influenza virus hydrolysis and the mass spectrum showed complete hydrolysis for both $H_1N1$ and $H_3N_2$ viruses.

The molecular ion peak of both α-2,6-sialylglucose and sialic acid could be clearly seen in the mass spectrum, however, the glucose peak was hardly observed. The reason is that glucose lacks functional groups such as carboxyl group or amine group, which can be easily ionized. The mass spectrum obtained from a sample containing equal amount of sialic acid and glucose showed strong peak of sialic acid but very tiny peak of glucose. Thus, the appearance of the sialic acid peak and the disappearance of α-2,6-sialylglucose peak could be used to assess the completion of probe hydrolysis.

Electrochemical Sensing of Glucose in NA or Influenza Virus Hydrolysis Samples

The concentration of glucose from the hydrolysis of α-2,6-sialylglucose by recombinant NA or intact influenza viruses were measured amperometrically. The hydrolysis reaction was carried out in 10 mM $NH_4OAc$ buffer with a pH of 5.68 and the reaction mixture then was diluted in PBS buffer containing 0.1 KCl as support electrolyte for electrochemical sensing using 1 mM of the substrate. Amperometric responses of overnight hydrolysis samples by NA or influenza viruses are shown in FIG. 3. The concentrations of glucose in these hydrolysis samples was calculated by applying the current value into the linear regression equation obtained from the glucose standard curve.

The hydrolysis reaction was also allowed to proceed for varying lengths of time. The hydrolysis of α-2,6-sialylglucose by H1N1 virus was stopped at 1 h, 5 h and overnight respectively and the current was recorded. The 1 h and 5 h samples showed currents comparable to the 100 μM glucose standard solution while the overnight sample showed significantly lower current. This result indicated that the hydrolysis reaction was completed in h, however, elongation of incubation time decreased the glucose concentration, presumably because the released glucose is consumed by the virus or is degraded by an unknown mechanism if left overnight. Summary of current and calculated glucose concentration in all hydrolysis samples is shown in Table 2 below.

TABLE 2

Summary of amperometric current and calculated concentration of glucose in sialylglucose hydrolysis samples by NA or influenza viruses.

| Sample | Current(A) | Calculated Glucose Concentration (μM) |
| --- | --- | --- |
| H1N1 virus 1 h | 1.262E−07 | 116.2 |
| H1N1 virus 5 h | 1.366E−07 | 126.6 |
| H1N1 virus overnight | 6.066E−08 | 50.66 |
| H3N2 NA overnight | 1.123E−07 | 102.3 |
| H5N1 NA overnight | 7.647E−08 | 66.47 |
| H3N2 virus overnight | 8.609E−08 | 76.09 |

Conclusions

Influenza viruses could be readily detected using ca-2,6-sialylglucose as a probe. Mass spectroscopy confirmed that α-2,6-sialylglucose was hydrolyzed by both recombinant NA and intact influenza viruses. The hydrolysis product β-D-glucose could then be detected quantified using electrochemical methods.

Example 2: Point of Care Electrochemical Assay to Detect Influenza Viruses and Measure Drug Susceptibility Materials and Methods Glycosylation reactions were performed under argon with solvents dried using a solvent purification system (Innovative Technology Inc., Amesbury, Mass., USA). Other chemical reagents were of analytical grade, used as supplied, without further purification unless indicated. The acidic ion exchange resin used was Amberlite® IR-120 ($H^+$) resin. Analytical thin layer chromatography (TLC) was performed on silica gel 230-400 mesh (Silicycle, Quebec City, Canada). Plates were visualized under UV light, and/or by staining with acidic $CeH_8Mo_3N_2O_{12}$, followed by heating. $^1H$ and $^{13}C$ NMR spectra were recorded on Bruker 400 MHz spectrometer. Chemical shifts are reported in δ (ppm) units using $^{13}C$ and residual $^1H$ signals from deuterated solvents as references. Spectra were analyzed with MNova® (Mestrelab Research, Escondido, Calif., USA). Electrospray ionization mass spectra were recorded on a Micromass QT 2 (Waters) and data were analyzed with MassLynx® 4.0 (Waters, Milford, Mass., USA) software. Reported yields refer to spectroscopically and chromatographically pure compounds that were dried under high vacuum ($10^{-2}$ mbar) before analytical characterization, unless otherwise specified.

Abbreviations: N, N Dimethyl formamide, DMF; Ethyl acetate, EtOAc; Dichloromethane, DCM; Thin layer chromatography, TLC; Methanol, MeOH; Ethanol, EtOH; Sodium hydride, NaH; Benzyl bromide, BnBr; Triethylamine, $NEt_3$; tert-Butyldimethylsilyl chloride, TBSCl; 4-Dimethylaminepyridine, DMAP; Sulphuric acid, $H_2SO_4$; Trifluoromethanesulfonic acid, TfOH; N-Iodosuccinimide, NIS; Sodium methoxide, NaOMe; Palladium hydroxide, Pd(OH)$_2$; Sodium hydroxide, NaOH; Sodium thiosulfate, $Na_2S_2O_3$; Hydrochloric acid, HCl; Glucose oxidase, GOD.

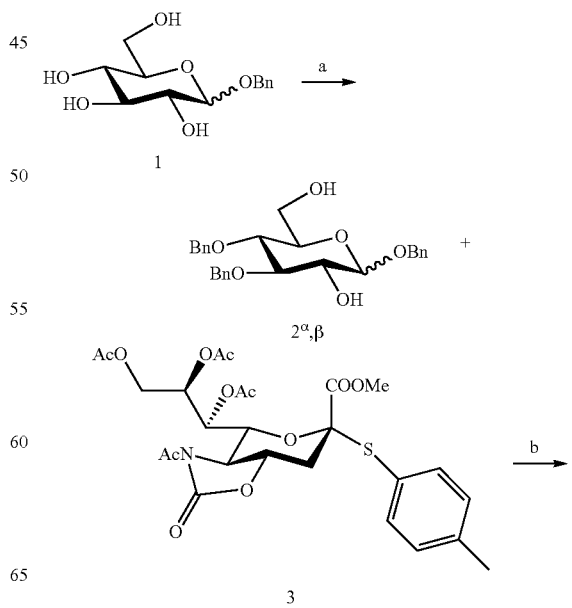

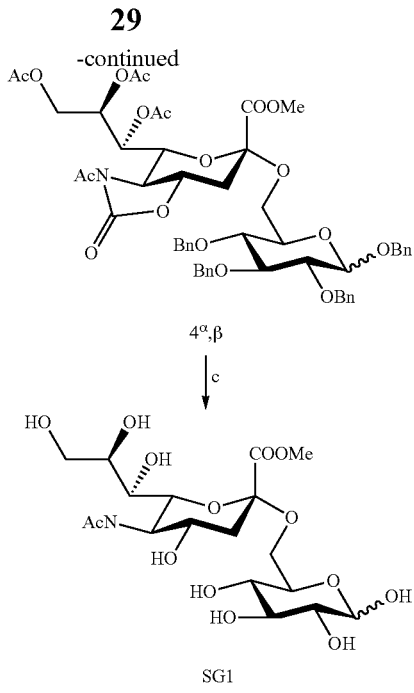

4α,β

↓ c

SG1

Scheme 4. Reagents and Conditions: a) i) Pyridine, TBSCl, DMAP, rt, overnight; ii) NaH, BnBr, DMF, 0° C.-rt, 3 h; iii) 1M $H_2SO_4$ in MeOH, MeOH, rt, 1 h, 27% yield for 2a and 20% yield for 2β over three steps; b) TfOH, NIS, DCM, −60° C., 2 h, 75%; c) i) NaOMe, MeOH, rt, 30 min.; ii) $Pd(OH)_2/C/H_2$, EtOH, rt, 12 h.; iii) 0.05 N NaOH in $H_2O$, rt, 4 h, 93% over three steps.

Benzyl 2,3,4-tri-O-benzyl-α,β-D-glucopyranoside (2α,β)

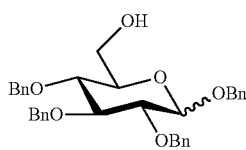

2α,β

To a solution of compound 1 (1.0 g, 3.7 mmol) in pyridine (0.010 L), TBSCl (0.85 g, 5.5 mmol) was added, followed by addition of DMAP (0.04 g, 0.37 mmol). The reaction mixture was stirred overnight at rt. After completion of reaction as monitored by TLC, the solvent was removed using a rotary evaporator and the crude compound was used directly without further purification. To a stirred suspension of NaH (0.89 g, 18 mmol, prewashed with dry hexane to remove the oil present in 60% suspension of NaH) in anhydrous DMF (0.010 L), the crude TBS compound in DMF (0.010 L) was added at 0° C. The reaction mixture was stirred under argon atmosphere for 30 min. BnBr (2.2 ml, 18 mmol) was added dropwise via syringe and reaction mixture was stirred for 3 h. The reaction was quenched with 1M HCl (10 mL), diluted with EtOAc (20 mL) and washed with water (2×10 mL) and brine (2×10 mL). The organic layer was dried over $NaSO_4$ and concentrated under reduced pressure to obtain the tetra benzyl protected compound. The crude compound was used directly without further purification. To a stirred solution of the crude compound in MeOH (0.020 L), $H_2SO_4$ in MeOH (1M, 0.50 mL) was added. The reaction mixture was stirred at rt and the reaction progress was monitored by TLC using two solvent systems: EtOAc-hexanes (1:9) and EtOAc-hexanes (1:1). After completion of reaction as monitored by TLC, the reaction mixture was diluted with EtOAc (20 mL) and washed with saturated $NaHCO_3$ (2×20 mL) and brine (2×20 mL). The organic layer was dried over $NaSO_4$, concentrated under reduced pressure and subjected to flash chromatography to give 2a (0.55 g, 27% over three steps) and 2β (0.40 g, 20% over three steps). Spectral data is in complete agreement with reported value (Fokt, I. et al. Carbohydr Res 368, 111-119 (2013)).

Methyl 5-acetamido-7,8,9-tri-O-acetyl-5-N,4-O-carbonyl-3,5-dideoxy-D-glycero-α-D galacto-non-2-ulopyranosylonate-(2- 6)-1,2,3,4-tetra-O-benzyl-α-D-glucopyranoside (4a)

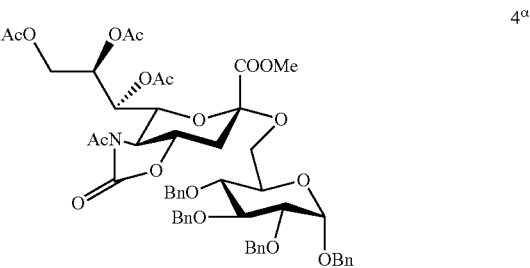

4α

To the stirred solution of acceptor 2a (0.20 g, 0.35 mmol) and donor 3 (0.24 g, 0.38 mmol) in anhydrous DCM (4.0 ml) under an argon atmosphere at −40° C., NIS (0.19 g, 0.84 mmol) was added followed by TfOH (0.52 ml, 0.35 mmol, 10% in anhydrous DCM). The reaction mixture was stirred at this temperature for ~2 h until complete disappearance of the acceptor as determined by TLC. $NEt_3$ (0.50 mL) was added to quench the reaction and warmed to rt. The reaction mixture was diluted with DCM (20 mL), washed with aqueous solution of $Na_2S_2O_3$ (2×10 mL) dried over $Na_2SO_4$ and concentrated under reduced pressure. The residue was subjected to flash silica gel column chromatography eluting with (hexanes:EtOAc 7:3) to afford the 4a (0.27 g, 75%) as a white solid. $^1$H NMR (400 MHz, $CDCl_3$): δ 7.45-7.26 (m, 20H), 5.58 (dd, J=8.9, 1.7 Hz, 1H), 5.45 (ddd, J=8.5, 6.1, 2.5 Hz, 1H), 4.97 (d, J=10.8 Hz, 1H), 4.86-4.78 (m, 3H), 4.76 (d, J=6.1 Hz, 1H), 4.73-4.65 (m, 2H), 4.56 (dd, J=15.0, 12.2 Hz, 2H), 4.26 (dd, J=12.4, 2.7 Hz, 1H), 4.20 (dd, J=10.8, 4.5 Hz, 1H), 4.14 (d, J=7.2 Hz, 1H), 4.08-3.98 (m, 2H), 3.98-3.84 (m, 2H), 3.73 (s, 3H), 3.66 (dd, J=11.2, 9.4 Hz, 1H), 3.60 (d, J=9.4 Hz, 1H), 3.58-3.52 (m, 1H), 3.49 (dd, J=10.6, 2.0 Hz, 1H), 2.94 (dd, J=12.1, 3.4 Hz, 1H), 2.49 (s, 3H), 2.15 (s, 3H), 2.12-2.06 (m, 1H), 2.04 (s, 3H), 1.81 (s, 3H). 13C NMR (100 MHz, $CDCl_3$): δ 171.8, 170.6, 169.9, 169.9, 168.4, 153.6, 138.8, 138.4, 138.2, 137.1, 128.4, 128.3, 128.0, 127.9, 127.8, 127.7, 127.5, 99.2, 95.5, 81.9, 79.6, 77.5, 75.7, 75.2, 75.0, 74.9, 73.0, 71.4, 69.9, 69.0, 68.4, 64.7, 62.8, 59.1, 52.9, 36.6, 24.7, 21.1, 20.7, 20.5. HRMS (ESI): Calculated for $C_{53}H_{59}NO_{18}Na$ [M+Na] 1020.3630; Found 1020.3629.

Methyl 5-acetamido-7,8,9-tri-O-acetyl-5-N,4-O-carbonyl-3,5-dideoxy-D-glycero-α-D galacto-non-2-ulopyranosylonate-(2→6)-1,2,3,4-tetra-O-benzyl-β-D-glucopyranoside (4β)

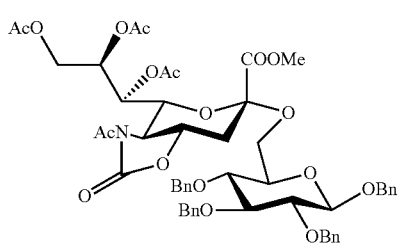

4β was synthesized in a manner from donor 3 (0.24 g, 0.38 mmol) and 23 (0.20 g, 0.35 mmol) similar to that of 4α and the product was purified using flash silica gel column chromatography eluting with hexanes:Et$_2$OAc (7:3) to afford the compound 43 (0.27 g, 75%) as a yellowish solid. $^1$H NMR (400 MHz, CDCl$_3$): δ 7.46-7.24 (m, 20H), 5.65 (d, J=8.6 Hz, 1H), 5.52 (dt, J=8.7, 4.3 Hz, 1H), 4.97 (d, J=11.5 Hz, 2H), 4.91 (d, J=10.9 Hz, 1H), 4.82 (s, 2H), 4.76 (t, J=11.0 Hz, 2H), 4.68 (dd, J=10.8, 5.5 Hz, 2H), 4.51 (d, J=7.9 Hz, 1H), 4.37 (dd, J=12.4, 2.8 Hz, 1H), 4.21 (dd, J=11.2, 4.6 Hz, 1H), 4.11-3.95 (m, 2H), 3.76 (s, 3H), 3.75-3.60 (m, 4H), 3.56-3.44 (m, 2H), 2.99 (dd, J=12.3, 3.2 Hz, 1H), 2.51 (s, 3H), 2.16 (s, 3H), 2.11 (s, 3H), 2.12-2.01 (m, 1H), 1.91 (s, 3H). 13C NMR (100 MHz, CDCl$_3$): δ 177.5, 171.8, 170.6, 170.0, 168.3, 153.7, 138.6, 138.4, 138.3, 137.3, 128.4, 128.4, 128.4, 128.3, 128.1, 128.1, 127.9, 127.9, 127.8, 127.8, 127.7, 127.7, 127.6, 127.6, 102.3, 99.3, 84.5, 82.0, 75.7, 75.20, 75.1, 74.8, 73.9, 71.5, 71.0, 68.6, 64.6, 62.9, 59.1, 52.9, 36.6, 24.7, 21.2, 20.8, 20.6. HRMS (ESI): Calcd for C$_{53}$H$_{59}$NO$_{18}$Na [M+Na] 1020.3630; Found 1020.3629.

5-acetamido-3,5-dideoxy-D-glycero-α-D-galacto-non-2-ulopyranosylonate-(2→6)-α,β-D-gluco pyranoside (SG1)

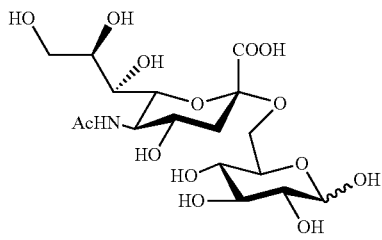

4a or 4β (0.060 g, 0.060 mmol) was dissolve in MeOH (0.010 L) and treated with a 30% solution of NaOMe (75 μl) in CH$_3$OH and stirred at rt for 1 h. The solution was neutralized with Amberlite® IR 120 (H$^+$) resin, filtered and concentrate to dryness. The dried compound was treated with Pd(OH)$_2$/C (0.010 g) in absolute EtOH was stirred for 12 h at rt under H$_2$ at 1 atmosphere. After completion of reaction as monitored by TLC, reaction mixture was filtered using celite pad, washed with EtOH and combined solvent was concentrate to dryness. The dried compound was treated with NaOH (0.05 N, 3.0 mL) and reaction was stirred for 4 h. After completion of reaction, as monitored by TLC (DCM:MeOH:NH$_4$OH) (8:2:1), reaction was neutralized using Amberlite® IR 120 (H+) resin, filter, concentrate and subjected to P-2 gel column to furnish α/β mixture of the title compound 5 (0.013 g, 93% over three steps) (54:46, ratio determined by $^1$H NMR spectroscopy). $^1$H NMR (400 MHz, D$_2$O) δ 5.12 (d, J=3.1 Hz, 1H, H1α), 4.54 (d, J=7.8 Hz, 1H, H1β), 4.07-3.86 (m, 2H), 3.86-3.69 (m, 7H), 3.68-3.53 (m, 5H), 3.51-3.41 (m, 2H), 3.40-3.33 (m, 1H), 3.19-3.14 (m, 1H), 2.63 (dd, J=12.5, 4.2 Hz, 1H), 1.95 (s, 3H), 1.74-1.68 (m, 1H) $^{13}$C NMR (101 MHz, D$_2$O) δ 177.7, 176.8, 174.7, 95.9, 92.1, 75.6, 74.4, 73.9, 72.3, 72.8, 71.4, 71.8, 69.5, 69.45, 6.2, 68.2, 67.9, 63.1, 62.9, 62.7, 51.8, 39.7, 22.0. HRMS (ES): Calcd for C$_{17}$H$_{29}$NO$_{14}$Na [M+Na]≥ 494.1486, found 494.1497.

Assays

Cells and Viruses.

MDCK (Madin-Darby canine kidney) cells were purchased from ATCC® (CCL-34™, Manassas, Va.) and maintained in Dulbecco's Modified Eagle Medium (DMEM, Gibco, Grand Island N.Y.) supplemented with 10% Fetal Bovine Serum (FBS Gibco, Grand Island N.Y.). Influenza A virus strains used in this study were obtained from BEI Resources (Manassas, Va.).

Nasal and Throat Sample Collection.

Nasal and throat samples were collected from four healthy volunteers. Dry sterile cotton tipped swabs were used for each sample collection. Samples were stored in phosphate buffered saline (PBS) at 4° C. until subsequent use.

Plaque Assays.

Virus titers of different influenza strains were determined using standard plaque assays in MDCK cells to quantify the amount of virus. MDCK cells were grown to confluency in 6-well plates. Once confluent, media was removed from the cells and were washed three times with plain DMEM to remove residual FBS. Virus suspension was serially diluted 10-fold and added to duplicate wells at 400 μL/well. Virus was adsorbed for 1 h at 37° C. in a 5.0% CO$_2$ incubator. One-hour post-adsorption, virus suspension was removed and Avicel (1.2%, 2.0 mL, FMC Biopolymer) supplemented with 2 μg/mL TPCK-trypsin (Sigma-Aldrich, St. Louis, Mo.) was added to each well. Avicel was prepared as described previously (Matrosovich, M., et al. Virol J 3:63 (2006)). Plates were incubated for 5 days to allow for plaque formation. On day 5, the Avicel overlay was removed carefully from each well and the wells were washed two times with 1×PBS followed by methanol (100%) fixation. Fixed wells were stained with 0.2% crystal violet and plaques were counted to determine virus titers.

Real-Time RT-PCR.

Viral RNA was extracted according to manufacturer's instructions using MagMAX viral isolation kit (Life Technologies, Grand Island N.Y.). cDNA was synthesized from the viral RNA using High Capacity cDNA Reverse Transcription Kit purchased from Applied Biosystems (Grand Island, N.Y.). Real time PCR was performed using primers and probe for matrix gene, as described previously (van Elden, L. J., et al. Journal of clinical microbiology 39:196-200 (2001)).

Electrochemical Assay Using the 3 Electrode System.

Figure 7A:
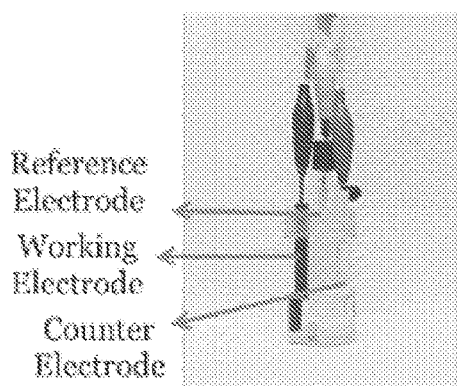
FIG. 7A is an image of the electrochemical cell.
Figure 7B:
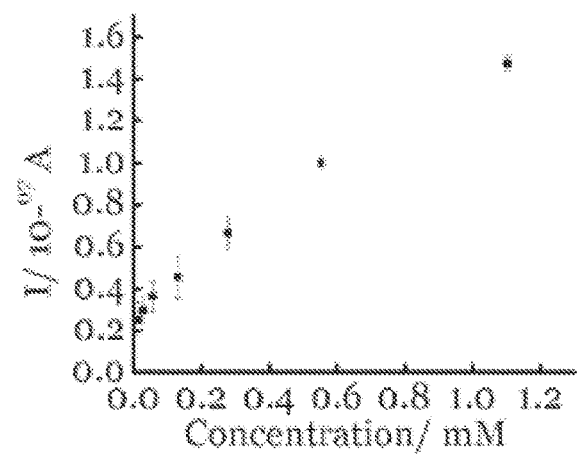
FIG. 7B is as standard curve glucose concentration versus current using the electrochemical cell. Amperometric i-t curve was recorded using different concentrations of glucose and the current at 100 seconds is reported.
Figure 8:
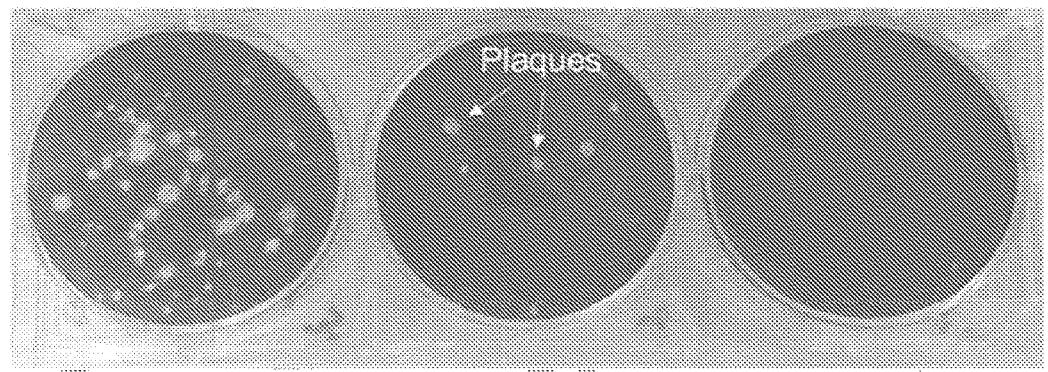
FIG. 8 shows images of plaque assay for one strain. Confluent MDCK cells were infected with approximately 60, 6 and 0 viral particles (A/Brisbane/59/2007) and incubated for 5 days with a semi-solid media overlay. Plaque forming units (pfu) were counted after fixing and staining the cells.
Figure 9:
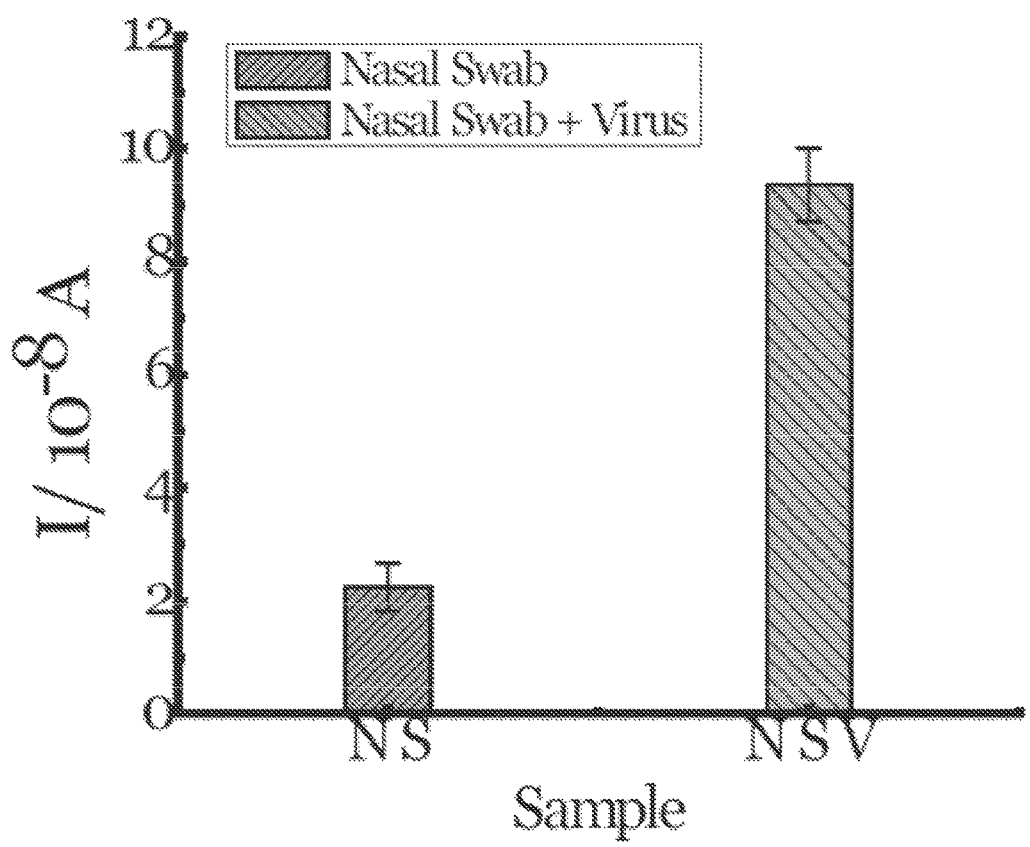
FIG. 9 is a bar graph showing current, I, in amperes measured after 100 s using an amperometric i-t curve at a working potential of 0.00 for nasal swab (NS), where no glucose is present, and nasal swab spiked with $10^5$ pfu of H1N1 A/Brisbane/59/2007 and added to SG1. The positive signal indicates there are no matrix effects.
Figure 10A:
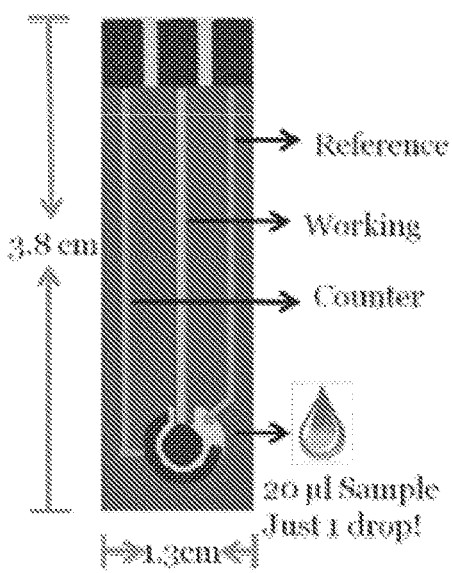
FIG. 10A is an image of the printed disposable electrode to improve performance and user friendliness.
Figure 10B:
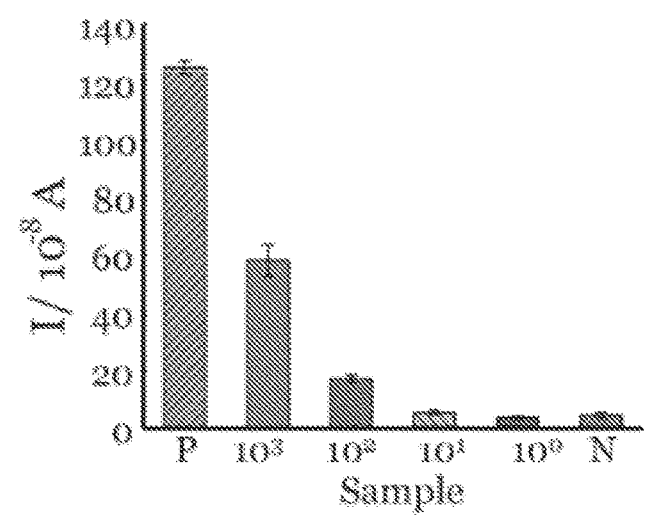
FIG. 10B is a bar graph showing analytical sensitivity studies using A/HongKong/8/1968 (H3N2) strain. P is positive sample, which is 1 mM glucose, N is negative control (SG1 but no virus), and the numbers represent the number of viral particles in the sample. 100 μL of virus containing solution was mixed with SG1 (100 μL, $2\times10^{-3}$ M) for 1 h. 20 μL of this solution was used to test for the presence of glucose. The y axis represents current, I, in amperes measured after 100 s using an amperometric i-t curve at a working potential of 0.00 V, and the x-axis represents different samples.

The initial proof of principle studies were performed using three-electrode system (Wu, S., et al. Biosens Bioelectron 38, 289-294 (2012)) (FIG. 7A, 7B). Briefly, a glassy carbon working electrode (GCE, 3.0 mm in diameter), a saturated calomel reference electrode, and a platinum counter electrode. Fabrication of the electrode was performed by polishing the surface of the glassy carbon electrode on the alumina slurries to form a clear mirror followed by washing with distilled water and drying with $N_2$. The electrode was coated with coating solution achieved by mixing 1 ml of solution A (2 mM Bi $(NO_3)$. $5H_2O$ and 3 mM $SeO_2$ in 1:20 diluted nitric acid) and 2 ml of solution B (2 mM $K_3Fe(CN)_6$, 2 mM $FeCl_3$, 0.1M KCl and 10 mM HCl) followed by cyclic voltammetry scanning from +0.60 V to −0.20 V at 20 mVs$^{-1}$ for 30 cycles. After the coating, the electrode was activated by cycling from 0.35 V to −0.05 V at 50 mVs$^{-1}$ for 30 times in solution C (0.1M KCl and 10 mM HCl). 5 mg of Glucose oxidase (GOD) was dissolved in 1 mL of 0.5% chitosan solution (prepared in 2% acetic acid) and the resulting GOD (10 μL) solution was dropped on the surface of the electrode to form a GOD layer. The GOD layer was air dried to form a firm coated layer on the working electrode. To detect the neuraminidase activity of influenza virus, 100-200 μL of virus stock (PFU determined by plaque assays) was incubated with SG1 (500 μL, 1×10-3 M) for 1 h. To detect the Amperometric response, final solution volume was adjusted to 1 mL. Virus was inactivated using UV light or 1% Triton X-100 (Sigma Aldrich, St. Louis Mo.). The amount of glucose released by NA cleavage of SG1 was detected by glassy carbon electrode using electrochemical analyzer (CH Instruments Ltd, China) at rt. An amperometric i-t curve at a working potential of 0.00 V was recorded and the current at 100 seconds (when stable) is reported. Increase in peak current correlates with increased glucose concentration, which in turn, reflects the activity of influenza virus neuraminidase.

Drug Susceptibility Studies.

10 ng of Zanamivir or Oseltamivir carboxylate was premixed with the virus for 30 min. Next, the solution was incubated with SG1 for 1 h at rt. and glucose released was measured as described in the previous section.

Electrochemical Assay Using the Printed Electrodes.

Printed electrodes were purchased from CH instruments, Austin, Tex., USA, (FIG. 10A) and coated and activated the surface using the solutions as described above. GOD was coated on the surface using chitosan as previously described. Next, 100 μL of virus containing solution was mixed with SG1 (100 μL, $2\times10^{-3}$ M) for 1 h at 37° C. 20 μL of this solution was dropped onto the surface of the test area of printed electrode to test for the presence of glucose.

Results

Influenza has two major surface glycoproteins, Hemagluttinin (HA) and Neuraminidase (NA), the former is implicated in viral entry and the latter is the enzyme that cleaves N-acetyl neuraminic acid (sialic acid) from the surface of host cells to facilitate release of viral progeny (von Itzstein, M. Nat Rev Drug Discov 6, 967-974 (2007)). There are approximately 50-100 copies of NA on the viral surface as determined by immunogold labeling and cryoelectron tomography (Harris, A., et al. Proc Natl Acad Sci USA 103, 19123-19127 (2006); Wasilewski, S., et al. Vaccine 30, 7368-7373 (2012)). Since NA is present as a tetramer with four active sites, there are approximately 200-400 individual units capable of cleaving sialic acids, which makes it a suitable target for biosensing applications. Since NA cleaves terminal sialic acids present on glycoproteins and glycolipids, a sialic acid derivative (SG1) was synthesized where sialic acid is attached to the 6 position of D-glucose (FIG. 4). To measure D-glucose, a three electrode electrochemical cell was developed comprising of a reference, working and counter electrode, and a standard curve was developed (Wu, S., et al. Biosens Bioelectron 38, 289-294 (2012)). Glucose oxidase was coated onto the working electrode using chitosan as glue. A suitable promoter was used to amplify the current. This electrochemical cell was used to develop a standard curve with different concentrations of glucose (FIGS. 7A and 7B). Next, SG1 (0.5 mM) was dissolved in PBS buffer and tested for the presence of glucose. In the absence of enzymes, there is no glucose released (FIG. 5A, sample N, negative control, no NA or virus added). Next, membrane free influenza viral NA from two different strains (N1 from strain H5N1 A/Anhui/1/2005 and N2 from strain A/Babol/36/2005) was incubated for 2 hours at 23° C. in PBS buffer with SG1. The sample was analyzed for the presence of glucose directly without further sample preparation. Glucose was released as determined by the current released, which indicated that complete cleavage of SG1 had occurred (FIG. 5A, samples A, B). The positive control (FIG. 5A, sample P) was a solution with glucose as the only analyte in PBS buffer. These studies demonstrated that viral Neuraminidase cleaves SG1 to release glucose, which can be measured using a standard electrochemical setup.

Next, three influenza strains (H1N1 A/Brisbane/59/2007, H3N2 A/Aichi/2/1968, and H3N2 A/HongKong/8/68) were tested, which were quantified by plaque assays and rRT-PCR (FIG. 8). Introduction of the 100 μL of UV inactivated virus to SG1 and incubation for 1 hour, releases glucose. All the strains cleave SG1, releasing glucose (FIG. 5A, Samples C,D,E). The cleavage was confirmed by mass spectral analysis. The mass spectra of the control where there is no virus or NA revealed a peak at m/z 470.19 (M+1 positive ion) corresponding to uncleaved SG1. A new peak emerges at m/z, 181.0711 (M+1, positive ion) corresponding to glucose when virus or NA is added.

To determine drug susceptibility, FDA approved antivirals Zanamivir or Oseltamivir were premixed to virus or NA for 30 minutes before introducing SG1 to the solution. These two antivirals are NA inhibitors and therefore, if the strains are not resistant to the antivirals, they are expected to block the action of NA and a signal for glucose should not be observed. As seen in FIG. 5B, the three strains and NA are completely inhibited by the antivirals. These strains are not resistant to the action of the antivirals and therefore, drug susceptibility can be measured in real time using this assay. The same assay was also used to distinguish viral NA from bacterial NA. To this end, bacterial NA (BNA) from *Clostridium perfringens* (Sigma Aldrich, St. Louis, Mo.) was introduced to SG1 (FIG. 5C, sample BNA). However, when Zanamivir was premixed with bacterial NA, NA still cleaved SG1 because the antivirals are specific for viral NA (FIG. 5C, sample BNA+Z). Therefore, the assay can distinguish between BNA and viral NA using the antivirals.

Since the output of this assay is glucose, experiments were conducted to determine if matrix effects such as nasal or throat swabs, the standard source of clinical samples, have a background level of glucose or if the matrix can affect the performance of the assay. Nasal and throat swabs were obtained from healthy volunteers and tested for the presence of glucose. There was no glucose present in any of the samples. Next, $10^5$ PFU/ml (Plaque Forming Units) of H1N1 A/Brisbane/59/2007 strains were spiked and the sample tested for glucose. The matrix does not affect the cleavage of the lead compound SG1 (FIG. 9).

After establishing the proof of concept that the electrochemical assay could be used to detect influenza viruses, the next goal was to improve the performance of the assay. Since commercial glucose monitors use disposable screen-printed enzyme electrodes for blood glucose measurements, disposable printed electrodes (CH instruments, Austin, Tex.) were used for the next set of experiments. Glucose oxidase was introduced to the strips and a panel of H1N1 and H3N2 influenza strains were tested that were quantified using plaque assays and rRT-PCR. Some of the strains are old strains, whereas others are very recent strains. Strains were incubated with 0.5 mM of SG1 using a specific set of buffers and reagents to release the viral NA from the membranes for one hour before introduction of 20 μL of the solution to the disposable strips. All strains release glucose; most strains release SG1 with high efficiency in one hour; however, some strains such as A/New Caledonia/20/1999 and A/Aichi/2/1968 require longer time to completely cleave SG1 (Table 3). The advantages of printed electrodes compared to the previous setup is the limited volume of solution needed (20 μL) and the user friendliness of the system. The analytical sensitivity was also determined using one of the strains using this rudimentary setup (FIGS. 10A and 10B). This limit of detection and range is $10^2$ and $10^2$-$10^8$ PFU/ml, respectively. Since multiple studies have reported that patients (number>50) suffering from influenza typically harbor $10^3$-$10^8$ PFU/ml in the nase/throat (Lee, N., et al. J Infect Dis 200, 492-500 (2009); Ngaosuwankul, N., et al. Virol J 7, 75 (2010); Suess, T., et al. PLoS ONE 7, e51653 (2012); Zhang, A., et al. Euro Surveill 18, 20657 (2013)), this assay could be useful for realtime detection of influenza in a primary care setting.

TABLE 3

List of influenza strains evaluated as well as a comparison with rRT-PCR and cell culture plaque assays.

| Influenza strains | Plaque Assay [a] | rRT-PCR ($C_T$)[b] | Electro-chemical assay. (×$10^{-8}$ A)[c] |
|---|---|---|---|
| No virus + SG1 | N/A | N/A | 3.6 ± 2.2 |
| No glucose | N/A | N/A | 3.4 ± 1.4 |
| A/Wilson-Smith/1933 (H1N1) | 4.2 × $10^6$ | 18 | 99.5 ± 4.4 |
| A/PuertoRico/8/1934 (H1N1) | 1.4 × $10^4$ | 15 | 13.4 ± 2.0 |
| A/HongKong/8/1968 (H3N2) | 1.5 × $10^5$ | 22 | 64.4 ± 5.2 |
| A/Aichi/2/1968 (H1N1) | 1.0 × $10^5$ | 15 | 31.3 ± 5.3 |
| A/Beijing/262/1995 (H1N1) | 3.5 × $10^5$ | 21 | 118.1 ± 11.6 |
| A/Nanching/933/1995 (H3N2) | 0.7 × $10^6$ | 18 | 15.1 + 2.8 |
| A/Sydney/5/1997 (H3N2) | 0.8 × $10^4$ | 29 | 115.7 ± 4.3 |
| A/New Caledonia/20/1999 (H1N1) | 4.4 × $10^7$ | 12 | 17.7 ± 2.6 |
| A/Solomon Islands/3/2006 (H1N1) | 1.1 × $10^9$ | 11 | 79.7 ± 5.0 |
| A/Uruguay/716/2007 (H3N2) | 1.2 × $10^7$ | 20 | 132.4 ± 6.3 |
| A/Brisbane/59/2007 (H1N1) | 2.5 × $10^7$ | 12 | 106.2 ± 5.1 |
| A/California/07/2009 (H1N1) | 3.6 × $10^6$ | 13 | 13.4 + 1.5 |
| A/New York/18/2009 (H1N1) | 3.5 × $10^5$ | 17 | 74.4 ± 5.6 |
| A/San Diego/1/2009 (H1N1) | 1.2 × $10^5$ | 19 | 108.5 ± 12.0 |
| A/Wisconsin/629-D02452/2009 (H1N1) | 0.6 × $10^5$ | 13 | 98.9 ± 5.7 |
| A/Wisconsin/15/2009 (H3N2) | 0.5 × $10^4$ | 26 | 107.8 ± 5.9 |
| A/Brownsville/31H/2009 (H1N1) | 0.4 × $10^4$ | 22 | 91.7 ± 9.7 |
| A/Victoria/361/2011 (H3N2) | 7.0 × $10^6$ | 26 | 94.5 ± 2.3 |

[a] Reported in pfu/ml.

[b] rRT-PCR was performed using 100 μL of virus.

[c] 100 μL of virus was mixed with 100 μL of PBS buffer with SG1 for 1 hour at 37° C. Glucose concentration was determined using 20 μL of this mixture.

In summary, an electrochemical assay is disclosed that releases glucose upon introduction of influenza viruses. The assay can be used to measure drug susceptibility, which is a significant advantage over current genotypic and phenotypic methods that take time, resources, and a laboratory environment with specialized equipment and trained personnel (Okomo-Adhiambo, M., et al. Influenza and other respiratory viruses 7 Suppl 1, 44-49 (2013)). The assay can be integrated into current glucose meters by calibrating the instruments to test nasal or throat swabs for influenza. Since glucose meters are user friendly, ubiquitous, the test strips inexpensive and disposable, this method has great potential to improve clinical decisions and minimize disease burden due to influenza. Finally, this concept is unique because, any enzyme, e.g. beta lactamase present in certain drug resistant bacterial strains (Xie, H., et al. Nature chemistry 4, 802-809 (2012)), can be detected by blood glucose meters provided there are sufficient copies of the enzyme and the drugs being tested are enzyme inhibitors.

Example 3: Probes that Will Release Glucose (or any Electrochemical Molecule) on Reaction with an Enzyme Present in a Pathogen or a Host The following are additional examples of the probes to detect enzymes.

*Chlamydia trachomatis.*

Molecules for α mannoside that is produced by Chlamydia trachomatis

A

X = O or NH

R=D-Glucose or D-Galactose or any other electrochemically active moiety (e.g., —$OCH_2CH_3$). D-glucose and D-galactose have 5 hydroxyl groups. In the above example, attachment is at position 6 of glucose. However, attachment can be made any hydroxyl group (e.g., at the 2, 3, or 4 position).

Mechanism

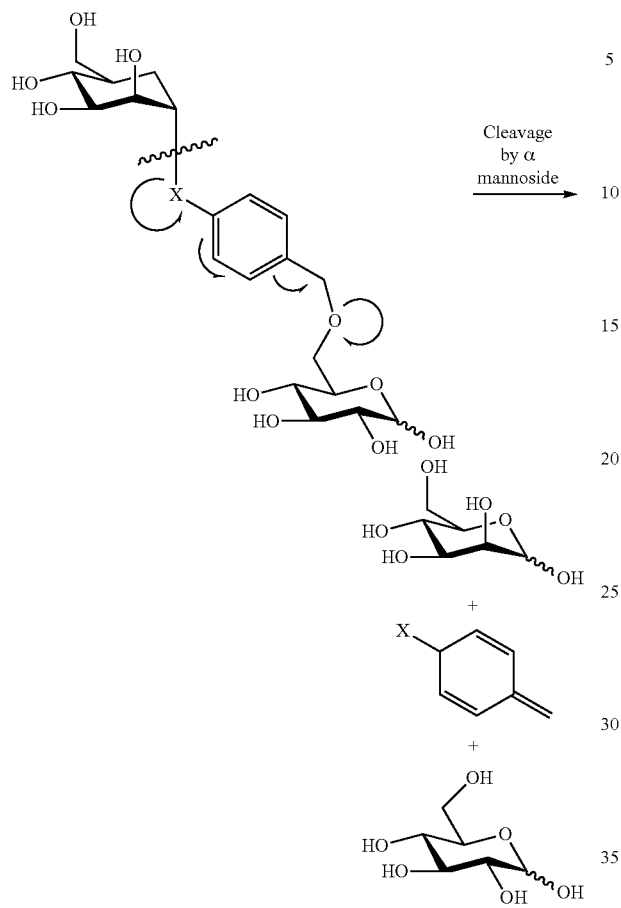

*Neisseria gonorrhoeae* and Related Species.

Typically, 3 enzymes are used to detect *N. Gonorrhoeae*. (Gonochek-II, E-Y laboratories, Inc.). However, a panel of 10 enzymes can be used to differentiate between different Neissseria and related species. Suitable probes for all of these enzymes, which include, but are not limited to, glycosidase, aminopeptidase (arylamidase), phosphatase, phosphoamidase, protease, lipase, esterase, and aryl sulfatase. Within these major classes of enzymes, 3-Galactosidase, γ-Glutamyl aminopeptidase, hydroxyproline aminopeptidase, Arginine aminopeptidase, Serine aminopeptidase, glycyl-glycine aminopeptidase, phosphatase, valerate esterase, 4-Methoxyleucine aminopeptidase and glycine aminopeptidase can be used to differentiate between a number of sexually transmitted diseases (STDs).

Probes for each of these enzymes (e.g., including a substrate for each enzyme covalently linked to an electrochemically active moiety, such that the probe releases the electrochemically active moiety when cleaved by an enzyme) can be prepared using the approaches described herein. The probes can be used in combination to indicate the presence of one or more of these diagnostic enzymes in a sample. Specifically, probes for each of the enzymes can be exposed to a test sample. If the electrochemically active moiety (e.g., glucose or ethanol) is detected following contacting the probe with the sample, it will indicate presence of the enzyme. The amount of the electrochemically active moiety released by the probe can be quantified and the numbers can be input into a table. Analysis of the table will be used to detect the presence or absence of the pathogen. The entire system can be multiplexed for a point of care setting.

Given below are examples of probes for the detection of N. *Gonorrhoeae*.

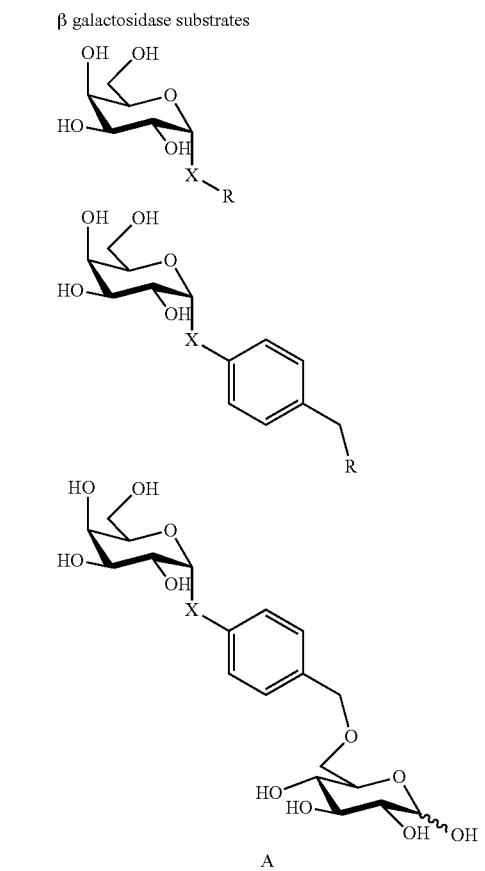

R=D-Glucose or D-Galactose or any other electrochemically active moiety (e.g., —OCH$_2$CH$_3$). D-glucose and D-galactose have 5 hydroxyl groups. In the above example, attachment is at position 6 of glucose. However, attachment can be made any hydroxyl group (e.g., at the 2, 3, or 4 position).

Mechanism

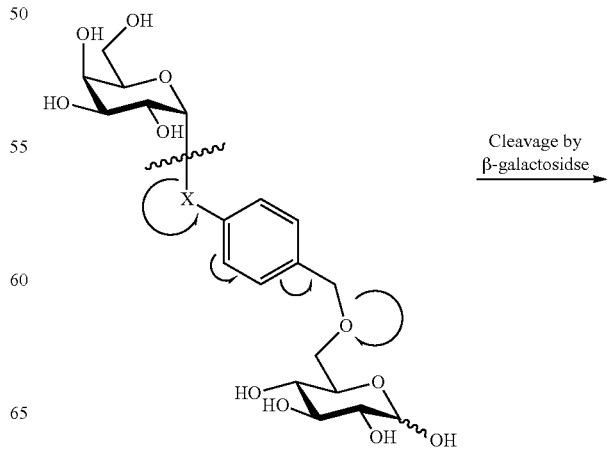

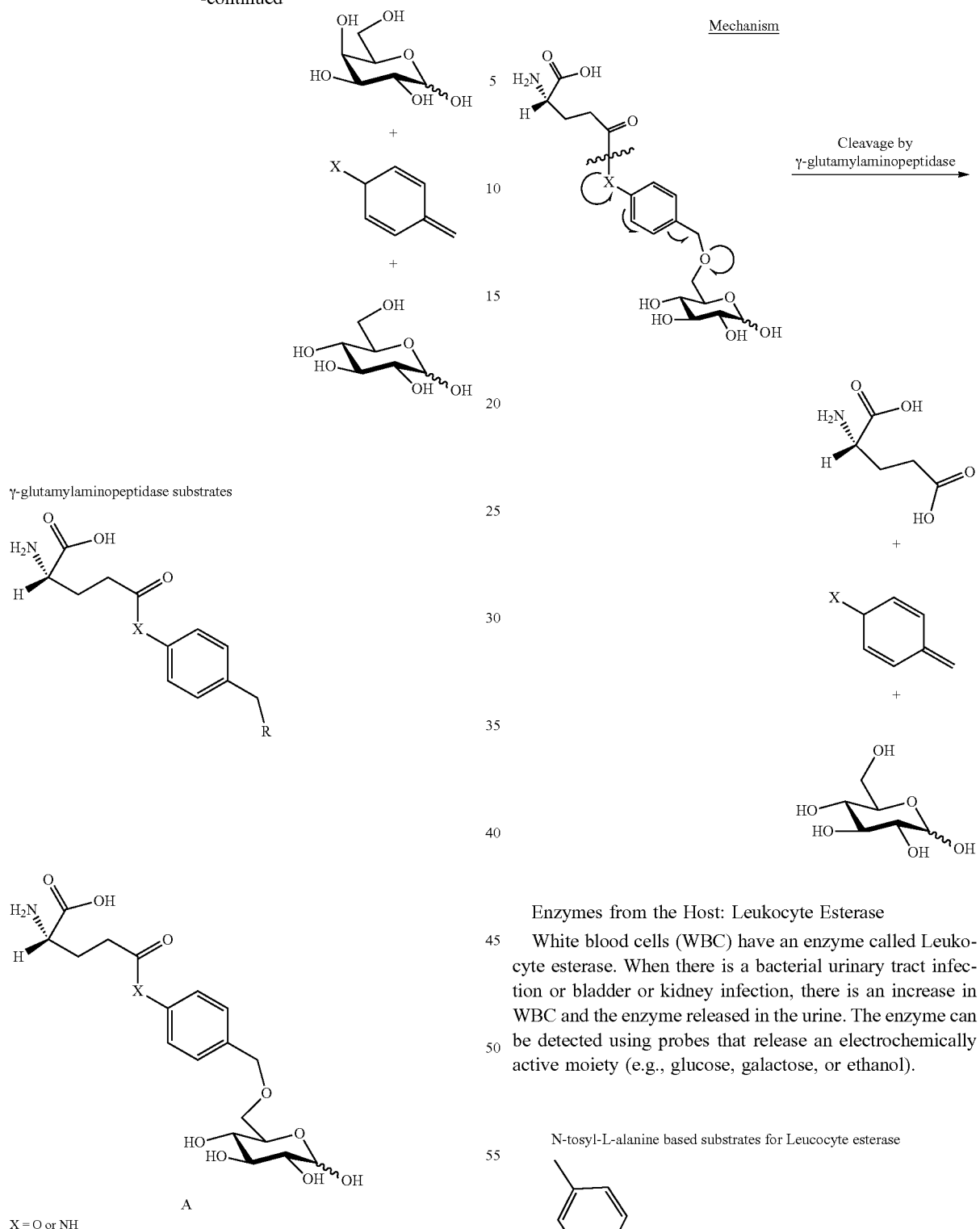

γ-glutamylaminopeptidase substrates

A

X = O or NH

R=D-Glucose or D-Galactose or any other electrochemically active moiety (e.g., —OCH$_2$CH$_3$). D-glucose and D-galactose have 5 hydroxyl groups. In the above example, attachment is at position 6 of glucose. However, attachment can be made any hydroxyl group (e.g., at the 2, 3, or 4 position).

Enzymes from the Host: Leukocyte Esterase

White blood cells (WBC) have an enzyme called Leukocyte esterase. When there is a bacterial urinary tract infection or bladder or kidney infection, there is an increase in WBC and the enzyme released in the urine. The enzyme can be detected using probes that release an electrochemically active moiety (e.g., glucose, galactose, or ethanol).

N-tosyl-L-alanine based substrates for Leucocyte esterase

-continued

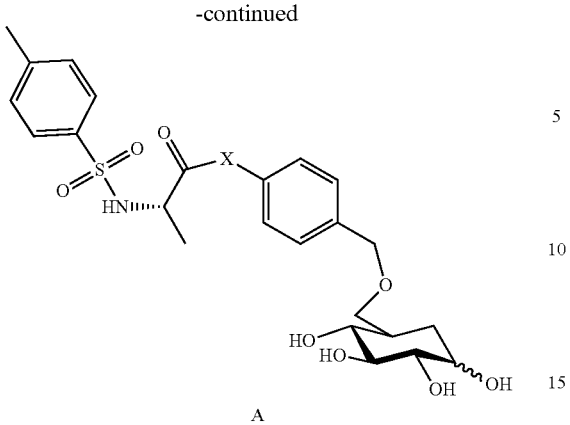

A

R=D-Glucose or D-Galactose or any other electrochemically active moiety (e.g., —OCH$_2$CH$_3$). D-glucose and D-galactose have 5 hydroxyl groups. In the above example, attachment is at position 6 of glucose. However, attachment can be made any hydroxyl group (e.g., at the 2, 3, or 4 position). In one example, X=O or NH.

Beta Lactamase Substrates

Beta lactamases are enzymes released by pathogens. They destroy beta lactam antibiotics e.g. penicillin derivatives (penams), cephalosporins (cephems), monobactams, and carbapenems. Example probes for beta lactamases are illustrated below.

Beta lactamase substrates

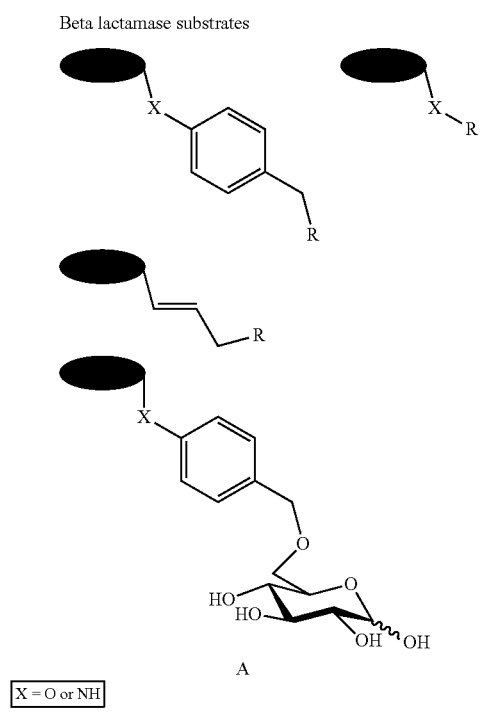

A

X = O or NH

R=D-Glucose or D-Galactose or any other electrochemically active moiety (e.g., —OCH$_2$CH$_3$). D-glucose and D-galactose have 5 hydroxyl groups. In the above example, attachment is at position 6 of glucose. However, attachment can be made any hydroxyl group (e.g., at the 2, 3, or 4 position). In one example, X=O or NH.

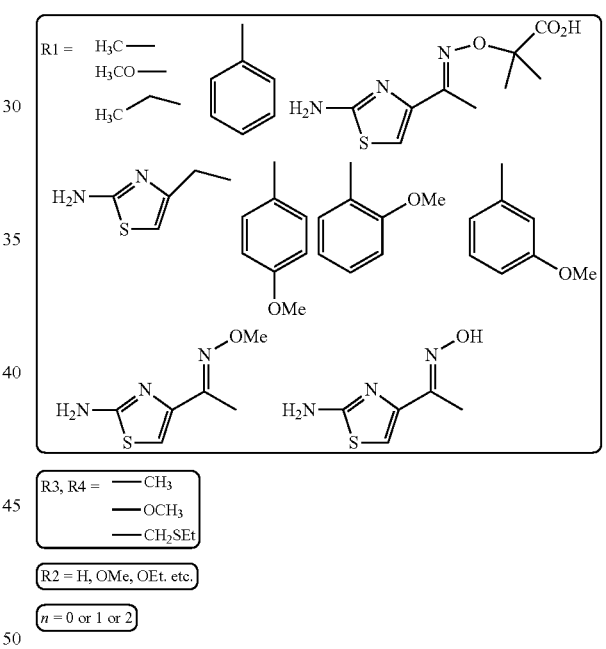

R2 = H, OMe, OEt. etc.

n = 0 or 1 or 2

Glycosidases:

Glycosidases are produced by a number of pathogens. Examples of probes are given below.

Glycosidase substrate

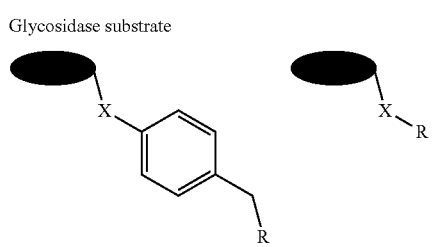

-continued

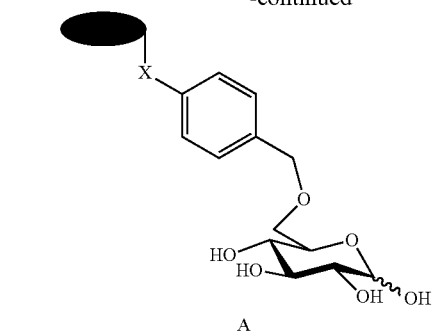

X = O or NH

R=D-Glucose or D-Galactose or any other electrochemically active moiety (e.g., —OCH$_2$CH$_3$). D-glucose and D-galactose have 5 hydroxyl groups. In the above example, attachment is at position 6 of glucose. However, attachment can be made any hydroxyl group (e.g., at the 2, 3, or 4 position). In one example, X=O or NH.

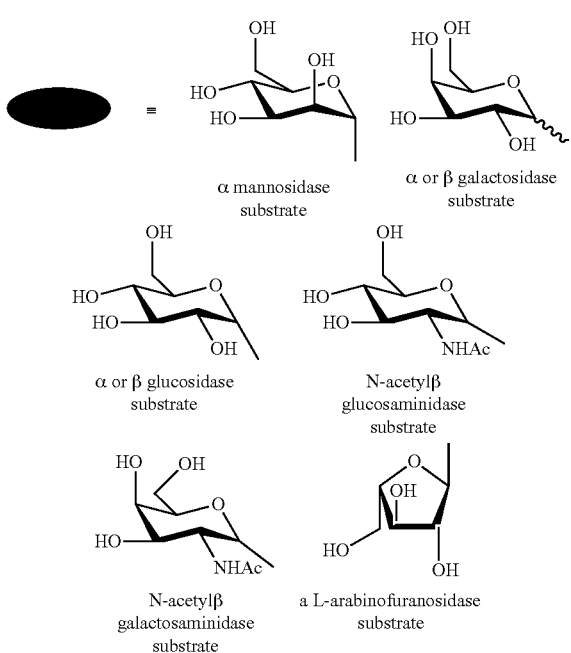

-continued

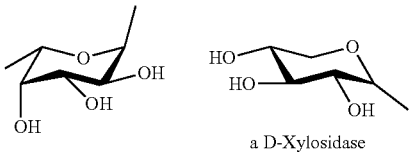

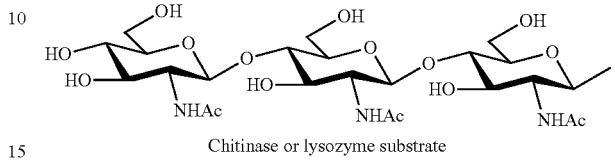

Chitinase or lysozyme substrate

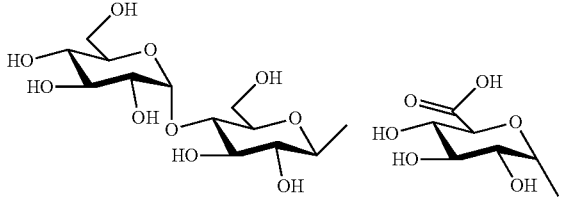

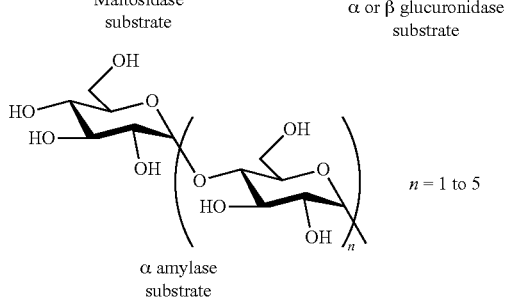

α amylase substrate

In some embodiments, the disclosed compounds can release multiple electrochemical molecules upon cleavage by a single enzyme to improve sensitivity. Such probes include a substrate for an enzyme covalently linked to a plurality of electrochemically active moieties via a polyvalent linker, such that the probe releases a plurality of electrochemically active moieties when cleaved by an enzyme. A representative example of such as probe is given below. Such probes can provide for enhanced sensitivity, as each enzymatic cleavage releases multiple electrochemically active moieties.

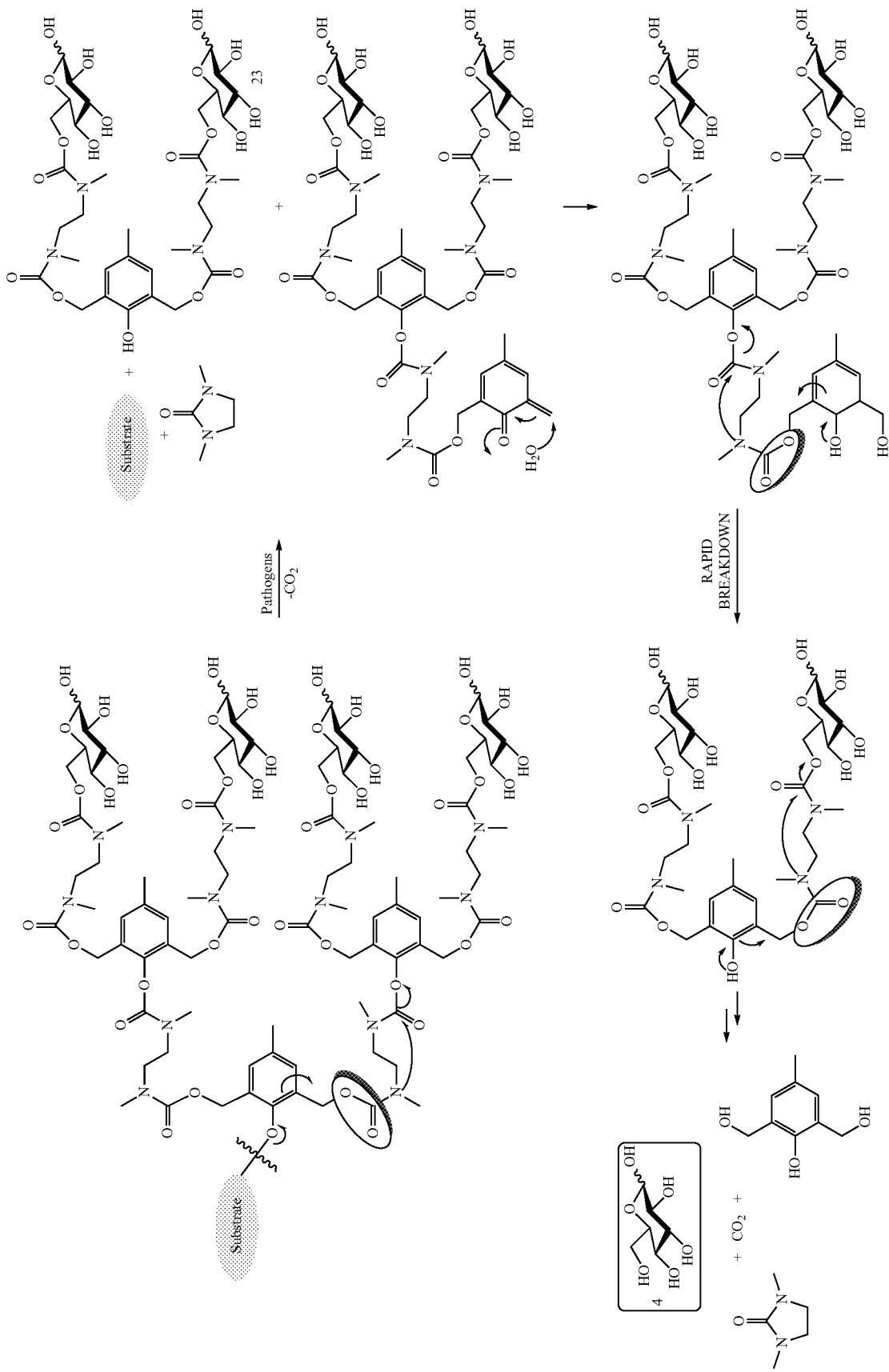

Example 4: Substrates that Will Release Ethanol on Reaction with an Enzyme Present in a Pathogen or a Host Example probes that release ethanol upon reaction with an enzyme are prepared. Probes containing glucuronic acid as the enzyme substrate are prepared for purposes of initial investigation; however, analogous probes employing sialic acid as the enzyme substrate can also be prepared. Following incubation with an appropriate enzyme for the substrate, the liberated ethanol could be detected electrochemically. To validate this methodology, the liberated ethanol can also detected using a standard fluorescence-based assay.

Materials and Methods

Glycosylation reactions are performed under argon with solvents dried using a solvent purification system Innovative Technology. All chemical reagents are of analytical grade, used as supplied without further purification unless indicated. The acidic ion exchange resin used was Amberlite®IR 120 (H+) resin. Analytical thin layer chromatography (TLC) is performed on silica gel 230-400 mesh (Sicicycle). Plates are visualized under UV light, and/or by staining with acidic $CeH_8Mo_3N_2O_{12}$ followed by heating. Column chromatography is performed on silica gel (230-400 mesh). $^1H$ and $^{13}C$ NMR spectra are recorded on Bruker 400 MHz spectrometer. Chemical shifts are reported in δ (ppm) units using $^{13}C$ and residual $^1H$ signals from deuterated solvents as references. Spectra are analyzed with MestreNova® (Mestrelab Research). Electrospray ionization mass spectra are recorded on a Micromass Q\T 2 (Waters) and data were analyzed with MassLynx® 4.0 (Waters) software. Reported yields refer to spectroscopically and chromatographically pure compounds that are dried under high vacuum ($10^{-2}$ mbar) before analytical characterization, unless otherwise specified.

Abbreviations: Silver (I) Oxide $Ag_2O$; Ethyl acetate, EtOAc; Dichloromethane, DCM; TLC; Methanol, MeOH.

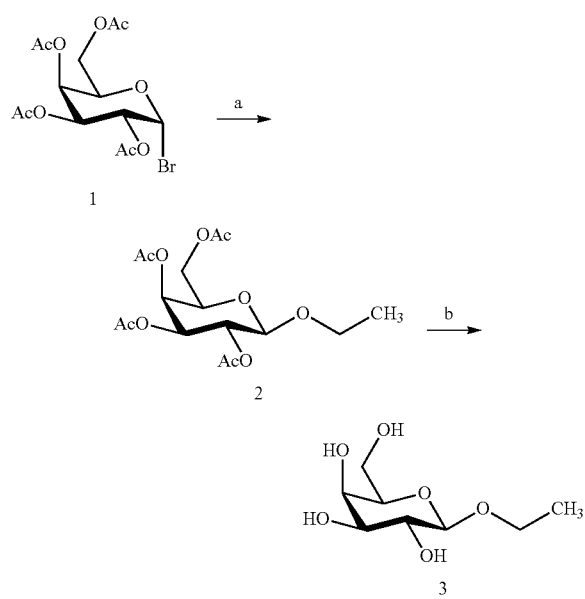

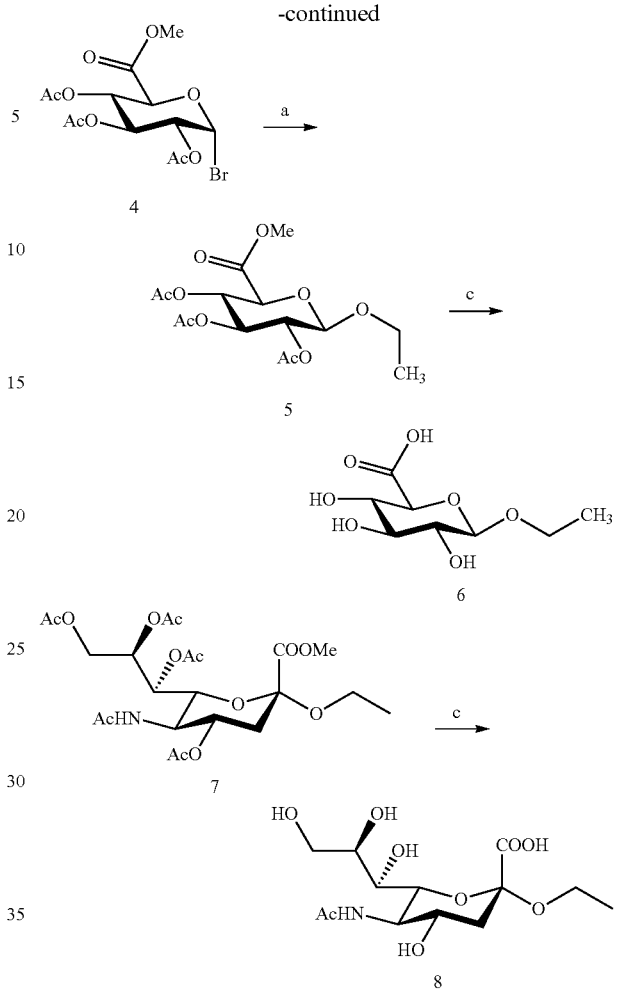

Scheme 5. (a) EtOH, $Ag_2O$, rt, 12 h, 60-65%; (b) NaOMe, MeOH, rt, 1 h, quant.; (c) LiOH, MeOH:THF:$H_2O$, rt, 1-2 h, quant.

(2,3,4,6-Tetra-O-acetyl-1-O-ethyl-3-D-galactopyranoside (2)

To a solution of bromide 1 (0.82 g, 2.00 mmol) in $CH_3CN$ (10 mL) is added $Ag_2O$ (0.69 g, 3.00 mmol) and stirred for 12 h at room temperature in dark. The reaction mixture is filtered through short bed of celite washed with $CH_2Cl_2$ (100 mL) and concentrated on reduced pressure. The crude is purified by column chromatography (eluent: EtOAC/hexane; 1:1) to obtain 2 (0.45 g; 60%) as a white solid. $^1H$ NMR (400 MHz, $CDCl_3$) δ 5.25 (d, J=3.1 Hz, 1H), 5.05 (dd, J=10.4, 8.0 Hz, 1H), 4.90 (dd, J=10.5, 3.4 Hz, 1H), 4.38 (d, J=7.9 Hz, 1H), 4.10-3.96 (m, 2H), 3.86-3.74 (m, 2H), 3.47 (dd, J=9.7, 7.1 Hz, 1H), 2.02 (s, 3H), 1.92 (d, 6H), 1.84 (s, 3H), 1.08 (t, J=7.1 Hz, 3H); $^{13}C$ NMR (101 MHz, $CDCl_3$) δ 170.1, 170.1, 169.9, 169.2, 100.9, 77.6, 77.2, 76.9, 70.8, 70.4, 68.8, 67.0, 65.4, 61.2, 20.6, 20.5, 20.4, 14.9 ppm.

1-O-Ethyl-β-D-galactopyranoside (3)

To a solution of 2 (0.19 g, 0.50 mmol) in MeOH (5.00 mL) is added NaOMe (5.4 M, 100 µl) and stirred at rt for 1 h. Reaction is neutralized with Dowex H+ resin, filtered and concentrated on reduced pressure. The crude is purified by size exclusion P-2 column and fridge dried to get 3 (0.095 g, 91%) as a white solid. $^1$H NMR (400 MHz, D$_2$O) δ 4.29 (d, J=7.9 Hz, 1H), 3.92-3.84 (m, 1H), 3.81 (d, J=2.6 Hz, 1H), 3.70-3.50 (m, 5H), 3.39 (t, J=8.9 Hz, 1H), 1.13 (t, J=7.1 Hz, 3H); $^{13}$C NMR (101 MHz, D$_2$O) δ 102.4, 75.1, 72.8, 70.7, 68.6, 66.1, 60.9, 14.3.

Methyl-2,3,4-tri-O-acetyl-1-O-ethyl-β-D-glucopyronuronate (5)

To a solution of bromide 4 (1.00 g, 2.52 mmol) in CH$_3$CN (10 mL) is added Ag$_2$O (0.92 g, 4.00 mmol) and stirred for 12 h at room temperature in dark. The reaction mixture is filtered through short bed of celite washed with CH$_2$Cl$_2$ (100 mL) and concentrated on reduced pressure. The crude is purified by column chromatography (eluent: EtOAC/hexane; 1:1) to obtain 5 (0.59 g; 65%) as a white solid. $^1$H NMR (400 MHz, CDCl$_3$) δ 5.06-5.16 (m, 2H), 4.87 (t, J=8.0, 1H), 4.49 (d, J=8.0 Hz, 1H), 3.97 (d, J=8.0 Hz, 1H), 3.77-3.86 (m, 1H), 3.64 (s, 3H), 3.40-3.50 (m, 1H), 1.93 (s, 3H), 1.91 (s, 3H), 1.90 (s, 3H), 1.08 (t, J=6.8 Hz, 3H); $^{13}$C NMR (101 MHz, CDCl$_3$) δ 169.9, 169.2, 169.1, 167.2, 100.3, 72.4, 72.0, 71.2, 69.4, 65.6, 52.7, 20.4, 20.3, 14.8 ppm.

1-O-Ethyl-β-D-glucuronic Acid (6)

To a solution of 5 (0.18 g, 0.50 mmol) in MeOH (5.00 mL) is added NaOMe (5.4 M, 100 μl) and stirred at rt for 1 h. Reaction is neutralized with Dowex H$^+$ resin, filtered and concentrated on reduced pressure. The crude is purified by size exclusion P-2 column and fridge dried to get 6 (0.10 g, 90%) as a white solid. $^1$H NMR (400 MHz, D$_2$O) δ 4.38 (d, J=8.0 Hz, 1H), 3.84 (d, J=7.5 Hz, 1H), 3.73 (d, J=8.8 Hz, 1H), 3.60 (s, 1H), 3.43 (dd, J=13.1, 7.1 Hz, 2H), 3.20 (d, J=8.1 Hz, 1H), 1.11 (t, J=7.0 Hz, 3H); $^{13}$C NMR (101 MHz, D$_2$O) δ 174.3, 101.8, 75.4, 75.3, 72.8, 71.5, 66.3, 14.2.

Electrochemical Detection of Ethanol

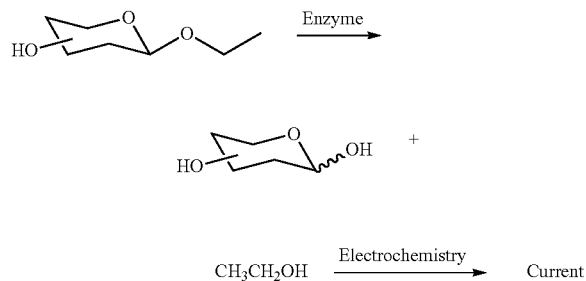

Electrochemical Assay Using the 3 Electrode System

A similar three electrode system is used for proof-of-principle study. Briefly, the working electrode is coated with a coating solution by mixing 2 ml of solution A (2 mM Bi(NO$_3$). 5H$_2$O and 3 mM SeO$_2$ in 1:20 diluted nitric acid) and 4 ml of solution B (2 mM K$_3$Fe(CN)$_6$, 2 mM FeCl$_3$, 0.1M KCl and 10 mM HCl) followed by cyclic voltammetry scanning from +0.60 V to −0.20 V at 20 mVs$^{-1}$ for 30 cycles. After the coating, the working electrode is activated by cycling from 0.35 V to −0.05 V at 50 mVs$^{-1}$ for 30 times in solution C (0.1M KCl and 10 mM HCl). 5 mg of alcohol oxidase is dissolved in 1 mL of 0.5% chitosan solution and the resulting alcohol oxidase (10 μL) solution is dropped on the surface of the electrode to form an alcohol oxidase layer. The alcohol oxidase layer is air dried to form a firm coated layer on the working electrode.

A solution of enzymes (β-galactosidase, β-glucoronidase, β-lactamase, and NA, 100 μL) is then added to a solution of probe (100 μL, 2 mM in DI water). The resulting mixture is incubated at 37° C. for 1 h. The three electrode system is then used to electrochemically measure the amount of ethanol in 20 μL of this solution.

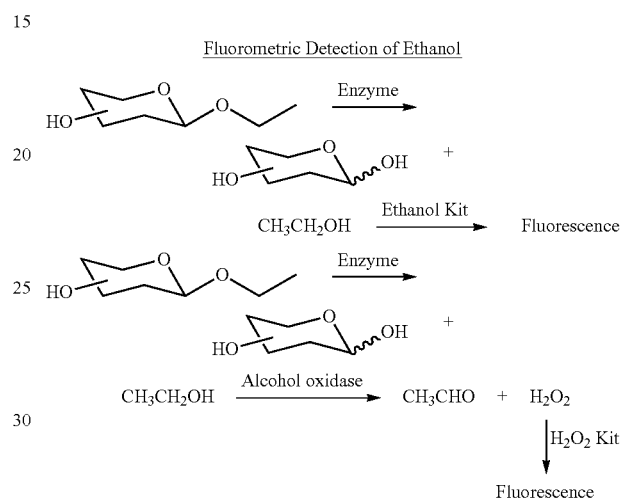

Ethanol Standards for Fluorometric Detection

Ethanol standard solutions for fluorometric detection are prepared via serial dilution. Briefly, 50 μL of a 17.15 N ethanol standard is diluted with 808.7 μL of ethanol assay buffer to generate a 1 μmol/μL standard solution. 10 μL of the 1 μmol/μL standard solution is diluted with 990 μL of ethanol assay buffer to generate a 10 nmol/μL standard solution. 10 μL of the 10 nmol/μL standard solution is diluted with 990 μL of ethanol assay buffer to generate a 0.1 nmol/μL solution. 0, 2, 4, 6, 8, 10 μL of the 0.1 nmol/μL standard solution is then added into a 96 well plate, and ethanol assay buffer is added to each well to bring the volume to 50 μL. 50 μL of the Master Reaction Mix (containing 46 μL ethanol assay buffer, 2 μL ethanol probe, and 2 μL ethanol enzyme mix) is then added to each of the wells. The wells are then mixed with a pipet, and the samples are incubated for 1 h at room temperature. The fluorescence intensity of each sample is then measured ($\lambda_{ex}$=535/$\lambda_{em}$=587 nm).

Sample Measurements

Probe is dissolved in ethanol assay buffer to generate a 40 μM probe solution. 25 μL probe solution, 25 μL enzymes (5 units, 200 u/ml), and 50 L Master Reaction Mix are added to each well. The resulting solution is mixed well using a pipette, and incubated at 37° C. for 1 h. The fluorescence intensity of each sample is then measured ($\lambda_{ex}$=535/$\lambda_{em}$=587 nm).

Example 5: Detection of Hydrolases

Materials and Methods

Glycosidases are important enzymes that degrade oligosaccharides and the glycan components of glycoproteins and glycolipids. These hydrolyases catalyze the cleavage of glycoside bonds and have been widely used in a number of industrial applications, such as food processing, wood processing for paper and pulp products and as catalysts to form glycosidic bonds via transglycosylation or reverse hydrolysis. Numerous bacteria, fungi, parasites and viruses, express glycosidases to degrade glyco oligo/polymers. Glycosidases are also excreted in bodily fluids. Therefore, detection of glycosidases are often used to report presence/absence of a pathogen or indicate disease states. For example, detection of coliforms in drinking water, recreational pools and other sources is performed by testing for β-galactosidase and/or β-glucuronidase. In a different study, detection of α-mannosidase has been used to identify *Chlamydia trachomatis* infections.

Experimental

Glycosylation reactions were performed under argon with solvents dried using a solvent purification system Innovative Technology. All chemical reagents were of analytical grade, used as supplied without further purification unless indicated. The acidic ion exchange resin used was Amberlite®IR 120 (H$^+$) resin. Analytical thin layer chromatography (TLC) was performed on silica gel 230-400 mesh (Sicicycle). Plates were visualized under UV light, and/or by staining with acidic $CeH_8Mo_3N_2O_{12}$ followed by heating. Column chromatography was performed on silica gel (230-400 mesh). $^1$H and $^{13}$C NMR spectra were recorded on Bruker 400 MHz spectrometer. Chemical shifts are reported in δ (ppm) units using $^{13}$C and residual $^1$H signals from deuterated solvents as references. Spectra were analyzed with MestreNova® (Mestrelab Research). Electrospray ionization mass spectra were recorded on a Micromass Q\T 2 (Waters) and data were analyzed with MassLynx® 4.0 (Waters) software. Reported yields refer to spectroscopically and chromatographically pure compounds that were dried under high vacuum (10$^{-2}$ mbar) before analytical characterization, unless otherwise specified.

Abbreviations: Acetic anhydride, $Ac_2O$; Ethyl acetate, EtOAc; Dichloromethane, DCM; Trimethylsilyl trifluoromethanesulfonate, TMSOTf; Dimethyl aminopyridine, DMAP; Thin layer chromatography, TLC; Methanol, MeOH; Copper sulfate pentahydrate, $CuSO_4.5H_2O$; Acetic acid, $CH_3COOH$; Triethyl amine, $NEt_3$.

Scheme 6. General Scheme for the synthesis; Reagents and conditions: a) 6, CH2Cl2, TMSOTf, 0° C., 1 h, 65-75%; b) 6, CH3CN, Ag2O, 12 h, 70%; c) CH2Cl2: MeOH (1:1), NaBH4, 0° C. to rt, 1 h, 75-80%; d) 12, CH2Cl2, TMSOTf, -20° C. - 0° C., 1 h, 60-70%; e) Zn dust CuSO4, Ac2O, AcOH, rt, 3 h, 65%; f) Ethylenediamine, MeOH, reflux, 4 h, 70%; g) MeOH, NaOMe, rt, 1 h, 71-76%

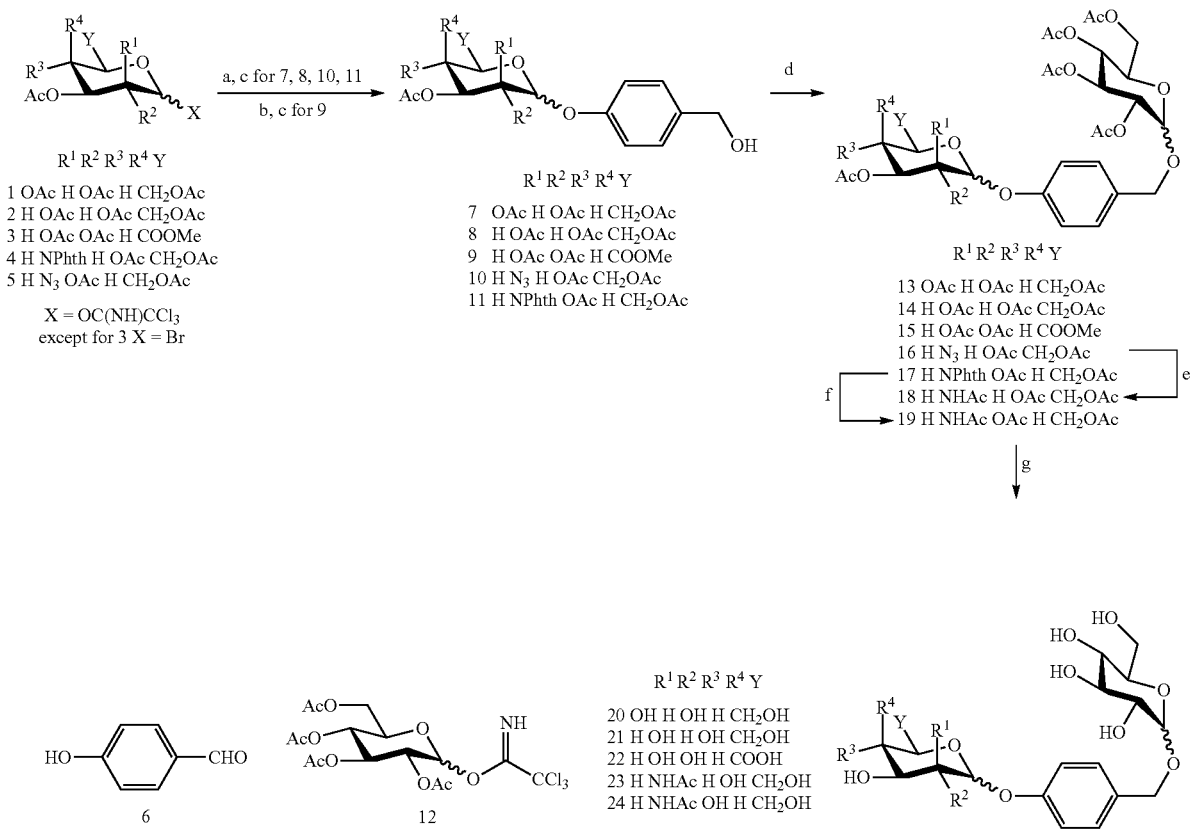

TMSOTf, 0° C., 1 h, 65-75%; b) 6, CH3CN, Ag2O, 12 h, 70%; c) CH2Cl2: MeOH (1:1), NaBH4, 0° C. to rt, 1 h, 75-80%; d) 12, CH2Cl2, TMSOTf, −20° C.-0° C., 1 h, 60-70%; e) Zn dust, CuSO4, Ac2O, AcOH, rt, 3 h, 65%; f) Ethylenediamine, MeOH, reflux, 4 h, 70%; g) MeOH, NaOMe, rt, 1 h, 71-76%.

[4-(hydroxymethyl)phenyl]-(2,3,4,6-tetra-O-acetyl-α-D-mannopyranoside) (7): General Procedure A To a cooled (0° C.) solution of p-hydroxy benzaldehyde (6, 0.05 g, 0.41 mmol) and mannose trichloroacetimidate 1[1] (0.40 g, 0.82 mmol) in DCM (7.00 mL), TMSOTf (10 µL, 0.04 mmol) was added, and stirred at 0° C. for 1 h (monitored by TLC). The reaction was quenched by the addition of Et$_3$N (0.10 mL) and the reaction mixture was concentrated. Crude product was purified by chromatography (EtOAc:hexane, 1:3) to give aldehyde (0.12 g, 65%) as a gummy liquid.[2] To a cooled solution (0° C.) of aldehyde (0.10 g, 0.22 mmol) in CH$_2$Cl$_2$ (5 ml) and MeOH (5 ml) was added sodium borohydride (0.02 g, 0.52 mmol). The reaction mixture was stirred at 0° C. for 1 h, and then allowed to warm to room temperature, after which 1N HCl was added and concentrated under reduced pressure. The crude was diluted with CH$_2$Cl$_2$ (50 mL) and the organic layer was washed with water (50 mL), NaHCO$_3$ (50 mL) and dried on anhydrous Na$_2$SO$_4$. The solvent was evaporated under reduced pressure and the residue was purified by flash column chromatography over silica (EtOAc/hexanes, 1:1) to give 7 (0.08 g, 80%) as a gummy liquid. Analytical data for 6 is complies with reported in the literature.[2]

(2,3,4,6-tetra-O-acetyl-α-D-mannopyranosyloxy)-1-benzyloxy]-2,3,4,6-tetra-O-acetyl-1-α/β-D-glucopyranoside (13)

General procedure B: To a cooled (−20° C.) solution of acceptor 7 (0.05 g, 0.11 mmol) and glucose trichloroacetimidate 12[3] (0.10 g, 0.20 mmol) in DCM (5.00 mL), TMSOTf (3 µL, 0.01 mmol) was added, and stirred at 0° C. for 1 h (monitored by TLC). The reaction was quenched by the addition of Et$_3$N (0.10 mL) and the reaction mixture was concentrated. Crude product was purified by chromatography (EtOAc:hexane, 1:2) to give 13 (0.05 g, 60%, a/(3, 1:2) as a gummy liquid. 1H NMR (CDCl$_3$, 400 MHz): 7.21-7.39 (m, 2H, Ar H), 7.01-7.20 (m, 2H, Ar H), 6.31 (d, 0.5H, J=3.6 Hz, anomeric H α-glucose), 5.70 (d, 1H, J=8.0 Hz, anomeric 3-glucose), 5.20-5.60 (m, 6H), 4.95-5.17 (m, 2H), 4.47 (d, $^1$H, J=5.6 Hz), 4.2-4.45 (m, 3H), 4.07-4.16 (m, 5H), 3.83 (d, 1H, J=8.0 Hz), 1.90-2.25 (in, 38H) ppm; $^{13}$C NMR (CDCl$_3$, 100 MHz): 171.6 170.5, 170.1, 169.9, 169.4, 169.2, 168.9, 130.0, 129.2, 116.9, 116.5, 95.8, 91.6, 89.0, 72.7, 72.6, 70.2, 69.8, 69.3, 69.1, 68.8, 67.8, 67.7, 65.8, 62.0, 61.4, 60.4, 20.85, 20.78, 20.7, 20.5 ppm; HRMS (ESI): m/z: calcd for C$_{35}$H$_{44}$O$_{20}$ [M+H$_3$O]+: 803.2610; found 803.2240.

(α-D-mannopyranosyloxy)-1-benzyloxy]-1-α/β-D-glucopyranoside (20)

General procedure C: To a solution of 13 (0.05 g, 0.06 mmol) in MeOH (5.00 mL) was added NaOMe (5.4 M, 50 µl) and stirred at rt for 1 h. Reaction was neutralized with Dowex H$^+$ resin, filtered and concentrated under reduced pressure. The crude was purified by size exclusion P-2 column and freeze dried to get 20 (0.02 g, 71%, a/β, 1:2) as a white foam. 1H NMR (D$_2$O, 400 MHz): δ 7.25 (dd, J=19.5, 8.6 Hz, 2H), 7.05 (dd, J=11.5, 8.7 Hz, 2H), 5.51 (dd, J=10.0, 1.7 Hz, 1H), 5.14 (d, J=3.8 Hz, 1H), 4.55 (d, J=7.9 Hz, 1H), 4.49 (s, 1H), 4.36 (s, 1H), 4.07 (ddd, J=5.2, 3.4, 1.8 Hz, 1H), 3.94 (dd, J=9.0, 3.7 Hz, 1H), 3.80 (dd, J=12.3, 2.1 Hz, 1H), 3.77-3.71 (m, 1H), 3.64 (ddd, J=12.8, 6.1, 3.6 Hz, 4H), 3.46-3.41 (m, 1H), 3.39-3.29 (m, 2H), 3.15 (dd, J=9.1, 8.0 Hz, 1H) $^{13}$C NMR (101 MHz, D$_2$O) δ 155.6, 131.3, 128.8, 117.5, 97.3, 95.9, 92.1, 75.9, 75.7, 74.1, 72.7, 71.6, 69.6, 69.4, 69.1, 68.1, 61.0, 60.7, 60.6, 44.0; HRMS (ESI): m/z: calcd for C$_{19}$H$_{28}$O$_{12}$Na [M+Na]$^+$: 471.1478; found 471.1459.

[4-(hydroxymethyl)phenyl]-(2,3,4,6-tetra-O-acetyl-α-D-galactopyranoside) (8a)

8a was synthesized by general procedure A: $^1$H NMR (400 MHz, CDCl$_3$) δ 7.29 (d, J=8.3 Hz, 2H), 7.04 (d, J=8.2 Hz, 2H), 5.75 (d, J=3.3 Hz, 1H), 5.62-5.45 (m, 2H), 5.27 (dd, J=10.7, 3.4 Hz, 1H), 4.61 (s, 2H), 4.34 (t, J=6.5 Hz, 1H), 4.08 (qd, J=11.2, 6.8 Hz, 2H), 2.24 (s, 1H), 2.15 (d, J=10.9 Hz, 3H), 2.11-1.98 (m, 7H), 1.94 (s, 3H); $^{13}$C NMR (101 MHz, CDCl$_3$) δ 170.44, 170.37, 170.24, 170.10, 155.79, 135.76, 128.49, 116.88, 95.03, 67.88, 67.81, 67.53, 67.12, 64.57, 61.45, 20.65, 20.61 ppm; HRMS (ESI): m/z: calcd for C$_{21}$H$_{26}$O$_1$Na [M+Na]+: 477.1373; found 477.1377.

(2,3,4,6-tetra-O-acetyl-α-D-galactopyranosyloxy)-1-benzyloxy]-2,3,4,6-tetra-O-acetyl-1-α/β-D-glucopyranoside (14a)

14a was synthesized by General procedure B. $^1$H NMR (400 MHz, CDCl$_3$) δ $^1$H NMR (400 MHz, CDCl$_3$) δ 7.31-7.22 (m, 2H), 7.05 (d, J=8.6 Hz, 2H), 6.32 (d, J=3.7 Hz, 1H, anomeric H), 6.07 (d, J=1.8 Hz, anomeric H), 5.76 (d, J=3.6 Hz, 1H, anomeric H), 5.71 (d, J=8.3 Hz, 1H, anomeric H), 5.60-5.41 (m, 3H), 5.37-5.31 (m, 1H), 5.31-5.20 (m, 2H), 5.17-5.05 (m, 2H), 4.49 (d, J=5.7 Hz, 2H), 4.35-4.22 (m, 2H), 4.14-4.04 (m, 5H), 3.80-3.90 (m, 1H), 2.11-1.99 (m, 24H). $^{13}$C NMR (101 MHz, CDCl$_3$) δ 170.6, 170.4, 170.2, 170.0, 169.4, 156.1, 131.1, 129.3, 117.2, 94.9, 72.7, 72.7, 70.2, 69.8, 69.2, 67.9, 67.7, 67.4, 67.2, 61.4, 61.3, 44.7, 20.6, 20.5; HRMS (ESI): m/z: calcd for C$_{35}$H$_{44}$O$_{20}$Na [M+Na]$^+$: 807.2324; found 807.2294.

(α-D-galactopyranosyloxy)-1-benzyloxy]-1-α/β-D-glucopyranoside (21a)

21a was synthesized by General procedure C. $^1$H NMR (400 MHz, D$_2$O) δ 7.23 (d, J=8.6 Hz, 2H), 7.07 (d, J=8.6 Hz, 2H), 5.55 (d, J=3.7 Hz, 1H), 5.13 (d, J=3.7 Hz, 1H), 4.55 (d, J=7.9 Hz, 1H), 4.35 (s, 2H), 3.94-4.10 (m, 3H), 3.70-3.90 (m, 2H), 3.69-3.57 (m, 3H), 3.45-3.27 (m, 2H), 3.15 (s, 1H); $^{13}$C NMR (101 MHz, D$_2$O) δ 155.6, 131.3, 128.8, 117.5, 97.3, 95.9, 92.1, 75.9, 75.7, 74.1, 72.7, 71.6, 69.6, 69.4, 69.1, 68.1, 61.0, 60.7, 60.6 ppm; HRMS (ESI): m/z: calcd for C$_{19}$H$_{28}$O$_{12}$Na [M+Na]+: 471.1478; found 471.1459.

(2,3,4,6-tetra-O-acetyl-β-D-galactopyranosyloxy)-1-benzyloxy]-2,3,4,6-tetra-O-acetyl-1-α/β-D-glucopyranoside (14b)

14a was synthesized by using acceptor 8a[4] and donor 12 by general procedure B. $^1$H NMR (400 MHz, CDCl$_3$) δ $^1$H NMR (400 MHz, CDCl$_3$) δ 7.22 (d, J=7.1 Hz, 2H), 6.98 (d, J=6.8 Hz, 2H), 5.54-5.42 (m, 3H), 5.22-5.00 (m, 5H), 4.84 (d, J=11.0 Hz, 1H), 4.56 (t, J=9.5 Hz, 1H), 4.33-4.03 (m, 6H), 3.72-3.64 (m, 1H), 2.19 (d, J=1.8 Hz, 3H), 2.12-2.02

(m, 21H); $^{13}$C NMR (101 MHz, CDCl$_3$) δ 170.3, 169.4, 129.3, 116.9, 99.6, 99.2, 72.8, 71.85 71.0, 70.8, 70.2, 68.6, 68.6, 66.8, 61.3, 20.6, 20.6 ppm; HRMS (ESI): m/z: calcd for C$_{35}$H$_{44}$O$_{20}$Na [M+Na]+: 807.2324; found 807.2293.

(β-D-galactopyranosyloxy)-1-benzyloxy]-1-α/β-D-glucopyranoside (21b)

21b was synthesized by General procedure C. $^1$H NMR (400 MHz, D$_2$O) δ $^1$H NMR (400 MHz, D$_2$O) δ 7.34 (d, J=8.6 Hz, 2H), 7.06 (d, J=8.6 Hz, 2H), 4.98 (d, J=7.4 Hz, 1H, anomeric H), 4.80 (d, J=11.5 Hz, 1H), 4.61 (d, J=11.5 Hz, 1H), 4.41 (d, J=8.0 Hz, 1H, anomeric H), 3.91 (d, J=3.1 Hz, 1H), 3.81 (d, J=1.5 Hz, 1H), 3.80-3.58 (m, 7H), 3.39-3.28 (m, 3H), 3.21 (d, J=8.3 Hz, 1H); $^{13}$C NMR (101 MHz, D$_2$O) δ 156.7, 131.1, 130.5, 130.4, 116.5, 101.0, 100.6, 75.9, 75.8, 75.4, 73.1, 72.5, 70.9, 70.5, 69.7, 68.5, 60.7, 48.9 ppm; HRMS (ESI): m/z: calcd for C$_{19}$H$_{28}$O$_{12}$Na [M+Na]+: 471.1478; found 471.1459.

Methyl 1-(4-Hydroxymethylphenyl)-2,3,4-tri-O-acetyl-β-D-glucopyronuronate-2,3,4,6-tetra-O-acetyl-1-α/β-D-glucopyranoside (15)

15 was synthesized by using acceptor 9$^5$ and donor 12 by general procedure B. $^1$H NMR (400 MHz, CDCl$_3$) δ 7.21 (d, J=8.5 Hz, 2H), 6.96 (d, J=8.5 Hz, 2H), 5.38-5.23 (m, 4H), 5.20-4.99 (m, 4H), 4.82 (d, J=12.0 Hz, 1H), 4.54 (t, J=10.4 Hz, 2H), 4.45 (s, 1H), 4.31-4.22 (m, 1H), 4.22-4.06 (m, 3H), 3.72 (s, 3H), 3.66 (dd, J=4.4, 2.4 Hz, 1H), 2.13-1.95 (m, 24H); $^{13}$C NMR (101 MHz, CDCl$_3$) δ 170.6, 170.2, 170.1, 169.4, 169.3, 169.26, 169.2, 166.8, 156.4, 131.8, 129.3, 117.0, 99.2, 99.1, 72.8, 72.6, 71.8, 71.2, 71.0, 70.1, 69.1, 68.4, 61.9, 53.0, 20.6 ppm; HRMS (ESI): m/z: calcd for C$_{34}$H$_{42}$O$_{20}$Na [M+Na]+: 793.2167; found 793.2140.

1-(4-Hydroxymethylphenyl)-β-D-glucopyronuronic acid-1-α/β-D-glucopyranoside (22)

22 was synthesized by general procedure C. $^1$H NMR (400 MHz, D$_2$O) δ 7.33 (d, J=8.6 Hz, 2H), 7.05 (d, J=8.6 Hz, 2H), 5.12-5.08 (m, 1H), 4.43-4.38 (m, 1H), 4.09 (dd, J=5.5, 3.8 Hz, 1H), 3.86-3.76 (m, 2H), 3.66-3.55 (m, 5H), 3.33 (dt, J=7.6, 6.6 Hz, 3H), 3.23-3.17 (m, 1H); $^{13}$C NMR (101 MHz, D$_2$O) δ 172.0, 156.4, 131.48, 130.50, 116.7, 101.0, 100.1, 76.0, 75.8, 75.0, 74.5, 73.1, 72.5, 71.2, 70.9, 69.7, 60.8 ppm; HRMS (ESI): m/z: calcd for C$_{19}$H$_{26}$O$_{13}$Na [M+Na]+: 485.1271; found 485.1252.

[4-(hydroxymethyl)phenyl]-2-azido-(3,4,6-tri-O-acetyl-α-D-galactopyranoside) (10)

10 was synthesized by general procedure A from 5$^6$: $^1$H NMR (400 MHz $^1$H NMR (400 MHz, CDCl$_3$): δ 7.33 (d, J=8.5 Hz, 2H), 7.10 (d, J=8.5 Hz, 2H), 5.63 (d, J=3.4 Hz, 1H), 5.60 (dd, J=11.1, 3.3 Hz, 1H), 5.53 (d, J=2.7 Hz, 1H), 4.64 (s, 2H), 4.36 (t, J=6.6 Hz, 1H), 4.17-4.04 (m, 2H), 3.81 (dd, J=11.1, 3.4 Hz, 1H), 2.18 (s, 3H), 2.10 (s, 3H), 1.97 (s, 3H). $^{13}$C NMR (101 MHz, CDCl$_3$): 20.6, 20.6. HRMS (ES+): Calcd for C$_{19}$H$_{23}$N$_3$O$_9$Na [M+Na] 460.1327, found 460.1338.

2-Acetamido-(3,4,6-tri-O-acetyl-α-D-galactopyranosyloxy)-1-benzyloxy]-2,3,4,6-tetra-O-acetyl-1-α/β-D-glucopyranoside (18)

To a cooled (−20° C.) solution of acceptor 10 (0.05 g, 0.11 mmol) and glucose trichloroacetimidate 12 (0.10 g, 0.20 mmol) in DCM (5.00 mL), TMSOTf (3 µL, 0.01 mmol) was added, and stirred at 0° C. for 1 h (monitored by TLC). The reaction was quenched by the addition of Et$_3$N (0.10 mL) and the reaction mixture was concentrated. Crude product was purified by chromatography (EtOAc:hexane, 1:2) to give 16. To a stirred solution of 16 (35.0 mg, 0.06 mmol), Ac$_2$O (2.0 ml) and CH$_3$COOH (1.0 ml) in THF, Zn dust (0.4 g) was added followed by cat. amount of saturated solution of CuSO$_4$ and reaction was stirred at rt. After completion of reaction, as monitored by TLC, reaction was filtered through cotton, washed with excess THF and coevaporated with toluene. The residue was subjected to flash chromatography (hexanes: Et$_2$OAc 2:8)) to afford 18 (18 mg, 65%).

$^1$H NMR (400 MHz, CDCl$_3$): δ 7.26 (d, J=8.6 Hz, 2H), 7.05 (d, J=8.6 Hz, 2H), 5.77 (d, J=9.5 Hz, 1H), 5.62 (d, J=3.6 Hz, 1H), 5.46 (d, J=2.5 Hz, 1H), 5.41 (dd, J=11.2, 3.2 Hz, 1H), 5.22-5.01 (m, 3H), 4.85 (d, J=11.9 Hz, 1H), 4.77 (dd, J=11.3, 9.5, Hz, 1H), 4.57 (t, J=9.9 Hz, 2H), 4.33-4.25 (m, 2H), 4.20-4.12 (m, 2H), 4.06-4.01 (m, 1H), 3.72-3.67 (m, 1H), 2.20 (s, 3H), 2.12 (s, 3H), 2.06 (s, 4H), 2.03 (s, 6H), 2.01 (s, 3H), 2.00 (s, 3H), 1.95 (s, 3H). $^{13}$C NMR (101 MHz, CDCl$_3$): δ 171.1, 170.6, 170.3, 170.2, 169.4, 169.2, 155.8, 131.3, 129.5, 116.5, 99.2, 96.4, 72.8, 71.9, 71.3, 70.1, 68.4, 68.1, 67.6, 67.1, 61.9, 61.5, 47.9, 23.3, 20.8, 20.7, 20.7, 20.6. HRMS (ES+): Calcd for C$_{35}$H$_{45}$NO$_{19}$ [M+Na] 784.2659, found 784.2690.

2-Acetamido-(α-D-galactopyranosyloxy)-1-benzyloxy]-1-β-D-glucopyranoside (23)

23 was synthesized by general procedure C: $^1$H NMR (400 MHz, D$_2$O): δ 7.35 (d, J=8.5 Hz, 2H), 7.08 (d, J=8.5 Hz, 2H), 5.56 (d, J=3.6 Hz, 1H), 4.80 (d, J=11.5 Hz, 1H), 4.63 (d, J=11.5 Hz, 1H), 4.41 (d, J=8.0 Hz, 1H), 4.27 (dd, J=11.0, 3.6 Hz, 1H), 4.08 (dd, J=11.0, 3.1 Hz, 1H), 4.04-3.99 (m, 2H), 3.83 (d, J=11.9 Hz, 1H), 3.68-3.60 (m, 3H), 3.40-3.28 (m, 3H), 3.27 (s, 1H), 3.20 (t, J=8.5 Hz, 1H), 1.96 (s, 3H). $^{13}$C NMR (101 MHz, D$_2$O) δ 174.7, 156.2, 130.9, 130.5, 117.1, 100.9, 96.1, 75.9, 75.8, 73.07, 71.8, 70.9, 69.6, 68.4, 67.6, 61.0, 60.7, 49.7, 48.8, 21.9. HRMS (ES+): Calcd for C$_{21}$H$_{31}$NO$_{12}$ [M+Na] 512.1738, found, 512.1755.

[4-(hydroxymethyl)phenyl]-2-pthalamido-(3,4,6-tri-O-acetyl-α-D-galactopyranoside) (11)

11 was synthesized by general procedure A from 4$^7$: $^1$H NMR (400 MHz, CDCl$_3$) δ 7.83 (dd, J=5.0, 2.9 Hz, 2H), 7.77-7.68 (m, 2H), 7.19 (d, J=8.5 Hz, 2H), 6.88 (d, J=8.6 Hz, 2H), 5.97 (d, J=8.5 Hz, 1H), 5.87 (dd, J=10.5, 9.3 Hz, 1H), 5.24 (t, J=9.6 Hz, 1H), 4.59 (dd, J=10.6, 8.6 Hz, 1H), 4.54 (s, 2H), 4.34 (dd, J=12.3, 5.2 Hz, 1H), 4.17 (dd, J=12.3, 2.1 Hz, 1H), 4.06-3.99 (m, 1H), 2.08 (s, 3H), 2.04 (s, 3H), 1.88 (s, 3H). $^{13}$C NMR (101 MHz, CDCl$_3$): δ 170.7, 170.2, 169.5, 155.9, 136.0, 134.5, 131.2, 128.3, 123.7, 117.1, 96.3, 72.0, 70.6, 68.8, 64.5, 61.9, 54.5, 21.0, 20.7, 20.6, 20.4.

2-Acetamido-(3,4,6-tri-O-acetyl-α-D-glucopyranosyloxy)-1-benzyloxy]-2,3,4,6-tetra-O-acetyl-1-α/β-D-glucopyranoside (19)

To a cooled (−20° C.) solution of acceptor 11 (0.05 g, 0.11 mmol) and glucose trichloroacetimidate 12 (0.10 g, 0.20 mmol) in DCM (5.00 mL), TMSOTf (3 L, 0.01 mmol) was added, and stirred at 0° C. for 1 h (monitored by TLC). The reaction was quenched by the addition of Et$_3$N (0.10 ml) and the reaction mixture was concentrated. Crude product was purified by chromatography (EtOAc:hexane, 1:2) to give 17.

To a stirred solution of 17 (35 mg, 0.06 mmol), in MeOH (4.0 ml) diethanolamine (1 ml) was added and reaction was stirred at reflux condition. After completion of reaction (3 h), as monitored by TLC, solvent was removed and coevaporated with toluene. The residue was subjected to flash chromatography (hexanes: Et$_2$OAc 2:8)) to afford 19 (15 mg, 70%)

$^1$H NMR (400 MHz, CDCl$_3$) δ 7.21 (d, J=8.4 Hz, 2H), 6.99 (d, J=7.3 Hz, 2H), 5.74 (d, J=8.7 Hz, 1H), 5.54-5.36 (m, 2H), 5.32-5.25 (m, 1H), 5.23-5.01 (m, 5H), 4.85 (dd, J=11.8, 7.9 Hz, 1H), 4.66-4.51 (m, 3H), 4.35-4.23 (m, 2H), 4.22-4.09 (m, 4H), 3.94-3.84 (m, 2H), 3.70-3.66 (m, 1H), 2.12 (s, 3H), 2.09 (s, 3H), 2.07 (s, 3H), 2.06 (s, 3H), 2.03 (s, 3H), 2.02 (s, 3H), 2.01 (s, 3H), 1.97 (s, 3H). $^{13}$C NMR (101 MHz, CDCl$_3$) δ 170.8, 170.7, 170.6, 170.4, 170.3, 170.1, 169.4, 169.3, 156.9, 131.4, 129.5, 129.3, 117.0, 116.9, 99.2, 99.1, 99.0, 94.8, 72.8, 72.1, 71.8, 71.3, 70.3, 68.4, 62.1, 61.9, 54.8, 29.7, 23.3, 20.8, 20.7, 20.7, 20.6, 20.64, 20.61, 20.60. HRMS (ES$^+$): Calcd for C$_{41}$H$_{45}$NO$_{20}$Na (M+Na) 894.2427, found, 894.2460.

2-Acetamido-(α-D-glucopyranosyloxy)-1-benzyloxy]-1-β-D-glucopyranoside (24)

24 was synthesized by general procedure C: $^1$H NMR (400 MHz, D$_2$O): δ 7.34 (d, J=8.6 Hz, 2H), 7.01 (d, J=8.6 Hz, 2H), 5.10 (d, J=8.5 Hz, 1H), 4.92 (d, J=3.8 Hz, 1H), 4.80 (d, J=11.5 Hz, 2H), 4.63 (d, J=11.5 Hz, 2H), 4.42 (d, J=8.0 Hz, 1H), 3.95-3.79 (m, 3H), 3.71 (dd, J=12.4, 5.4 Hz, 1H), 3.67-3.44 (m, 6H), 3.39-3.30 (m, 3H), 3.20 (t, J=8.5 Hz, 1H), 1.95 (s, 3H). $^{13}$C NMR (101 MHz, D$_2$O): 174.9, 156.7, 131.4, 130.5, 116.6, 101.0, 99.5, 97.6, 76.1, 75.92, 75.8, 73.5, 73.1, 70.9, 69.7, 60.8, 60.5, 55.5, 22.1. HRMS (ES$^+$): Calcd for C$_{21}$H$_{31}$NO$_{21}$Na (M+Na) 512.1741.

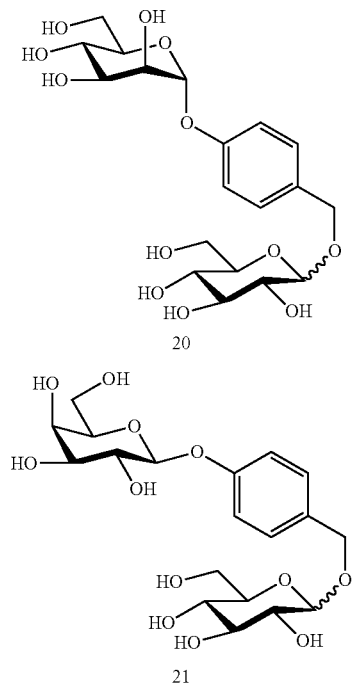

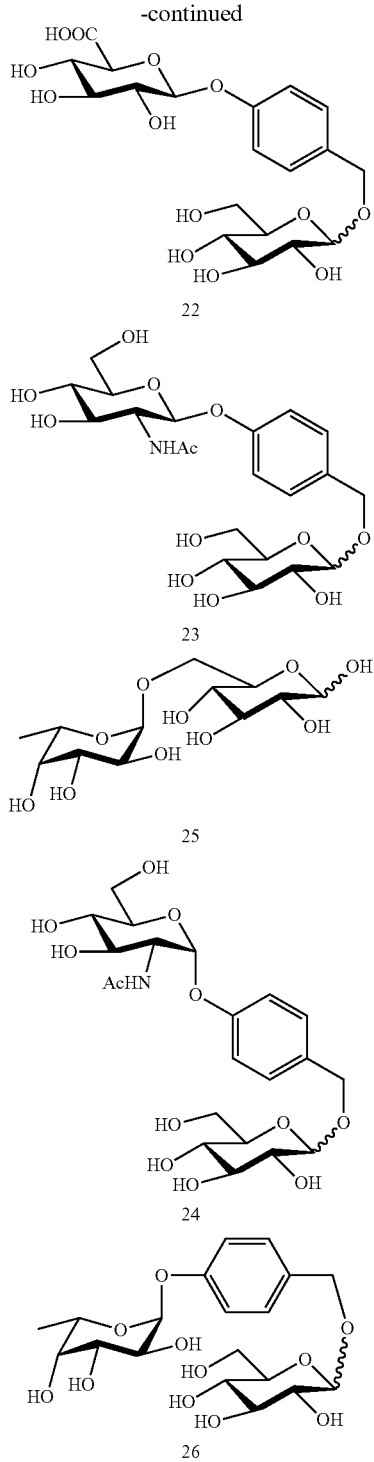

TABLE 4

| Electrochemical detection of 5 enzyme for different substrate. | | |
|---|---|---|
| Enzyme | Substrate[a] | i [10$^{-8}$ A][b] |
| α-Mannosidase | 20 | 81.0 ± 1.8 |
|  | 22 | 12.3 + 1.2 |
| β-Galactosidase | 21 | 77.9 ± 7.3 |
|  | 20 | 10.2 ± 0.6 |

TABLE 4-continued

Electrochemical detection of 5 enzyme for different substrate.

| Enzyme | Substrate[a] | i [10$^{-8}$ A][b] |
|---|---|---|
| β-Glucuronidase | 22 | 65.1 ± 4.6 |
|  | 21 | 10.4 ± 1.3 |
| β-N-Acetylglucosaminidase | 23 | 28.5 ± 4.0 |
|  | 24 | 11.1 ± 2.3 |
| α-L-Fucosidase | 25 | 44.5 ± 2.9 |
|  | 26 | 25.2 ± 2.9 |
|  | 22 | 9.7 ± 3.5 |

[a]Substrate that used to incubated with Enzyme.
[b]Value of Electrochemical assay.

The devices, systems, and methods of the appended claims are not limited in scope by the specific devices, systems, and methods described herein, which are intended as illustrations of a few aspects of the claims. Any devices, systems, and methods that are functionally equivalent are intended to fall within the scope of the claims. Various modifications of the devices, systems, and methods in addition to those shown and described herein are intended to fall within the scope of the appended claims. Further, while only certain representative devices, systems, and method steps disclosed herein are specifically described, other combinations of the devices, systems, and method steps also are intended to fall within the scope of the appended claims, even if not specifically recited. Thus, a combination of steps, elements, components, or constituents may be explicitly mentioned herein or less, however, other combinations of steps, elements, components, and constituents are included, even though not explicitly stated.

The term "comprising" and variations thereof as used herein is used synonymously with the term "including" and variations thereof and are open, non-limiting terms. Although the terms "comprising" and "including" have been used herein to describe various embodiments, the terms "consisting essentially of" and "consisting of" can be used in place of "comprising" and "including" to provide for more specific embodiments of the invention and are also disclosed. Other than where noted, all numbers expressing geometries, dimensions, and so forth used in the specification and claims are to be understood at the very least, and not as an attempt to limit the application of the doctrine of equivalents to the scope of the claims, to be construed in light of the number of significant digits and ordinary rounding approaches.

Unless defined otherwise, all technical and scientific terms used herein have the same meanings as commonly understood by one of skill in the art to which the disclosed invention belongs. Publications cited herein and the materials for which they are cited are specifically incorporated by reference.

What is claimed is:

1. A compound defined by Formula I below

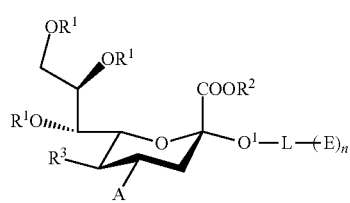

Formula I wherein

A is —OH, —OMe, —OC(═O)CH$_3$, —NH$_2$, —NHC(═O)CH$_3$, —NHCH$_2$OH, or —NHC(═NH)NH$_2$;

R$^1$ is, individually for each occurrence, —H, —Me, or —C(═O)CH$_3$;

R$^2$ is —H or —Me;

R$^3$ is —OH, —OMe, —OC(═O)CH$_3$, —NH$_2$, —NHC(═O)CH$_3$, or —NHCH$_2$OH;

n is an integer from 1 to 16;

L is selected from a polyvalent linking moiety or a bivalent linking moiety comprising

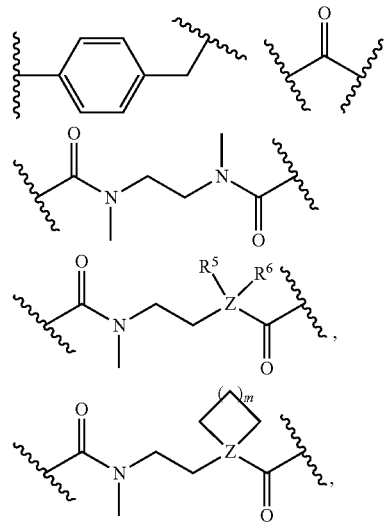

wherein R$^5$ and R$^6$ are independently selected from methyl, ethyl, isopropyl, and tertbutyl; Z is C or S; and m is 0, 1, 2 or 3; and E is, individually for each occurrence, an electrochemically active moiety defined by one of the general formulae shown below

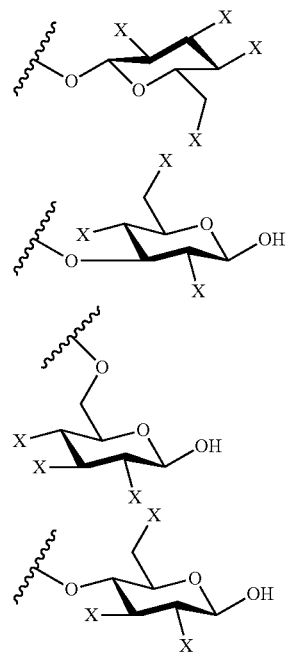

-continued

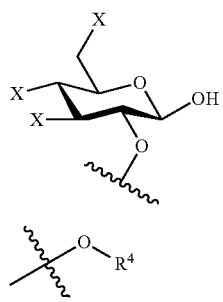

wherein

R⁴ is a $C_1$-$C_6$ alkyl group, and

X is, individually for each occurrence, —OH, —OMe, —OC(=O)CH₃, —F, —CF₃, —CH₂F, —CHF₂, —Cl, —Br, —I, H or sulfonate.

2. The compound of claim 1, wherein E is

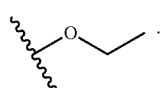

3. The compound of claim 1, wherein E comprises a moiety defined by one of the general formulae below

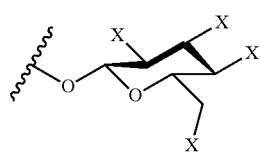

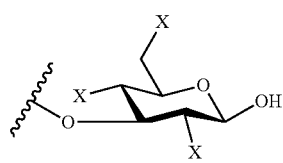

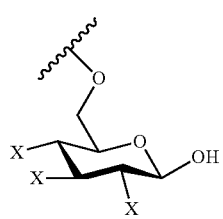

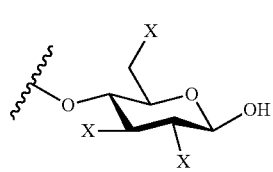

-continued

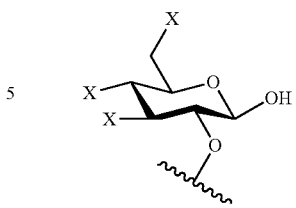

wherein X is, individually for each occurrence, —OH, —OMe, —OC(=O)CH₃, —F, —CF₃, —CH₂F, —CHF₂, —Cl, —Br, —I, H or sulfonate.

4. The compound of claim 3, wherein E comprises a moiety defined the general formula below

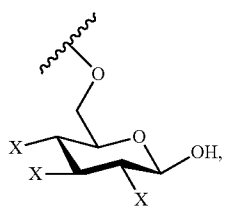

wherein X is, individually for each occurrence, —OH, —OMe, —OC(=O)CH₃, —F, —CF₃, —CH₂F, or —CHF₂.

5. The compound of claim 3, wherein X is, in each occurrence —OH.

6. The compound of claim 1, wherein $R^1$ and $R^2$ are, in each occurrence, —H.

7. The compound of claim 1, wherein A is —OH.

8. The compound of claim 1, wherein $R^3$ is —NHC(=O)CH₃.

9. The compound of claim 1, wherein L is chosen from one of the following

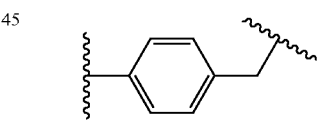

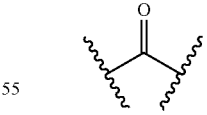

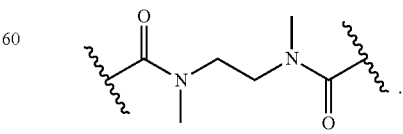

10. The compound of claim 1, wherein L is a polyvalent linking moiety.

11. The compound of claim 1, wherein L is chosen from one of the following

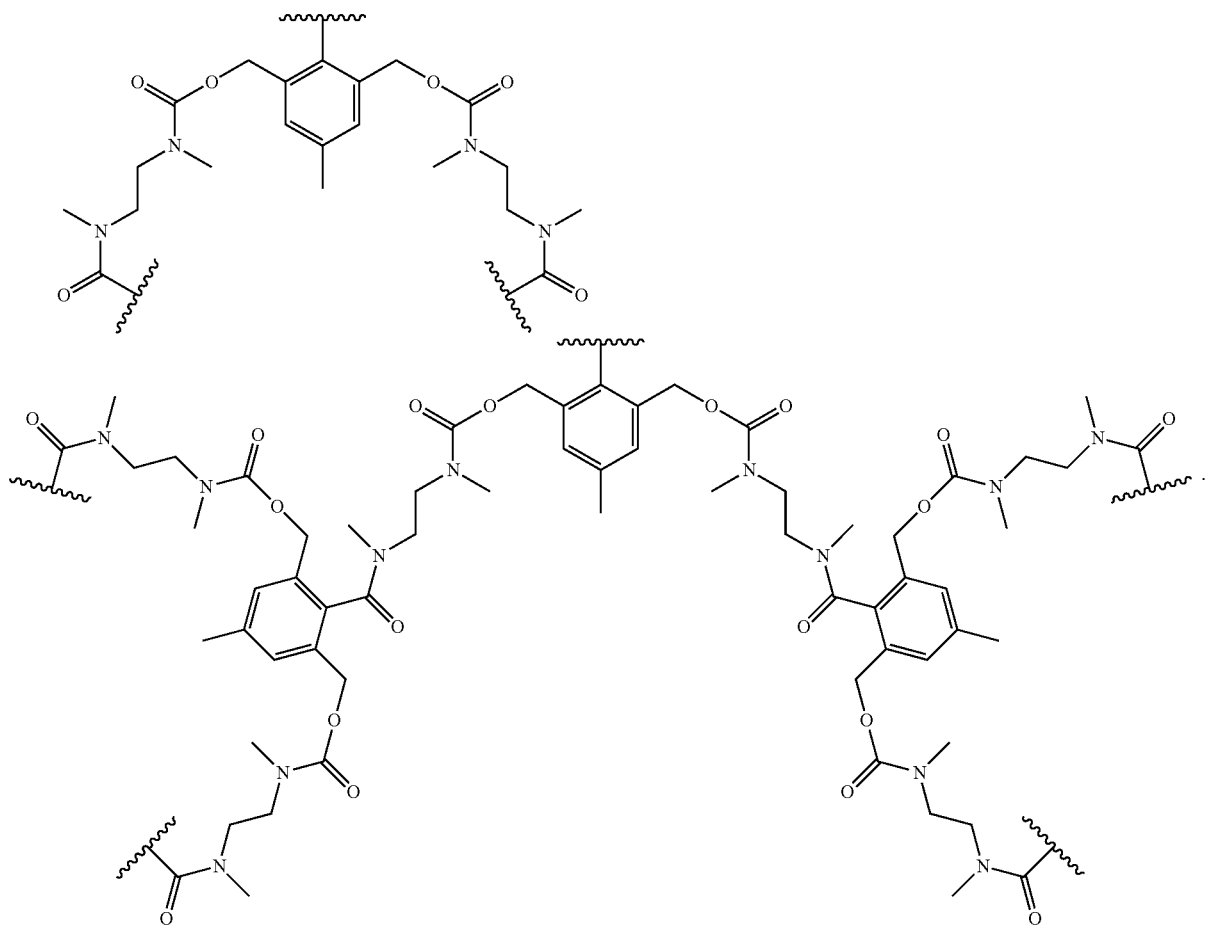

12. The compound of claim 1, wherein n is 1.

13. The compound of claim 1, wherein n is from 2 to 8.

14. A method of electrochemically detecting an enzyme in a sample comprising:
(a) providing a probe comprising a compound defined by Formula I below, having a substrate for the enzyme covalently linked to an electrochemically active moiety via a bond that is cleavable by the enzyme;

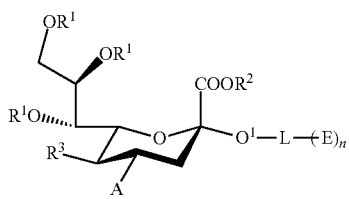

Formula I wherein
A is —OH, —OMe, —OC(=O)CH$_3$, —NH$_2$, —NHC(=O)CH$_3$, —NHCH$_2$OH, or —NHC(=NH)NH$_2$;

R$^1$ is, individually for each occurrence, —H, -Me, or —C(=O)CH$_3$;

R$^2$ is —H or -Me;

R$^3$ is —OH, —OMe, —OC(=O)CH$_3$, —NH$_2$, —NHC(=O)CH$_3$, or —NHCH$_2$OH;

n is an integer from 1 to 16;

L is absent or is a linking moiety, wherein when L is absent, 01 is also absent and n is 1; and E is, individually for each occurrence, an electrochemically active moiety defined by one of the general formulae shown below

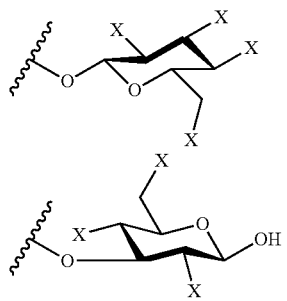

-continued

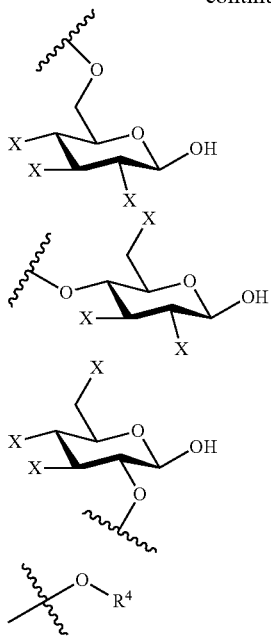

wherein
R$^4$ is a C$_1$-C$_6$ alkyl group, and
X is, individually for each occurrence, —OH, —OMe, —OC(=O)CH$_3$, —F, —CF$_3$, —CH$_2$F, —CHF$_2$, —Cl, —Br, —I, H or sulfonate, (b) contacting the sample with the probe under conditions effective for enzymatic cleavage of the bond by the enzyme;
(c) electrochemically detecting the electrochemically active moiety enzymatically cleaved by the enzyme.

15. The method of claim 14, wherein the enzyme is a pathogen-specific enzyme selected from a viral neuraminidase, a reverse transcriptase or protease, an isoform of β-lactamase sulfatase, a β-glucuronidase, a carbapenamase, a lysyl aminopeptidase, or an α mannoside.

16. The method of claim 14, wherein the enzyme is a pathogen-specific enzyme selected from a peptidase, sulfatase, phosphatase, esterase, or combination thereof.

17. A kit comprising:
(i) a device for collecting a sample comprising an enzyme of interest; and
(ii) a probe comprising a compound defined by Formula I below, having a substrate for the enzyme of interest covalently linked to an electrochemically active moiety via a bond that is cleavable by the enzyme, Formula I

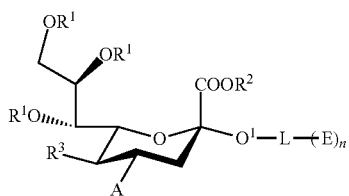

wherein
A is —OH, —OMe, —OC(=O)CH$_3$, —NH$_2$, —NHC(=O)CH$_3$, —NHCH$_2$OH, or —NHC(=NH)NH$_2$;
R$^1$ is, individually for each occurrence, —H, -Me, or —C(=O)CH$_3$;
R$^2$ is —H or -Me;
R$^3$ is —OH, —OMe, —OC(=O)CH$_3$, —NH$_2$, —NHC(=O)CH$_3$, or —NHCH$_2$OH;
n is an integer from 1 to 16;
L is absent or is a linking moiety, wherein when L is absent, 01 is also absent and n is 1; and
E is, individually for each occurrence, an electrochemically active moiety defined by one of the general formulae shown below

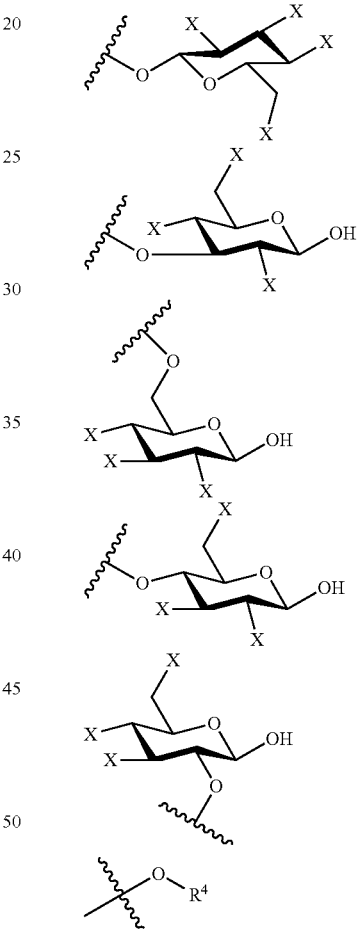

wherein
R$^4$ is a C$_1$-C$_6$ alkyl group, and
X is, individually for each occurrence, —OH, —OMe, —OC(=O)CH$_3$, —F, —CF$_3$, —CH$_2$F, —CHF$_2$, —Cl, —Br, —I, H or sulfonate.

* * * * *